United States Patent
Higgs, Jr. et al.

(10) Patent No.: US 11,591,387 B2
(45) Date of Patent: Feb. 28, 2023

(54) COMPOUNDS AND METHODS TARGETING INTERLEUKIN-19

(71) Applicant: Eli Lilly and Company, Indianapolis, IN (US)

(72) Inventors: Richard Earl Higgs, Jr., Zionsville, IN (US); Robert John Konrad, Carmel, IN (US); Brian Jeffrey Nickoloff, Carmel, IN (US); Robert William Siegel, II, Fountaintown, IN (US)

(73) Assignee: Eli Lilly and Company, Indianapolis, IN (US)

( * ) Notice: Subject to any disclaimer, the term of this patent is extended or adjusted under 35 U.S.C. 154(b) by 174 days.

(21) Appl. No.: 16/903,731

(22) Filed: Jun. 17, 2020

(65) Prior Publication Data
US 2020/0354444 A1    Nov. 12, 2020

Related U.S. Application Data

(63) Continuation of application No. PCT/US2019/013565, filed on Jan. 15, 2019.

(60) Provisional application No. 62/618,200, filed on Jan. 17, 2018.

(51) Int. Cl.
*G01N 33/53* (2006.01)
*C07K 16/24* (2006.01)

(52) U.S. Cl.
CPC ........ *C07K 16/244* (2013.01); *C07K 2317/34* (2013.01); *C07K 2317/565* (2013.01)

(58) Field of Classification Search
CPC .................................................. G01N 33/577
See application file for complete search history.

(56) References Cited

FOREIGN PATENT DOCUMENTS

WO    WO 2013/143026 A1  * 10/2013
WO    WO2014/168788      * 10/2014

OTHER PUBLICATIONS

Rudikoff et al.,Proc Natl Acad Sci USA. Mar. 1982;79(6):1979-83.*
Janeway et al.,Immunobiology, 3rd edition, 1997 Garland Publishing Inc..pp. 3:1-3:11.*
Edwards et al.,J Mol Biol. Nov. 14, 2003; 334(1):103-18.*
Lloyd et al., Protein Eng Des Sel. Mar. 2009; 22(3):159-68.doi:10.1093/protein/gzn058. Epub Oct. 29, 2008.*
Goel et al., J Immunol.Dec. 15, 2004; 173(12):7358-67.*
Kanyavuz et al.,Nat Rev Immunol. Jun. 2019; 19(6):355-368.doi:10.1038/S41577-019-0126-7.*
D'Angelo et al.,Front Immunol. Mar. 8, 2018;9:395. doi:10.3389/fimmu.2018.00395.e Collection 2018.*
Hsu, et al. "Interleukin-19 blockade attenuates collagen-induced arthritis in rats", Rheumatology, vol. 51 No. 3, Mar. 1, 2012, pp. 434-442.
North et al., *A New Clustering of Antibody CDR Loop Conformations*, Journal of Molecular Biology, 406:228-256 (2011).
Altschul et al., J. Mol. Biol. 215:403-410 (1990).

* cited by examiner

*Primary Examiner* — Prema M Mertz
(74) *Attorney, Agent, or Firm* — Duane Christopher Marks

(57) ABSTRACT

The present invention provides compounds and methods targeting human interleukin-19, including therapeutic antibodies, pharmaceutical compositions and diagnostic applications useful in the field of immune-mediated diseases including psoriasis, atopic dermatitis, psoriatic arthritis, bronchial asthma and diabetic nephropathy.

10 Claims, No Drawings

Specification includes a Sequence Listing.

COMPOUNDS AND METHODS TARGETING INTERLEUKIN-19

The present invention is in the field of medicine. More particularly, the present invention relates to compounds, pharmaceutical compositions, and methods which include an antibody directed against human interleukin-19 (IL-19). The compounds and methods of the present invention are expected to be useful in the field of autoimmune and chronic inflammatory diseases (collectively referred to herein as, immune-mediated diseases), particularly diseases such as psoriasis (Ps0), atopic dermatitis (AD), diabetic nephropathy (DN), bronchial asthma (BA), psoriatic arthritis (PsA) and the like, including treatment thereof and diagnostic applications relating thereto.

Interleukin-19 (IL-19) is a cytokine reported to belong to the interleukin-10 cytokine family (which includes IL-10, 20, 22 and 26 as well as some virus-encoded cytokines). IL-19 has been reported to have involvement in the IL-20R complex signaling pathway and to be expressed in resting monocytes, macrophages, B cells, and epithelial cells including keratinocytes.

Autoimmune diseases arise from the body's production of an immune response against its own tissue. Autoimmune diseases are often chronic and can be debilitating and even life-threatening. Ps0 is a chronic autoimmune disease with systemic manifestations including psoriatic arthritis, cardiovascular disease, metabolic syndrome and affective disorders. AD, along with many other forms of chronic autoimmune diseases such as Ps0, RA, AxSpA and PsA, affect the axial and/or peripheral skeleton.

Current FDA approved treatments for immune-mediated diseases include corticosteroids, often used to treat acute inflammation, and bioproducts targeting TNFα or interleukin-12 and 23. Although these treatments have demonstrated efficacy in reducing symptoms for a subset of patients, a large percentage of patients remain nonresponsive or experience a loss of response to the currently available treatments. For autoimmune diseases such as Ps0, ixekizumab is an FDA approved therapeutic antibody targeting IL-17A in which 90% of patients achieved a 75% reduction in the Psoriasis Assessment Skin Involvement (PAST) score (e.g. PASI 75). However, PASI assessments rely on subject inputs that can be difficult to assess in certain circumstances. To date, an objective, sensitive, and reproducible blood-based biomarker for assessing and informing clinical management of Ps0, and other immune-mediated diseases such as AD, DN and BA does not exist. Thus, there remains an unmet need for compounds, pharmaceutical compositions, and methods useful as therapeutics for, and/or in diagnostic applications relating to, immune-mediated diseases such as Ps0, AD, BA, DN and the like.

Accordingly, in certain embodiments, the present invention provides antibodies directed against human IL-19. According to some embodiments, the present invention provides antibodies which comprise a light chain variable region (LCVR) and a heavy chain variable region (HCVR), wherein the LCVR comprises complementarity determining regions (CDRs) LCDR1, LCDR2 and LCDR3 and the HCVR comprises CDRs HCDR1, HCDR2 and HCDR3 selected from the groupings of CDR combinations provided in Table 1, 2 or 3. In some embodiments, the LCVR comprises CDRs LCDR1, LCDR2 and LCDR3 and the HCVR comprises CDRs HCDR1, HCDR2 and HCDR3 having amino acid sequences with at least 95% homology to the amino acid sequences selected from the groupings of CDR combinations provided in Table 1, 2 or 3. According to particular embodiments, the present invention also provides antibodies comprising a LCVR and a HCVR selected from:
 a. the LCVR having the amino acid sequence of SEQ ID NO: 66 and the HCVR having the amino acid sequence of SEQ ID NO: 70;
 b. the LCVR having the amino acid sequence of SEQ ID NO: 74 and the HCVR having the amino acid sequence of SEQ ID NO: 78;
 c. the LCVR having the amino acid sequence of SEQ ID NO: 82 and the HCVR having the amino acid sequence of SEQ ID NO: 86;
 d. the LCVR having the amino acid sequence of SEQ ID NO: 34 and the HCVR having the amino acid sequence of SEQ ID NO: 38;
 e. the LCVR having the amino acid sequence of SEQ ID NO: 42 and the HCVR having the amino acid sequence of SEQ ID NO: 46;
 f. the LCVR having the amino acid sequence of SEQ ID NO: 50 and the HCVR having the amino acid sequence of SEQ ID NO: 54; and
 g. the LCVR having the amino acid sequence of SEQ ID NO: 58 and the HCVR having the amino acid sequence of SEQ ID NO: 62.

According to even more particular embodiments, the present invention also provides antibodies comprising a LC and a HC selected from, or having amino acid sequences with at least 95% homology to the amino acid sequences of:
 a. the LC having the amino acid sequence of SEQ ID NO: 2 and the HC having the amino acid sequence of SEQ ID NO: 6;
 b. the LC having the amino acid sequence of SEQ ID NO: 10 and the HC having the amino acid sequence of SEQ ID NO: 14;
 c. the LC having the amino acid sequence of SEQ ID NO: 18 and the HC having the amino acid sequence of SEQ ID NO: 22;
 d. the LC having the amino acid sequence of SEQ ID NO: 26 and the HC having the amino acid sequence of SEQ ID NO: 30;
 e. the LC having the amino acid sequence of SEQ ID NO: 310 and the HC having the amino acid sequence of SEQ ID NO: 311; and
 f. the LC having the amino acid sequence of SEQ ID NO: 312 and the HC having the amino acid sequence of SEQ ID NO: 313.

According to particular embodiments, the present invention provides human IL-19 neutralizing antibodies having a LCVR and a HCVR, wherein the LCVR comprises CDRs (LCDR1, LCDR2 and LCDR3) and the HCVR comprises CDRs (HCDR1, HCDR2 and HCDR3) selected from, or having amino acid sequences with at least 95% homology to the amino acid sequences of, the CDR combinations provided in Table 1, 2 or 3. In particular embodiments, the human IL-19 neutralizing antibodies of the present invention comprise a LCVR and a HCVR selected from:
 a. the LCVR having the amino acid sequence of SEQ ID NO: 66 and the HCVR having the amino acid sequence of SEQ ID NO: 70;
 b. the LCVR having the amino acid sequence of SEQ ID NO: 74 and the HCVR having the amino acid sequence of SEQ ID NO: 78;
 c. the LCVR having the amino acid sequence of SEQ ID NO: 82 and the HCVR having the amino acid sequence of SEQ ID NO: 86;
 d. the LCVR having the amino acid sequence of SEQ ID NO: 34 and the HCVR having the amino acid sequence of SEQ ID NO: 38;

e. the LCVR having the amino acid sequence of SEQ ID NO: 42 and the HCVR having the amino acid sequence of SEQ ID NO: 46;
f. the LCVR having the amino acid sequence of SEQ ID NO: 50 and the HCVR having the amino acid sequence of SEQ ID NO: 54; and
g. the LCVR having the amino acid sequence of SEQ ID NO: 58 and the HCVR having the amino acid sequence of SEQ ID NO: 62.

According to even more particular embodiments, the present invention also provides human IL-19 neutralizing antibodies having a LC and a HC selected from, or having amino acid sequences with at least 95% homology to the amino acid sequences of:
a. the LC having the amino acid sequence of SEQ ID NO: 2 and the HC having the amino acid sequence of SEQ ID NO: 6;
b. the LC having the amino acid sequence of SEQ ID NO: 10 and the HC having the amino acid sequence of SEQ ID NO: 14;
c. the LC having the amino acid sequence of SEQ ID NO: 18 and the HC having the amino acid sequence of SEQ ID NO: 22;
d. the LC having the amino acid sequence of SEQ ID NO: 26 and the HC having the amino acid sequence of SEQ ID NO: 30; and
e. the LC having the amino acid sequence of SEQ ID NO: 310 and the HC having the amino acid sequence of SEQ ID NO: 311; and
f. the LC having the amino acid sequence of SEQ ID NO: 312 and the HC having the amino acid sequence of SEQ ID NO: 313.

In embodiments, antibodies of the present invention comprise an IgG1 heavy chain. According to some embodiments, the antibodies further comprise kappa light chains.

According to some aspects of the present invention, human IL-19 antibodies, including human IL-19 neutralizing antibodies, are provided which bind human IL-19 within an epitope region comprising at least one or more of amino acid residues: 95-102; 67-75; 125-136; 67-75 and 125-136; 90-100; 42-60; 90-107; 149-160; 42-60, 90-107 and 149-160 of human IL-19 as given by SEQ ID NO. 1 (as determined my methods set forth in the present disclosure). In an embodiment, the present invention provides IL-19 antibodies that bind human IL-19 within an epitope region of human IL-19 which bins with an antibody provided herein.

According to some embodiments, the IL-19 antibodies of the present invention are useful in the treatment of immune-mediated diseases. In some more specific embodiments, the immune-mediated diseases are at least one of Ps0, AD, PsA, BA and/or DN. According to other embodiments of the present invention, the IL-19 antibodies of the present invention are useful in diagnostic applications for autoimmune diseases. In some more specific embodiments, the immune-mediated diseases are at least one of Ps0, AD and/or DN.

The present invention further provides pharmaceutical compositions comprising an IL-19 antibody of the present invention and one or more pharmaceutically acceptable carriers, diluents or excipients. Further, the present invention provides a method of treating an immune-mediated disease, such as Ps0, AD and/or DN, comprising administering to a patient in need thereof a pharmaceutical composition of the present invention.

In addition, the present invention provides a method of treating immune-mediated diseases. More particularly, the present invention provides a method of treating immune-mediated diseases, including Ps0, AD, PsA, BA or DN comprising administering to a patient in need thereof an effective amount of an IL-19 antibody of the present invention.

The present invention also provides an IL-19 antibody of the present invention for use in therapy. More particularly, the present invention provides an IL-19 antibody of the present invention for use in treatment of immune-mediated diseases including Ps0, AD, PsA and DN. In an embodiment, the present invention provides the use of an IL-19 antibody of the present invention in the manufacture of a medicament for the treatment of one or more immune-mediated diseases including Ps0, AD, PsA, BA and DN.

According to some embodiments, the present invention provides a method of detecting IL-19 in a patient sample comprising the steps of contacting the patient sample with a first antibody which binds a first epitope region of IL-19; contacting the patient sample with a second antibody which binds a second epitope region of IL-19 and has a detectable label; and detecting a signal provided by said detectable label. In some embodiments, the patient sample is one of blood, serum or plasma. According to some more specific embodiments, the first epitope region of IL-19 partially overlaps with the second epitope region of IL-19. Further, in some embodiments, said steps of contacting with the first and second antibodies occurs simultaneously. In some specific embodiments, the first antibody comprises a combination of LC and HC CDRs provided in Tables 1, 2 or 3. In some embodiments, the first antibody comprises a combination of LC and HC CDRs having 95% homology to the LC and HC CDRs provided in Tables 1, 2 or 3. In some specific embodiments, the second antibody comprises a combination of LC and HC CDRs provided in Tables 1, 2 or 3. In some embodiments, the second antibody comprises a combination of LC and HC CDRs having 95% homology to the LC and HC CDRs provided in Tables 1, 2 or 3. In more particular embodiments, the first and second antibodies do not bin together.

According to some embodiments of the present invention, a method of quantifying IL-19 in a patient sample is provided. Such method includes the steps of contacting the patient sample with a first antibody which binds a first epitope region of IL-19; contacting the patient sample with a second antibody which binds a second epitope region of IL-19 and said has a detectable label; and detecting the signal provided by said detectable label; contacting a control standard with a first antibody which binds the same first epitope region of IL-19 (as used in contacting the patient sample); contacting the control standard with a second antibody which binds the same second epitope region of IL-19 (as used in contacting the patient sample) and having a detectable label; and detecting a signal provided by said detectable signal. In some embodiments, the patient sample is one of blood, serum or plasma. According to some more specific embodiments, the first epitope region of IL-19 partially overlaps with the second epitope region of IL-19. Further, in some embodiments, said steps of contacting with the first and second antibodies occurs simultaneously. In some specific embodiments, the first antibody comprises a combination of LC and HC CDRs provided in Tables 1, 2 or 3. In some embodiments, the first antibody comprises a combination of LC and HC CDRs having 95% homology to the LC and HC CDRs provided in Tables 1, 2 or 3. In some specific embodiments, the second antibody comprises a combination of LC and HC CDRs provided in Tables 1, 2 or 3. In some embodiments, the second antibody comprises a combination of LC and HC CDRs having 95% homology to the LC and HC CDRs provided in Tables 1, 2 or 3. In more particular embodiments, the first and second antibodies do not bin together.

According to some embodiments, a method of diagnosing an immune-mediated disease is provided. Such method comprises the steps of contacting a patient sample with an IL-19 antibody and detecting binding between IL-19 in the patient sample and the antibody. According to some specific embodiments, the method of diagnosing includes diagnosing the patient as having; at risk for; in need of treatment for; and/or at risk of symptoms relating to an immune-mediated disease when the presence of IL-19 in the patient sample is detected as above a reference value. According to some more specific embodiments, such methods further include the steps of determining the reference value including the steps of contacting a control standard with a first antibody which binds the same first epitope region of IL-19 as used in contacting the patient sample; contacting the control standard with a second antibody having a detectable label and which binds the same second epitope region of IL-19 as used in contacting the patient sample; and detecting a signal provided by the detectable signal. In some embodiments, the first antibody comprises a combination of LC and HC CDRs provided in Tables 1, 2 or 3. In some embodiments, the first antibody comprises a combination of LC and HC CDRs having 95% homology to the LC and HC CDRs provided in Tables 1, 2 or 3. Some embodiments of the method of diagnosing an immune-mediated disease, provided herein, further includes the steps of contacting the patient sample with a second IL-19 antibody which binds a second epitope region of IL-19 and has a detectable label; and detecting a signal provided by the detectable label. In some specific embodiments, the IL-19 antibody comprises a combination of LC and HC CDRs provided in Table 1, 2 and 3. In some embodiments, the second IL-19 antibody comprises a combination of LC and HC CDRs provided in Table 1, 2 and 3. In some embodiments, the second antibody comprises a combination of LC and HC CDRs having 95% homology to the LC and HC CDRs provided in Table 1, 2, and 3. According to specific embodiments, the first epitope region of IL-19 partially overlaps with the second epitope region of IL-19. According to particular embodiments, the first and second antibodies do not bin together. According to further embodiments, the reference value is approximately 21 pg/mL. In further embodiments, the immune-mediated disease is one of Ps0, AD, PsA, BA and DN.

In even further embodiments, the present invention provides a method of treating an immune-mediated disease in a patient. Such methods comprise the steps of contacting a patient sample with an IL-19 antibody and detecting binding between IL-19 in the patient sample and the antibody; and diagnosing the patient as having; at risk for; in need of treatment for; and/or at risk of symptoms relating to an immune-mediated disease when the presence of IL-19 in the patient sample is detected as above a reference value. According to some more specific embodiments of the methods of treating provided herein, such methods further include the steps of determining the reference value including the further steps of contacting a control standard with a first antibody which binds the same first epitope region of IL-19 as used in contacting the patient sample; contacting the control standard with a second antibody having a detectable label and which binds the same second epitope region of IL-19 as used in contacting the patient sample; and detecting a signal provided by the detectable signal. In some specific embodiments, the IL-19 antibody comprises a combination of LC and HC CDRs provided in Tables 1, 2 and 3.

In some embodiments, the IL-19 antibody comprises a combination of LC and HC CDRs having 95% homology to the LC and HC CDRs provided in Tables 1, 2 or 3. According to some embodiments, the reference value is approximately 21 pg/mL. In embodiments, the immune-mediated disease is one of Ps0, AD and DN. In some embodiments, the patient sample is one of blood, serum or plasma. According to some embodiments, the method further includes the steps of contacting the patient sample with a second IL-19 antibody which binds a second epitope region of IL-19 and has a detectable label and detecting a signal provided by the detectable signal. In even further embodiments, the second antibody comprises a combination of LC and HC CDRs provided in Tables 1, 2 or 3. In some embodiments, the second antibody comprises a combination of LC and HC CDRs having 95% homology to the LC and HC CDRs provided in Tables 1, 2 or 3. According to particular embodiments, the first and second antibodies do not bin together.

As used herein, an "antibody" is an immunoglobulin molecule comprising 2 HCs and 2 LCs interconnected by disulfide bonds. The amino terminal portion of each LC and HC includes a variable region of about 100-120 amino acids primarily responsible for antigen recognition via the CDRs contained therein. The CDRs are interspersed with regions that are more conserved, termed framework regions ("FR"). Each LCVR and HCVR is composed of 3 CDRs and 4 FRs, arranged from amino-terminus to carboxy-terminus in the following order: FR1, CDR1, FR2, CDR2, FR3, CDR3, FR4. The 3 CDRs of the LC are referred to as "LCDR1, LCDR2, and LCDR3," and the 3 CDRs of the HC are referred to as "HCDR1, HCDR2, and HCDR3." The CDRs contain most of the residues which form specific interactions with the antigen. The functional ability of an antibody to bind a particular antigen is largely influenced by the six CDRs. Assignment of amino acids to CDR domains within the LCVR and HCVR regions of the antibodies of the present invention is based on the well-known Kabat numbering convention (Kabat, et al., *Ann. NY Acad. Sci.* 190: 382-93 (1971); Kabat et al., *Sequences of Proteins of Immunological Interest*, Fifth Edition, U.S. Department of Health and Human Services, NIH Publication No. 91-3242 (1991)), and North numbering convention (North et al., *A New Clustering of Antibody CDR Loop Conformations*, Journal of Molecular Biology, 406:228-256 (2011)).

LCs are classified as kappa or lambda, which are each characterized by a particular constant region as known in the art. HCs are classified as gamma, mu, alpha, delta, or epsilon, and define the isotype of an antibody as IgG, IgM, IgA, IgD, or IgE, respectively. The antibodies of the present invention include IgG HCs which can be further divided into subclasses, e.g., IgG1, IgG2, IgG3, IgG4. The carboxy-terminal portion of each HC defines a constant region primarily responsible for effector function. Particular embodiments of antibodies of the present invention may include one or more modifications in the constant region of each HC, for example that enhance or reduce effector function, as are known in the art.

The antibodies of the present invention are monoclonal antibodies. Monoclonal antibodies are antibodies derived from a single copy or clone including, for example, any eukaryotic, prokaryotic or phage clone, and not the method by which it is produced. Monoclonal antibodies can be produced, for example, by hybridoma technologies, recombinant technologies, phage display technologies, synthetic technologies, e.g., CDR-grafting, or combinations of such or other technologies known in the art.

Methods of producing and purifying antibodies are well known in the art and can be found, for example, in Harlow and Lane (1988), *Antibodies, A Laboratory Manual*, Cold Spring Harbor Laboratory Press, Cold Spring harbor, N.Y., chapters 5-8 and 15, ISBN 0-87969-314-2. For example, mice or rabbits may be immunized with human IL-19 and the resulting antibodies can be recovered, purified, and the amino acid sequences determined using conventional methods well known in the art. Likewise, a phage library may be screened, whereby thousands of Fab fragments are screened for interaction with human IL-19 and resulting interactions can be recovered, purified, and the amino acid sequences determined using conventional methods well known in the art, whereby initial lead antibodies can be constructed. According to possible embodiments, antibodies of the present invention may be engineered to contain one or more human framework regions surrounding CDRs derived from the non-human antibody. Human framework germline sequences can be obtained, for example, from ImMunoGeneTics (INGT) via their website, http://imgt.cines.fr, or from *The Immunoglobulin FactsBook* by Marie-Paule Lefranc and Gerard Lefranc, Academic Press, 2001, ISBN 012441351.

In particular embodiments of the present invention, the antibody, or the nucleic acid encoding same, is provided in isolated form. As used herein, the term "isolated" refers to a protein, peptide, or nucleic acid which is free or substantially free from other macromolecular species found in a cellular environment.

The antibodies of the present invention can be used in the treatment of patients. More particularly the antibodies of the present invention are expected to treat immune-mediated diseases or disorders, which include Ps0, AD, PsA, BA and DN. Although antibodies of the present invention are expected to be useful in the treatment of Ps0, AD and DN, such antibodies may also be useful in the treatment of other immune-mediated diseases, including RA, AxSpA and PsA and/or immune-mediated diseases specifically including epithelial cell involvement. As used interchangeably herein, "treatment" and/or "treating" and/or "treat" are intended to refer to all processes wherein there may be a slowing, interrupting, arresting, controlling, stopping, or reversing of the progression of the disorders described herein, but does not necessarily indicate a total elimination of all disorder symptoms. Treatment includes administration of an antibody of the present invention for treatment of a disease or condition in a human that would benefit from a reduction in IL-19 activity, and includes: (a) inhibiting further progression of the disease, i.e., arresting its development; and (b) relieving the disease, i.e., causing regression of the disease or disorder or alleviating symptoms or complications thereof.

As used interchangeably herein, the term "patient," "subject," and "individual," refers to a human. In certain embodiments, the patient is further characterized with a disease, disorder, or condition (e.g., an autoimmune disorder) that would benefit from a reduction in IL-19 activity. In other embodiments, the patient is further characterized as being at risk of developing an immune-mediated disease, disorder, or condition that would benefit from a reduction in IL-19 activity.

A patient "sample" as used herein refers to a human sample. Non-limiting sources of a sample for use in the present invention include blood, plasma, serum, spinal fluid, lymph fluid, biopsy aspirates, ascites, fluidic extracts, solid tissue, the external sections of the skin, respiratory, intestinal, and genitourinary tracts, tears, saliva, milk, tumors, organs, cell cultures and/or cell culture constituents.

As used herein, the term "bind (or binds)" IL-19 refers to an interaction of an antibody with a epitope region of human IL-19. The term "epitope region" refers to specific amino acids comprising IL-19 which provide an antigenic determinant capable of specific binding to an IL-19 antibody. The amino acids of an epitope region provide chemically active surface groupings of IL-19 and form a specific three dimensional structure of IL-19, and may provide specific charge characteristics. Binding may comprise interacting with the epitope region either through "conformational" or "linear" epitope binding of the antibody with human IL-19. Presented herein are exemplified embodiments of IL-19 antibodies that bind linear epitopes of human IL-19, and other exemplified embodiments of IL-19 antibodies that bind conformational epitopes. Conformational and nonconformational/linear epitopes may be distinguished in that the binding to the conformational epitope regions is lost in the presence of denaturing solvents whereas linear epitope regions is not. In a particular embodiment, the term "bind (or binds)" human IL-19 refers to an interaction with an epitope region comprising amino acid residues 95-102 of human IL-19, as determined my methods set forth in the present disclosure (residue numbering based on the exemplified human IL-19 of SEQ ID NO.1). In a further embodiment, the term "bind (or binds)" human IL-19 refers to an interaction with an epitope region comprising amino acid residues 90-100 of human IL-19, as determined my methods set forth in the present disclosure (residue numbering based on the exemplified human IL-19 of SEQ ID NO.1). In another particular embodiment, the term "bind (or binds)" human IL-19 refers to an interaction with an epitope region comprising amino acid residues 67-75 of human IL-19, as determined my methods set forth in the present disclosure (residue numbering based on the exemplified human IL-19 of SEQ ID NO.1). In another embodiment, the term "bind (or binds)" human IL-19 refers to an interaction with an epitope region comprising amino acid residues 125-136 of human IL-19, as determined my methods set forth in the present disclosure (residue numbering based on the exemplified human IL-19 of SEQ ID NO.1). In another particular embodiment, the term "bind (or binds)" human IL-19 refers to an interaction with an epitope region comprising amino acid residues 67-75 and 125-136 of human IL-19, as determined my methods set forth in the present disclosure (residue numbering based on the exemplified human IL-19 of SEQ ID NO.1). In a further embodiment, the term "bind (or binds)" human IL-19 refers to an interaction with an epitope region comprising amino acid residues 42-60 of human IL-19, as determined my methods set forth in the present disclosure (residue numbering based on the exemplified human IL-19 of SEQ ID NO.1). In an embodiment, the term "bind (or binds)" human IL-19 refers to an interaction with an epitope region comprising amino acid residues 90-107 of human IL-19, as determined my methods set forth in the present disclosure (residue numbering based on the exemplified human IL-19 of SEQ ID NO.1). In an embodiment, the term "bind (or binds)" human IL-19 refers to an interaction with an epitope region comprising amino acid residues 149-160 of human IL-19, as determined my methods set forth in the present disclosure (residue numbering based on the exemplified human IL-19 of SEQ ID NO.1). In another particular embodiment, the term "bind (or binds)" human IL-19 refers to an interaction with an epitope region comprising amino acid residues 42-60, 90-107 and 149-160 of human IL-19, as determined my methods set forth in the present disclosure (residue numbering based on the exemplified human IL-19 of SEQ ID NO.1). It should be understood that there are known variations of human IL-19, for example resulting from splice variants. It is also understood that such known variants may result in altered residue numbering for residues described here (for example, as in relation to the residue numbering presented in SEQ ID NO.1). Although the residue numbering may be altered in some variants, the amino acids comprising the epitope region remain the same. The term "epitope region" as used herein refers to discrete, three-dimensional sites of an antigen that are recognized, either in total or in part, by the antibodies of the present invention.

An antibody of the present invention can be incorporated into a pharmaceutical composition which can be prepared by methods well known in the art and comprise an antibody of the present invention and one or more pharmaceutically acceptable carrier(s) and/or diluent(s) (e.g., Remington, *The Science and Practice of Pharmacy*, 22$^{nd}$ Edition, Loyd V., Ed., Pharmaceutical Press, 2012, which provides a compendium of formulation techniques as are generally known to practitioners). Suitable carriers for pharmaceutical compositions include any material which, when combined with an antibody of the present invention, retains the molecule's activity and is non-reactive with the patient's immune system. A pharmaceutical composition comprising an antibody of the present invention can be administered to a patient at risk for, or exhibiting, diseases or disorders as described herein by parental routes (e.g., subcutaneous, intravenous, intraperitoneal, intramuscular, or transdermal). A pharmaceutical composition of the present invention contains an "effective" or "therapeutically effective" amount, as used interchangeably herein, of an antibody of the present invention. An effective amount refers to an amount necessary (at dosages and for periods of time and for the means of administration) to achieve the desired therapeutic result. An effective amount of an antibody may vary according to factors such as the disease state, age, sex, and weight of the individual, and the ability of the antibody to elicit a desired response in the individual. An effective amount is also one in which any toxic or detrimental effects of the antibody of the present invention are outweighed by the therapeutically beneficial effects.

The term percent homology, as used in the present disclosure, in the context of two or more amino acid sequence refers to two or more sequences having a specified percentage of amino acid residues that are the same, when compared and aligned for maximum correspondence, as measured using a sequence comparison algorithm (e.g., BLASTP and BLASTN or other algorithms available to persons of skill) or by visual inspection. Depending on the application, the percent homology can exist over a region of the sequence being compared, e.g., over a functional domain, or, alternatively, exist over the full length of the two sequences to be compared. By way of example, percent homology of a sequence may be compared to a reference sequence. For example, when using a sequence comparison algorithm, test and reference sequences may be input into a computer (and subsequence coordinates may be further designated if desired along with sequence algorithm program parameters). The sequence comparison algorithm then calculates the percent sequence identity or homology for the test sequence(s) relative to the reference sequence(s), based on the designated program parameters. Exemplary sequence alignment and/or homology algorithms are available through, Smith & Waterman, Adv. Appl. Math. 2:482 (1980, Needleman Wunsch, J. Mol. Biol. 48:443 (1970), Pearson & Lipman, Proc. Nat'l. Acad. Sci. USA 85:2444 (1988), GAP, BESTFIT, FASTA, and TFASTA (in the Wisconsin Genetics Software Package, Genetics Computer Group, 575 Science Dr., Madison, Wis.), or by visual inspection (see generally Ausubel et al., infra). One example of an algorithm that is suitable for determining percent sequence identity and sequence similarity is the BLAST algorithm, which is described in Altschul et al., J. Mol. Biol. 215:403-410 (1990). Software for per BLAST analyses is publicly available through the National Center for Biotechnology Information (www.ncbi.nlm.nih.gov/).

The present disclosure also pertains to methods of clinical diagnosis, prognosis, or theranosis of a subject performed by a medical professional using the methods disclosed herein. The methods, as described herein, can, for example, be performed by an individual, a health professional, or a third party, for example a service provider who interprets genotype information from the subject. As explained herein, a medical professional may initiate or modify treatment after receiving information regarding a diagnostic method of the present disclosure. For example, a medical professional may recommend a therapy or a change in therapy.

Antibodies of the instant disclosure can be used to isolate, detect and/or quantify IL-19 by standard techniques, such as affinity chromatography, immunoprecipitation, immunohistochemistry or ELISA-based assay. Such assay can be used to detect and/or evaluate the abundance and/or patterns of IL-19 expression for diagnostic, prognostic, or theranostic purposes to monitor polypeptide levels, for example in serum, plasma, blood or tissue as part of a clinical testing procedure, e.g., to determine the efficacy of a given treatment regimen.

IL-19 levels or measurements, as provided by assays of the present invention, may be absolute values (e.g., concentration within a biological sample) or relative values (e.g., concentration compared to a reference). As used herein, IL-19 is referred to as "increased" in a patient sample if the method for detecting IL-19 indicates that the level or concentration of IL-19 in the patient sample is higher than a reference value. Conversely, IL-19 is referred to as "decreased" in a patient sample if the IL-49 level or concentration of IL-19 in a patient sample is lower than a reference value, or for example, the IL-19 value measured in a previous patient sample.

A "reference value" as used herein refers to a known, or approximate concentration of IL-19 associated with a specific condition. The concentration levels in a reference value can be an absolute or relative amount, a range of amount, or a minimum amount, a mean amount, and/or a median amount of IL-19. A reference value can also serve as a baseline of IL-19 to which a value derived from a patient sample is compared. According to some embodiments, the reference value may include a reference value of approximately 21 pg/mL.

A "control standard," as used herein, refers to a sample that can be used to compare the results obtained from a patient sample in the methods of the invention. Control standards can be cells, tissue, or known protein concentrations spiked into a media. The concentration levels in a control standard can be an absolute or relative amount, a range of amount, or a minimum amount, a mean amount, and/or a median amount of IL-19. A control standard can also serve as a baseline of IL-19 to which the patient sample is compared. The control standard can include a concentration value from the same patient or a known, normal reference of IL-19. According to some embodiments, the control standard may include a reference value of approximately 21 pg/mL. Further, in some embodiments, a control standard may express IL-19 concentrations in the form of a standard curve.

As used herein, the term "capture antibody" or "first antibody" refers to an IL-19 antibody capable of binding and capturing IL-19 in a patient sample under suitable conditions, such that the capture antibody-IL-19 complex can be separated from the rest of the sample. In some embodiments, the capture antibody is immobilized. In some embodiments, the capture antibody is labeled with a detectable label. In some embodiments, the capture antibody is immobilized in a "sandwich" immunoassay, and the capture or first IL-19 antibody binds a specific or first epitope region of IL-19. In such sandwich immunoassays, a "detection (or second) antibody" is also utilized. According to some embodiments a detection or second antibody may bind specifically to the capture antibody and may be labelled with a detectable label. In some embodiments, the detection of second antibody binds to the IL-19 already bound, or captured, by the capture or first antibody. In such embodiments, the detection antibody binds IL-19 at a second epitope region and may be labelled with a detectable label.

As understood in the art, an antibody of the present invention may be coupled to a "detectable label" to facilitate its detection As used herein, a detectable label is a moiety, composition or technique which can be used to detect the binding of the detection antibody to the capture antibody-IL-19 complex. According to some embodiments, the detectable label may be conjugated to the antibody (either capture or detection, as the case may be) directly or indirectly. Examples of detectable labels include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichloromazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$. Antibodies of the present invention can also be useful in pharmacogenomic analysis. Such embodiments, may be used to identify individuals that can benefit from specific or modified treatment modalities and/or monitor efficacy of present treatment regimens.

The term "diagnosis" or "diagnosing", as used interchangeably herein, refers to methods by which the skilled artisan can estimate and/or determine the probability ("a likelihood") of whether or not a patient is suffering from a given disease or condition. In the case of the present invention, "diagnosing" the patient includes using the results of an assay of the present invention to identify or diagnose an autoimmune disease or element related to an autoimmune disease and the patient (that is, the presence or occurrence of an autoimmune disease or the need for treatment, or the effectiveness of a treatment against the autoimmune disease with the patient). A diagnosis may, according to the present invention, be based on a combination of other clinical indicia, as understood by a healthcare professional, to arrive at a diagnosis.

EXAMPLES

Expression of IL-19 Antibodies

Murine-derived IL-19 antibodies of the present invention are generated employing hybridoma methodology (e.g., as as first described by Kohler et al, Nature, 256:495 (1975)). Briefly, the mouse is immunized with recombinant human IL-19 and lymphocytes capable of producing antibodies that hind human IL-19 are isolated and fused with a myeloma cell line using a suitable fusing agent for forming a hybridoma cell (Coding, Monoclonal Antibodies: Principles and Practice, pp. 59-103 (Academic Press, 1986)). Hybridomas are seeded and grown in a suitable culture medium (preferably containing one or more substances inhibiting survival of unfused myeloma cells). Binding specificity of monoclonal antibodies produced by hybridomas is then determined by by an in vitro binding assay (e.g., immunoprecipitation, radioimmunoassay (RIA), or enzyme-linked immunosorbent assay (ELISA)). Preferred hybridomas may be subcloned by limiting dilution procedures and grown by standard methods including in vivo as ascites tumors in an animal (Goding, Monoclonal Antibodies: principles and Practice, pp. 59-103 (Academic Press, 1986)). Monoclonal antibodies secreted by the hybridomas (and or subclones) are purified according to conventional procedures such as, for example, affinity chromatography (e.g., protein A or protein G-Sepharose) or ion-exchange chromatography, hydroxylapatite chromatography, gel electrophoresis, or the like. Affinity maturation of antibodies may be performed according to methods known in the field.

cDNA encoding antibodies of the present invention is sequenced using conventional procedures. cDNA sequences encoding the heavy and light chains may be cloned and engineered into a GS (glutamine synthetase) expression vector. The engineered immunoglobulin expression vector may then be stably transfected into CHO cells. As one of skill in the art will appreciate, mammalian expression of antibodies will result in glycosylation, typically at highly conserved N-glycosylation sites in the Fc region. Stable clones may be verified for expression of an antibody specifically binding to human IL-19. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized. CDR sequences of exemplified embodiments of murine-derived IL-19 antibodies of the present invention, which have been affinity optimized as known in the art, are provided in Table 1.

TABLE 1

Murine Immunization-Derived Antibody CDR Amino Acid Sequences

| | Light Chain CDRs SEQ ID NOs. | | | Heavy Chain CDRs SEQ ID NOs. | | |
|---|---|---|---|---|---|---|
| Antibody | LCDR1 | LCDR2 | LCDR3 | HCDR1 | HCDR2 | HCDR3 |
| M_1 | 3 | 4 | 5 | 7 | 8 | 9 |
| M_2 | 11 | 12 | 13 | 15 | 16 | 17 |
| M_3 | 19 | 20 | 21 | 23 | 24 | 25 |
| M_4 | 27 | 28 | 29 | 31 | 32 | 33 |
| M_5 | 303 | 304 | 305 | 307 | 308 | 309 |

Rabbit-derived IL-19 antibodies of the present invention are generated after obtaining antibody gene sequences directly from B a rabbit is immunized with recombinant human IL-19 and mRNA is isolated from antigen-specific B cells enriched from PBMCs. Nucleic acid sequence encoding the heavy and light chain variable regions from this library are then cloned into a cell-based display system. Functional binding fragments are isolated from library, the individual gene sequences determined, cloned for recombinant IgG expression, and purified essentially as described above with regard to murine-derived IL-19 antibodies. CDR sequences of exemplified embodiments of rabbit-derived IL-19 antibodies of the present invention, which have been affinity optimized as known in the art, are provided in Table 2.

TABLE 2

Rabbitt Immunization-Derived Antibody CDR Amino Acid Sequences.

| | Light Chain CDRs SEQ ID NOs. | | | Heavy Chain CDRs SEQ ID NOs. | | |
|---|---|---|---|---|---|---|
| Antibody | LCDR1 | LCDR2 | LCDR3 | HCDR1 | HCDR2 | HCDR3 |
| R_1 | 35 | 36 | 37 | 39 | 40 | 41 |
| R_2 | 43 | 44 | 45 | 47 | 48 | 49 |
| R_3 | 51 | 52 | 53 | 55 | 56 | 57 |
| R_4 | 59 | 60 | 61 | 63 | 64 | 65 |
| R_5 | 90 | 91 | 92 | 93 | 94 | 95 |
| R_6 | 96 | 97 | 98 | 99 | 100 | 101 |
| R_7 | 102 | 103 | 104 | 105 | 106 | 107 |
| R_8 | 108 | 109 | 110 | 111 | 112 | 113 |
| R_9 | 114 | 115 | 116 | 117 | 118 | 119 |
| R_10 | 120 | 121 | 122 | 123 | 124 | 125 |
| R_11 | 126 | 127 | 128 | 129 | 130 | 131 |
| R_12 | 132 | 133 | 134 | 135 | 136 | 137 |
| R_13 | 138 | 139 | 140 | 141 | 142 | 143 |
| R_14 | 144 | 145 | 146 | 147 | 148 | 149 |
| R_15 | 150 | 151 | 152 | 153 | 154 | 155 |
| R_16 | 156 | 157 | 158 | 159 | 160 | 161 |
| R_17 | 162 | 163 | 164 | 165 | 166 | 167 |
| R_18 | 168 | 169 | 170 | 171 | 172 | 173 |
| R_19 | 174 | 175 | 176 | 177 | 178 | 179 |
| R_20 | 180 | 181 | 182 | 183 | 184 | 185 |
| R_21 | 186 | 187 | 188 | 189 | 190 | 191 |
| R_22 | 192 | 193 | 194 | 195 | 196 | 197 |
| R_23 | 198 | 199 | 200 | 201 | 202 | 203 |
| R_24 | 204 | 205 | 206 | 207 | 208 | 209 |
| R_25 | 210 | 211 | 212 | 213 | 214 | 215 |
| R_26 | 216 | 217 | 218 | 219 | 220 | 221 |
| R_27 | 222 | 223 | 224 | 225 | 226 | 227 |
| R_28 | 228 | 229 | 230 | 231 | 232 | 233 |
| R_29 | 234 | 235 | 236 | 237 | 238 | 239 |
| R_30 | 240 | 241 | 242 | 243 | 244 | 245 |
| R_31 | 246 | 247 | 248 | 249 | 250 | 251 |
| R_32 | 252 | 253 | 254 | 255 | 256 | 257 |
| R_33 | 258 | 259 | 260 | 261 | 262 | 263 |
| R_34 | 264 | 265 | 266 | 267 | 268 | 269 |
| R_35 | 270 | 271 | 272 | 273 | 274 | 275 |
| R_36 | 276 | 277 | 278 | 279 | 280 | 281 |
| R_37 | 282 | 283 | 284 | 285 | 286 | 287 |
| R_38 | 286 | 287 | 288 | 289 | 290 | 291 |
| R_39 | 295 | 296 | 297 | 299 | 300 | 301 |

Phage-derived IL-19 antibodies of the present invention are isolated from antibody phage libraries employing common techniques such as described above, as described in McCafferty et al., Nature, 348:552-554 (1990), Clackson et al., Nature, 352:624-628 (1991) and Marks et al., J. Mol. Biol., 222:581-597 (1991). cDNA sequences encoding the heavy and light chains of phage-derived antibodies of the present invention may be cloned and engineered into a GS (glutamine synthetase) expression vector for recombinant expression in a competent cell line, such as CHO cells. CDR sequences of exemplified embodiments of phage-derived IL-19 antibodies of the present invention are provided in Table 3.

TABLE 3

Phage-Derived Antibody CDR Amino Acid Sequences.

| Antibody | Light Chain CDRs SEQ ID NOs. | | | Heavy Chain CDRs SEQ ID NOs. | | |
|---|---|---|---|---|---|---|
| | LCDR1 | LCDR2 | LCDR3 | HCDR1 | HCDR2 | HCDR3 |
| P_1 | 67 | 68 | 69 | 71 | 72 | 73 |
| P_2 | 75 | 76 | 77 | 79 | 80 | 81 |
| P_3 | 83 | 84 | 85 | 87 | 88 | 89 |

Binding Kinetics and Affinity

Bio-layer interferometry (BLI) assay, measured with a Octet Red96® instrument available from ForteBio (using HBS-EP+ running buffer (GE Healthcare, 10 mM Hepes pH7.4+150 mM NaCl+3 mM EDTA+0.05% surfactant P20) at 25° C.), is used to measure binding of the exemplified IL-19 antibodies of the present invention to recombinant human IL-19 (having the amino acid sequence set for in SEQ ID NO: 1).

Except as noted, all reagents and materials are from ForteBio (Freemont, Calif.). An AMQ biosensor is used to immobilize antibody of interest for analysis. Exemplified antibody samples of the present invention (R_1, R_2, R_3, R_4, R_39, M_1, M_2 and M_5) are prepared at 5 µg/mL by dilution into running buffer. Recombinant human IL-19 is prepared to concentrations of 270, 90, 30, 10, 3.33, 1.11, 0.370, and 0 (blank) nM by dilution into running buffer. Each analysis consists of: (1) capturing antibody samples on biosensors for 300 secs; (2) establishing a baseline by incubating antibody loaded biosensors with running buffer for 60 secs; (3) incubating antibody loaded biosensors with serially diluted recombinant human IL-19 for 300 secs to monitor association phase; (4) return of biosensor to running buffer to monitor dissociation phase.

Binding data is processed using standard double-referencing and fit to a 1:1 binding model using Data Analysis v9.0 evaluation software, to determine the association rate ($k_{on}$, $M^{-1}s^{-1}$ units), dissociation rate ($k_{off}$, $s^{-1}$ units), and $R_{max}$ (nm units). The equilibrium dissociation constant (KO) was calculated from the relationship $K_D = k_{off}/k_{on}$, and is in molar units. Results are provided in Table 4.

TABLE 4

SPR binding data to recombinant human IL-19.

| Exemplified Antibody | $k_{on}$ ($M^{-1}s^{-1}$ units) | $k_{off}$ ($M^{-1}s^{-1}$ units) | $K_D$* (M) |
|---|---|---|---|
| R_1 | $3.33 \times 10^4$ | $1.04 \times 10^{-5}$ | $3.11 \times 10^{-10}$ |
| R_2 | $4.28 \times 10^5$ | $4.42 \times 10^{-5}$ | $1.03 \times 10^{-10}$ |
| R_3 | $3.91 \times 10^5$ | $<1.00 \times 10^{-7}$ | $<1.00 \times 10^{-12}$ |
| R_4 | $1.52 \times 10^5$ | $1.30 \times 10^{-3}$ | $8.52 \times 10^{-9}$ |
| R_39 | $2.06 \times 10^5$ | $3.48 \times 10^{-2}$ | $1.70 \times 10^{-7}$ |
| M_1 | $1.10 \times 10^6$ | $6.32 \times 10^{-5}$ | $5.76 \times 10^{-11}$ |
| M_2 | $6.37 \times 10^4$ | $1.85 \times 10^{-4}$ | $2.90 \times 10^{-9}$ |
| M_5 | $6.88 \times 10^5$ | $3.58 \times 10^{-5}$ | $5.21 \times 10^{-11}$ |

*$K_D$ results are considered relative as the results are not normalized for influence of avidity.

Epitope Mapping

PEPperCHIP® peptide microarray linear epitope mapping of exemplified antibody M_1 against human IL-19 is performed, according to manufacturer instructions, for high resolution linear epitope mapping. Briefly, exemplified antibody M-1 is incubated with a custom PEPperCHIP® peptide microarray comprising overlapping 12-mer peptide fragments of human IL-19. Scanning intensity is resolved using manufacturer software. An epitope, consisting of residues 95-102 (EPNPKILR) of SEQ ID NO. 1 is revealed, according to PEPperCHIP® analysis, for exemplified antibody M_1. Other murine-derived and rabbit-derived exemplified antibodies of the present invention do not yield a linear epitope, indicating human IL-19 conformational epitope binding.

Hydrogen deuterium exchange coupled with mass spectrometry (HDX-MS) is performed to map epitope regions of human IL-19 recombinant protein for exemplified antibodies M_2, M_3, M_5 and R_39. Briefly, HDX-MS is performed on a Waters nanoACQUITY system with HDX technology, including a LEAP HDX robotic liquid handling system and mass analysis is performed on a Waters Xevo G2—Tof mass spectrometer. The complex of human IL-19 with exemplified antibodies M_2, M_3, M_5, and R_39 is prepared at the molar ratio of 1:1.2 in 10 mM sodium phosphate buffer, pH 7.4 containing 150 mM NaCl (1×PBS buffer). The deuterium exchange experiment is initiated adding 55 uL of D20 buffer containing 0.1×PBS to 5 ul of human IL-19 or the human IL-19/antibody complex at 15° C. for various amounts of time (0 s, 10 s, 1 min, 10 min, 60 min, 120/240 min). The reaction is quenched using equal volume of was 0.32M TCEP, 0.1M phosphate pH 2.5 for two minutes at 1° C. 50 µL of the quenched reaction is injected on to an on-line pepsin column (Waters BEH Enzymate) at 14° C., using 0.2% formic acid in water as the mobile phase at a flow rate of 100 µL/min for 4 min. The resulting peptic peptides are then separated on a C18 column (Waters, Acquity UPLC BEH C18, 1.7 µm, 1.0 mm×50 mm) fit with a Vanguard trap column using a 3 to 85% acetonitrile (containing 0.2% formic acid) gradient over 10 min at a flow rate of 50 µL/min. The separated peptides are directed into a Waters Xevo G2 time-of-flight (qTOF) mass spectrometer. The mass spectrometer is set to collect data in the $MS^E$, $ESI^+$ mode; in a mass acquisition range of m/z 255.00-1950.00; with a scan time of 0.5 s. The Xevo G2 is calibrated with Glu-fibrinopeptide prior to use. All acquired data is mass corrected using a 2 µg/ml solution of LeuEnk in 50% ACN, 50% H$_2$O and 0.1% FA at a flowrate of 5 µl/min every 30 s (m/z of 556.2771). The peptides are initially identified by Waters Protein Lynx Global Server 3.02. The processing parameters are set to low energy threshold at 100.0 counts, an elevated energy threshold at 50.0 counts and an intensity threshold at 1500.0 counts. The resulting peptide list is imported to Waters DynamX 3.0 software, with threshold of 5 ppm mass error, 20% fragments ions per peptide based on peptide length. The relative deuterium incorporation for each peptide is determined by processing the MS data for deuterated samples along with the non-deuterated control in DynamX.

Sequence coverage from 90.9 to 94.8% of human IL-19 protein, with HDX-MS as described, is observed. When in complex with the exemplified antibodies, decreased deuterium uptake is observed at the residues of SEQ ID NO. 1 as denoted: M_2 and M_3: residues 67-75 (QIIKPLDVC) and 125-136 (RQCHCRQEATNA); M_5 residues 90-100 (FKDHQEPNPKI); and R_39 residues 42-60 (QEIKRAI-QAKDTFPNVTIL), 90-107 (FKDHQEPNPKILRKISSI), and 149-160 (VHAAAIKSLGEL).

Binning Experiments

Binning experiments involve competing monoclonal antibodies against one another in a pairwise and combinatorial fashion for binding to a specific antigen. A "bin" is a relative concept, based upon the epitope regions represented within the panel of monoclonal antibodies being tested. Two antibodies belong to the same bin if they cannot pair with one another and share the same blocking profile when tested against the other antibodies (or bins of antibodies) in the test panel. Binning of exemplified antibodies of the present invention may be performed by cross-competition binding assays using the Octet Red96®, available from ForteBio, according to manufacturer instruction. Briefly, to determine if two antibodies share overlapping epitope regions, an exemplified antibody is labeled with biotin and captured onto streptavidin sensor tip. The coated biosensor tip is then incubated with recombinant human IL-19 to saturate the capture antibody binding sites. The capture antibody-antigen complex is then incubated with a detection antibody. A change in wavelength is detected if the detection antibody is capable of binding. Antibodies with a same binding profile are grouped together into the same bin. Results are presented in Table 5.

TABLE 5

Antibody Binning Groups

| Exemplified Antibody | Binning Group |
| --- | --- |
| M_1 | 1 |
| M_2 | 2 |
| M_3 | 2 |
| M_4 | 1 |
| M_5 | 1 |
| R_1 | 3 |
| R_2 | 3 |
| R_3 | 3 |
| R_4 | 4 |

Neutralization of IL-19 In Vitro

Antibodies of the present invention are expected to neutralize IL-19. Neutralization of IL-19 activity by antibodies of the present invention may be assessed by one or more of the IL-19/IL-19 receptor binding assay formats, as well as IL-19 binding assays, for example, as described below.

In an example, IL-19 is radiolabeled, for example, with iodine-125 or tritium. Cells (e.g., transfected with the IL-19 receptor, transformed keratinocytes that endogenously express the IL-19 receptor, or primary human cells such as keratinocytes that express the IL-19 receptor) expressing the IL-19 receptor such as IL-20R1 are used in the assay which may be conducted in buffered media, such as HBSS with calcium and magnesium and with whole cells. Accordingly, the cells may be incubated with the labeled IL-19 in the assay buffer at 4, 20 or 37° C. for 1 to 6 hours. A readout provides the amount of label bound to the cells after separation of unbound tracer, such as with filtration though a glass fiber filter. Alternatively, neutralization may be assessed by way of a proximity based assay, such as with SPA beads. Further, a neutralization assay utilizing non-radioactive label IL-19 protein may be used.

Such neutralization assays involve pre-incubation of the antibody being assessed with the labeled IL-19 (for example, for 1 hour) before addition to the binding assay (as well as control samples in which no antibody targeting IL-19 is involved). Concentrations of labeled IL-19 near the 50% binding level (EC50) may be used, as well as varying concentrations (for example, in assessing a dose response of the antibody such as from about 100 micromolar down to about 1 picomolar). Antibody inhibition assessed for a range allows for determination of potency (IC50).

According to another method for assessing neutralization of IL-19 by antibodies of the present invention, the IL-19 protein is labeled with a fluorescent dye for flow cytometry (e.g., Alexa-647) and used to label cells, such as human keratinocytes. The binding may then be measured using flow cytometry. Neutralization of IL-19 by the antibody is assessed by pre-incubating the antibody with the labeled IL-19 (for example, for 1 hour at 4° C.) before adding the mixture to the cells (with staining occurring for about 3 hours at 4° C.). Concentrations of fluorescently labeled IL-19 near its 50% binding level (EC50) may used, as well as varying concentrations (for example, in assessing a dose response of the antibody such as from about 100 micromolar down to about 1 picomolar). Antibody inhibition of binding of the labeled IL-19 to its receptor is reflected by measurement of loss of labeled cells, and a potency (IC50) for the antibody may be determined.

Alternatively, a biophysical assay such as bio-layer interferometry (BLI) may be used for assessing neutralization of IL-19 by antibodies of the present invention. Binding between a ligand immobilized on the biosensor tip surface and an analyte in solution produces an increase in optical thickness at the biosensor tip, which results in a wavelength shift (expressed in nm). According to such assay, the IL-19 receptor (i.e., IL-20R1) is expressed in a membrane-free manner (such as with an Fc-fusion e.g. IL20Rbeta Fc chimera protein from R&D Systems catalog 1788-IR-050). AMQ or anti-rabbit conjugated biosensors (ForteBio) are used to immobilize anti-IL-19 antibody of interst (M_1, M_2, M_3, M_5 and R_39). The immobilized antibodies are then incubated with recombinant human IL-19 protein diluted to 100 nM using HBS-EP+ running buffer (GE Healthcare, 10 mM Hepes pH7.4+150 mM NaCl+3 mM EDTA+0.05% surfactant P20) for 240-300 secs. The human IL-19, after binding to the anti-IL-19 antibody, is assessed by incubation with human IL-20R beta Fc-fusion protein for 240-300 secs. The ability of the antibody to block or neutralize binding of the IL-19 ligand to the soluble receptor is observed as a minimal (<0.025 nm) increase in the wavelength during this step of the assay. Results are provided in Table 6.

TABLE 6

In vitro neutralization.

| Exemplified Antibody | IL-20R beta Fc protein binding response (nm) | Neutralization |
| --- | --- | --- |
| M_1 | −0.0075 | Yes |
| M_2 | 0.3614 | No |
| M_3 | 0.3539 | No |
| M_5 | −0.0124 | Yes |
| R_39 | −0.0421 | Yes |

Another method of assessing neutralization of IL-19 by antibodies of the present invention includes addition of such antibody, pre-incubated with human IL-19, to human keratinocytes. Exogenous IL-19 to human keratinocytes induces expression of additional IL-19 and other inflammatory molecules such as IL-8, CCL20 and S100A7. After pre-incubation of the antibody and IL-19 (for example, for 1 hr at 4° C.), the antibody-IL-19 mixture is added to cultured human keratinocytes. The cells are then cultured for 1 to 48 hrs and one or more of IL-19, IL-8, CCL20 and S100A7 (or other molecule expressed downstream of IL-19) in the supernatant is measured, for example, by ELISA (alternatively, mRNA of the downstream molecule may be measured). Antibody inhibited IL-19 function will demonstrate a reduced expression of the downstream molecule by the cultured keratinocytes.

PathHunter® eXpress IL20RA/IL20RB dimerization assay (DiscoverX product code 93-1027E3) is used to assess ability of exemplified antibodies to prevent binding of human IL-19 recombinant protein in a cell-based assay format. The assay detects ligand induced dimerization of two subunits of a receptor-dimer pair. The cells have been engineered to co-express one receptor subunit fused to enzyme donor and a second dimer partner fused to enzyme acceptor. Binding of an agonist to one receptor subunit induces it to interact with its dimer partner, forcing complementation of the two enzyme fragments resulting in the formation of a functional enzyme that hydrolyzes a substrate to generate a chemiluminescent signal. Briefly, cells are plated at 2500 cells per well and cultured at 37° C./5% $CO_2$ for 4 hours before addition of human IL-19 recombinant protein pre-mixed with various concentrations, ranging from 10 to 0.00001 μg/ml including a buffer only control, of exemplified antibodies (M_1 and M_5). Human IL-19 recombinant protein with and without exemplified antibodies mixture is then incubated with cells overnight at 37° C./5% $CO_2$. Substrate buffer is added to cells and incubated at room temperature for 1 hour in the dark before luminescent detection. The concentration of exemplified antibody resulting in inhibition of 50% of signal (IC50) and the maximum signal inhibition percentage (% inhibition) is tabulated for eight experiments with standard error of the mean (SEM) denoted below. Results are provided in Table 7.

TABLE 7

Cell-based neutralization.

| Exemplified Antibody | IC50 +/− SEM (μg/ml) | % inhibition +/− SEM |
|---|---|---|
| M_1 | 0.48 +/− 0.06 | 98.59 +/− 0.42 |
| M_5 | 0.64 +/− 0.20 | 105.03 +/− 1.38 |

IL-19 Assay

Plaque type psoriasis is currently measured based on measures of overall body surface involvement (BSA) and/or assessments of degree of erythema, thickness and scale of psoriasis lesions (PAST). However, given subjective input required with these methods they may not be linear depending on severity of skin involvement. No single blood-derived marker has been identified which allows for assessing overall psoriasis activity. Therefore, a more objective and reproducible method to determine severity is desired. The present invention provides a highly sensitive and specific assay to measure IL-19 levels in patients samples such as blood, serum and plasma. As illustrated herein, the IL-19 assay of the present invention provides an accurate diagnostic tool for therapy responsiveness (i.e., a predictive biomarker), disease reoccurrence (i.e., a prognostic biomarker), disease onset, and disease severity in patients with moderate-to-severe Ps0.

According to an exemplified embodiment, a sandwich ELISA assay for the sensitive detection of IL-19 is provided herein. The assay utilizes exemplified IL-19 antibodies of the present invention, for example, as set forth in Table 1, 2 or 3. According to an exemplified embodiment, a first IL-19 antibody (selected from Table 1, 2 or 3) is utilized as an IL-19 capture antibody and a second IL-19 antibody (selected from Table 1, 2 or 3) is utilized as an IL-19 reporter antibody. In some embodiments the first and second IL-19 antibodies are selected from separate epitope bins (for example, in specific embodiments, exemplified IL-19 antibody M_1 is paired with exemplified IL-19 antibody M_2). According to some embodiments, one milligram of the first IL-19 antibody (the capture antibody) is biotinylated using Pierce biotinylation kit (Cat #) and one milligram of the second IL-19 antibody (the reporter antibody) is labeled with ruthenium using MesoScale Discovery (MSD) kit for electrochemiluminescent (ECL) detection. According to such embodiment, labeled antibodies are evaluated using MALDI-TOF to ensure suitable labeling, and then diluted in 50% glycerol and stored at −20° C. prior to use.

Streptavidin-coated 96-well MSD plates are washed three times with TBST (Tris buffered saline containing 10 mmol/L Tris pH 7.40, 150 mmol/L NaCl with 1 mL Tween 20/L) and then blocked with TBS-T plus 1% BSA for 1 hour at room temperature. Plates are again washed and wells are then incubated with biotinylated IL-19 capture antibody (1 mg/L) for 1 hour. Thereafter, plates are again washed prior to patient sample testing.

During patient sample testing, a standard curve is generated using 50 μL of recombinant human IL-19 control standard (serially diluted IL-19 recombinant protein ranging from 100-0.0001 ng/L, and including a zero blank, in assay buffer of 50 mmol/L HEPES, pH 7.40, 150 mmol/L NaCl, 10 mL/L Triton X-100, 5 mmol/L EDTA, and 5 mmol/L EGTA). Data from ten separate standard curves, prepared as described herein, shows a dynamic range of $10^{-1}$ pg/mL to $10^5$ pg/mL of IL-19 (providing an sensitive and broad dynamic range in the therapeutic and diagnostic assays provided herein). Patient samples (which, according to the present invention, may include blood, serum or plasma) are diluted 1:4 in assay buffer and added to respective wells. The plate is incubated overnight at 4° C. Following incubation, wells are aspirated and washed 3 times with TB ST. Thereafter, 50 μL of ruthenium-labeled IL-19 detection antibody (0.5 mg/L) is added to the wells for a 1-hour incubation at room temperature. Following incubation, wells are aspirated and washed 3 times with TBST. Thereafter, 150 μl of 2×MSD read buffer is added. Ruthenium electrochemiluminescence in the wells is detected using a MSD Sector 6000 plate reader. Data is analyzed and IL-19 MSD immunoassay calibration curve fitting is performed using MesoScale Discovery software. SAS® software version 9.4 (PROC MIXED) is used for assessing treatment effects on IL-19 levels using a mixed effects model with an unstructured covariance matrix and $log_{10}$ transformed IL-19 concentrations (SAS. Version 9.4 for UNIX; SAS Institute Inc.: Cary, N.C., 2016). Statistical analysis is generated with the ggplot and pROC packages using R version 3.3.3 statistical computing environment (www.R-project.org, Vienna, Austria, 2017).

IL-19 Serum Concentrations in Ps0 Patients Versus Healthy Groups

A study of IL-19 levels in serum of 125 Ps0 patients, pre-treatment, were compared to IL-19 serum levels of 36 healthy volunteer samples. Using an IL-19 assay essentially as described above, with a capture antibody selected from bin 1 (specifically, exemplified IL-19 antibody M_1) and a detection antibody selected from bin 2 (specifically, exemplified IL-19 antibody M_2), serum IL-19 concentrations (pg/ml) of each patient sample is measured. The geometric mean of serum IL-19 concentrations for healthy volunteers (n=36) is measured at 11 pg/mL (with a range of 4 to 51 pg/mL, and a 95% confidence level at less than 21 pg/mL) whereas the geometric mean of serum IL-19 concentrations for Ps0 patients (pre-treatment) (n=112) is measured at 87 pg/mL. Thus, the present invention provides an IL-19 blood-based assay allowing for the diagnosis of Ps0 patients.

Ps0 Study in Anti-IL-17 Treatment Groups

A study of IL-19 levels, in serum of 125 Ps0 patients treated with a therapeutic antibody targeting IL-17, ixekizumab, is performed. The study includes five treatment group doses of: 10 mg (n=24), 25 mg (n=23), 75 mg (n=26), or 150 mg (n=28) of ixekizumab or placebo (n=24). Administration of all treatment doses is subcutaneous, and doses are administered starting at week 0 and every 2 weeks thereafter up to week 16 (inclusive). Using an IL-19 assay as described above, with a capture antibody selected from bin 1 (specifically, exemplified IL-19 antibody M_1]) and a detection antibody selected from bin 5 (specifically, exemplified IL-19 antibody M_2), serum IL-19 concentrations (pg/ml) of each patient is measured at week 0 (pre-treatment dosing), week 2 and week 12. Serum IL-19 concentration levels, percent PASI change and PASI 75 response are provided in Tables 8-10.

As shown, 36 out of 41 (87.8%) patients with a greater than or equal to 5-fold reduction in IL-19 from week 0 to week 2 achieved PASI 75 or greater by week 16 (whereas only 24 of 56 (42.9%) patients with less than a 5-fold reduction in IL19 from week 0 to week 2 achieved a PASI 75 response by week 16. Further, 37 out of 42 (88%) patients with a greater than or equal to 5-fold reduction in IL-19 from week 0 to week 9 achieved PASI 75 or greater by week 12 (whereas only 22 out of 53 (41.5%) patients with less than a 5-fold reduction in IL19 from week 0 to week 16 achieved a PASI 75 response by week 16 (data reflects a drop-out of 2 patients between weeks 2 and 12). For the placebo treatment group, no significant change in IL-19 concentrations were observed during the 16-week trial period.

TABLE 8

IL-19 serum levels (geometric mean) per treatment group.

| Treatment Group | Week 0 (baseline IL-19 pg/mL) | Week 2 (IL-19 pg/mL) | Week 16 (IL-19 pg/mL) |
|---|---|---|---|
| 150 (n = 28) | 87.1 | 13.9 | 11.9 |
| 75 (n = 26) | 86.7 | 11.6 | 9.4 |
| 25 (n = 23) | 89.0 | 22.3 | 13.6 |
| 10 (n = 24) | 111.6 | 45.3 | 57.3 |
| Placebo (n = 24) | 67.4 | 66.7 | 57.2 |

Table 8 provides data showing IL-19 measured in treatment groups over 16 weeks of treatment with placebo or various ixekizumab doses.

TABLE 9

Patients achieving at least PASI 75 at week 16 per treatment group.

| Treatment Group | Week 2 (number of patients achieving at least PASI 75) |
|---|---|
| 150 (n = 24) | 22 |
| 75 (n = 24) | 21 |
| 25 (n = 20) | 16 |
| 10 (n = 19) | 5 |
| Placebo (n = 20) | 1 |

Table 9 provides the the number of patients, per treatment group, achieveing PASI 75 by week 16.

TABLE 10

Assessment of serum IL-19 concentration and PASI at week 16.

| Treatment Group | % of patients with serum IL-19 concentration ≤ 21pg/mL | % patients with serum IL-19 concentration ≤ 21 pg/mL achieving at least PASI 75 | % patients with serum IL-19 concentration ≤ 21 pg/mL not achieving at least PASI 75 |
|---|---|---|---|
| 150 (n = 25) | 92% (23/25) | 95% (19/20) | 5% (1/20) |
| 75 (n = 24) | 91.7% (22/24) | 86.4% (19/22) | 13.6% (3/22) |
| 25 (n = 20) | 70% (14/20) | 92.9% (13/14) | 7.1% (1/14) |
| 10 (n = 19) | 42.1% (8/19) | 62.5% (5/8) | 37.5% (3/8) |
| Placebo (n = 20) | 25% (5/20) | 20% (1/5) | 80% (4/5) |

Table 10 presents correlations of IL-19 serum levels and PASI in psoriasis patients after 16 weeks of placebo or various ixekizumab treatments (21 ng/L indicates the upper limit of the normal range of IL-19 in healthy subjects). It was noted that PASI 100 improvements at 16 weeks were preceded by reduction of circulating IL-19 to near normal concentrations after 2 weeks of treatment.

The data provided in Tables 8-10 demonstrate that the IL-19 assay of the present invention provides a valuable tool for diagnosis and therapeutic prognostication of Ps0 patients treated with IL-17 antibodies.

Ps0 Study in Anti-TNFα Treatment Groups

A study of IL-19 levels, in serum of 35 Ps0 patients that were complete responders when treated with the FDA approved TNFα antagonist, entanercept, is performed. Treatment groups of 50 mg of etanercept (n=35) administered biweekly or placebo are compared. Administration of both treatment groups is subcutaneous. Using an IL-19 assay as described above, with a capture antibody selected from bin 1 (specifically, exemplified IL-19 antibody M_1) and a detection antibody selected from bin 2 (specifically, exemplified IL-19 antibody M_2), serum IL-19 concentrations (pg/ml) of each patient is measured at week 0 (pre-treatment dosing), week 1, week 4 and week 12. IL-19 levels are assessed for prognostic value with PASI improvement at weeks 4 and 12. Serum IL-19 concentration levels are presented in Table 11; prognostic values at week 4 showing correlations of IL-19 serum levels and PASI in psoriasis patients (21 ng/L indicates the upper limit of the normal range of IL-19 in healthy subjects) is presented in Table 12; prognostic values at week 12 P showing correlations of IL-19 serum levels and PASI in psoriasis patients (21 ng/L indicates the upper limit of the normal range of IL-19 in healthy subjects) is presented in Table 13.

TABLE 11

IL-19 (pg/mL) serum levels (geometric mean) per treatment group.

| Treatment Group | Week 0 (baseline) | Week 1 | Week 4 | Week 12 |
|---|---|---|---|---|
| Etanercept (n = 35) | 98.2 | 42.3 | 24.3 | 14.2 |

TABLE 12

Assessment of serum IL-19 concentration and PASI at week 4.

| Treatment Group | % of patients with serum IL-19 concentration ≤ 21 pg/mL | % patients with serum IL-19 concentration ≤ 21 pg/mL achieving at least PASI 75 | % patients with serum IL-19 concentration ≤ 21 pg/mL not achieving at least PASI 75 |
|---|---|---|---|
| Etanercept (n = 160) | 37.9% (44/116) | 22.7% (10/44) | 77.3% (34/44) |

TABLE 13

Assessment of serum IL-19 concentration and PASI at week 12.

| Treatment Group | % of patients with serum IL-19 concentration ≤ 21 pg/mL | % patients with serum IL-19 concentration ≤ 21 pg/mL achieving at least PASI 75 | % patients with serum IL-19 concentration ≤ 21 pg/mL not achieving at least PASI 75 |
|---|---|---|---|
| Etanercept (n = 161) | 42.9% (69/161) | 49.3% (34/69) | 50.7% (35/69) |

As shown above, on average TNF antagonist-treated patients experienced a median reduction in serum IL-19 of greater than 40 (pg/mL) after 1 week and a median reduction in serum IL-19 of grater than 70 (pg/mL) at week 4. The data provided in Tables 11-13 demonstrate that the IL-19 assay of the present invention provides a valuable tool for diagnosis and therapeutic prognostication of Ps0 patients treated with TNFα antibodies.

Ps0 Study in Anti-IL-23 Treatment Groups

A study of IL-19 levels, in serum of Ps0 patients treated with a therapeutic antibody targeting IL-23, mirikizumab, is performed. Eight treatment groups of: 5 mg, 20 mg, 60 mg, 120 mg, 200 mg, 350 mg, and 600 mg of mirikizumab, or placebo, are assessed. Administration of each treatment group, as a single subcutaneous dose, occurs at day 0. Using an IL-19 assay as described above, with a capture antibody selected from bin 1 (specifically, exemplified IL-19 antibody M_1) and a detection antibody selected from bin 2 (specifically, exemplified IL-19 antibody M_2), serum IL-19 concentrations (pg/ml) of each patient is measured between visits 2 and 12. IL-19 levels are also assessed for prognostic value with PASI improvement between visits 2 and 12. Serum IL-19 concentration levels are presented in Table 14; a comparative of serum levels at week 8 is presented in Table 15; and prognostic values at week 8 showing correlations of IL-19 serum levels and PASI in psoriasis patients (21 ng/L indicates the upper limit of the normal range of IL-19 in healthy subjects) are presented in Table 16. Decreases in serum IL-19 correlated with improvement in PASI score demonstrating the IL-19 assay of the present invention provides a valuable tool for diagnosis and therapeutic prognostication of Ps0 patients treated with IL-23 antibodies.

TABLE 14

IL-19 (geometric mean) serum levels per treatment group.

| Treatment Group | Day 1 (baseline) | Day 15 | Day 29 | Day 57 | Day 71 |
|---|---|---|---|---|---|
| 5 (n = 5) | 16.2 | 13.9 | 10.4 | 13.2 | 14.5 |
| 20 (n = 5) | 37.2 | 27.2 | 25.4 | 33.5 | 28.4 |
| 60 (n = 5) | 49.8 | 9.0 | 10.8 | 11.9 | 10.9 |
| 120 (n = 5) | 52.4 | 26.6 | 25.2 | 22.2 | 18.2 |
| 200 (n = 5) | 69.6 | 36.0 | 23.3 | 21.9 | 22.5 |
| 350 (n = 5) | 58.4 | 35.2 | 22.4 | 23.7. | 18.0 |
| 600 (n = 5) | 57.3 | 30.1 | 21.8 | 14.4. | 15.8 |
| placebo (n = 7) | 58.9 | 52.2 | 47.0 | 40.4. | 47.1 |

TABLE 15

IL-19 (geometric mean) serum levels per treatment group.

| Treatment Group | Week 0 (Baseline) | Week 8 (End of induction) |
|---|---|---|
| LY 300 mg (n = 50) | 106.5 | 18.2 |
| Placebo (n = 52) | 158.0 | 154.9 |

TABLE 16

Assessment of serum IL-19 concentration and PASI at week 8.

| Treatment Group | % of patients with serum IL-19 concentration ≤ 21 pg/mL | % patients with serum IL-19 concentration ≤ 21 pg/mL achieving at least PASI 75 | % patients with serum IL-19 concentration ≤ 21 pg/mL not achieving at least PASI 75 |
|---|---|---|---|
| LY 300 mg (n = 48) | 58.3% (28/48) | 71.4% (20/28) | 28.6% (8/28) |
| Placebo (n = 51) | 13.7% (7/51) | 28.6% (2/7) | 71.4% (5/7) |

Ps0 Study in JAK1 and JAK2 Kinase Inhibitor Treatment Groups

A study of IL-19 levels, in serum of Ps0 patients treated with the therapeutic selective JAK1 and JAK2 inhibitor, baricitinib, is performed. Treatment groups of 2 mg, 4 mg, 8 mg, and 10 mg of baricitinib, or placebo, are assessed. Each treatment group is orally administered once daily. Using an IL-19 assay as described above, with a capture antibody selected from bin 1 (specifically, exemplified IL-19 antibody M_1) and a detection antibody selected from bin 2 (specifically, exemplified IL-19 antibody M_2), serum IL-19 concentrations (pg/ml) of each patient is measured at baseline and following each treatment. IL-19 levels are also assessed for prognostic value with PASI improvement.

Serum IL-19 concentration levels are presented in Table 17. PASI prognostic data (at week 12) showing correlations of IL-19 serum levels and PASI in psoriasis patients (21 ng/L indicates the upper limit of the normal range of IL-19 in healthy subjects) are presented in Table 18. The data demonstrates a decreases in serum IL-19 correlates with improvement in PASI score demonstrating the IL-19 assay of the present invention provides a valuable tool for diagnosis and therapeutic prognostication of Ps0 patients treated with JAK1 and JAK2 inhibitors.

TABLE 17

IL-19 serum levels (geometric mean) per treatment group.

| Treatment Group | Week 0 (baseline) | Week 2 | Week 12 |
|---|---|---|---|
| 2 (n = 32) | 182.3 | 98.5 | 64.8 |
| 4 (n = 72) | 134.9 | 70.2 | 60.1 |
| 8 (n = 64) | 177.3 | 67.0 | 47.5 |
| 10 (n = 69) | 110.1 | 39.7 | 25.7 |
| placebo (n = 34) | 116.9 | 131.8 | 95.3 |

TABLE 18

Assessment of serum IL-19 concentration and PASI at week 12.

| Treatment Group | % of patients with serum IL-19 concentration ≤ 21 pg/mL | % patients with serum IL-19 concentration ≤ 21 pg/mL achieving at least PASI 75 | % patients with serum IL-19 concentration ≤ 21 pg/mL not achieving at least PASI 75 |
|---|---|---|---|
| 2 (n = 29) | 13.8% (4/29) | 50% (2/4) | 50% (2/4) |
| 4 (n = 66) | 31.8% (21/66) | 47.6% (10/21) | 52.4% (11/21) |
| 8 (n = 54) | 38.9% (21/54) | 85.7% (18/21) | 14.3% (3/21) |
| 10 (n = 58) | 46.6% (27/58) | 77.8% (21/27) | 22.2% (6/27) |
| Placebo (n = 27) | 14.8% (4/27) | 100% (4/4) | 0% (0/4) |

AD Study in JAK1 and JAK2 Kinase Inhibitor Treatment Groups

A study of IL-19 levels, in serum of 123 patients with moderate-to-sever atopic dermatitis treated with the therapeutic selective JAK1 and JAK2 inhibitor, baricitinib, is performed. Treatment groups of 2 mg and 4 mg of baricitinib, or placebo, are compared. Each treatment group is orally administered once daily. Using an IL-19 assay as described above, with a capture antibody selected from bin 1 (specifically, exemplified IL-19 antibody M_1) and a detection antibody selected from bin 2 (specifically, exemplified IL-19 antibody M_2), serum IL-19 concentrations (pg/ml) of each patient is measured at baseline (pre-treatment) and at weeks 4 and 16. IL-19 levels are assessed for prognostic value with EASI score improvement. Serum IL-19 concentration levels are presented in Table 19; EASI prognostic values (at week 16) showing correlations of IL-19 serum levels in AD patients (21 ng/L indicates the upper limit of the normal range of IL-19 in healthy subjects) are presented in Table 20. The data demonstrates baseline IL-19 concentrations in AD patients were found to be elevated compared to normal (geometric mean of 34 pg/mL in AD patients). The data also demonstrates a decreases in serum IL-19 at weeks 4 and 16 correlates with improvement in EASI score at week 16 demonstrating the IL-19 assay of the present invention provides a valuable tool for diagnosis and therapeutic prognostication of Ps0 patients treated with JAK1 and JAK2 inhibitors.

TABLE 19

IL-19 (geometric mean) serum levels per treatment group.

| Treatment Group | Week 0 (baseline) | Week 4 | Week 16 |
|---|---|---|---|
| 2 (n = 37) | 27.8 | 18.8 | 25.1 |
| 4 (n = 38) | 30.3 | 18.0 | 21.1 |
| placebo (n = 49) | 44.4 | 27.5 | 23.6 |

TABLE 20

Assessment of serum IL-19 concentration and EASI at week 16.

| Treatment Group | % of patients with serum IL-19 concentration ≤ 21 pg/mL | % patients with serum IL-19 concentration ≤ 21 pg/mL achieving at least EASI 75 | % patients with serum IL-19 concentration ≤ 21 pg/mLnot achieving at least EASI 75 |
|---|---|---|---|
| 2 (n = 27) | 51.9% (14/27) | 64.3% (9/14) | 35.7% (5/14) |
| 4 (n = 27) | 63.0% (17/27) | 58.8% (10/17) | 41.2% (7/17) |
| Placebo (n = 28) | 50% (14/28) | 64.3% (9/14) | 35.7% (5/14) |

IL-19 Serum Concentrations in Renal Failure and Diabetes Patient Groups

IL-19 levels are measured in healthy donors (n=20), renal failure patients (n=16), diabetes patients without renal failure (n=20), and diabetes patients with renal failure (n=21). Using an IL-19 assay as described above, with a capture antibody selected from bin 1 (specifically, exemplified IL-19 antibody M_1) and a detection antibody selected from bin 2 (specifically, exemplified IL-19 antibody M_2), baseline serum IL-19 concentrations (pg/ml) of each patient is measured. The data demonstrates markedly elevated IL-19 levels in renal failure patients (40±6 pg/mL), diabetes patients without renal failure (17±3 pg/mL), and diabetes patients with renal failure (46±9 pg/mL) as compared to healthy donors (8±1 pg/mL) IL-19 levels. Thus, the IL-19 assay of the present invention provides a valuable tool for diagnosis and therapeutic prognostication of diabetes and renal failure patients.

PsA Study in Anti-IL-17 Treatment Groups

A study of IL-19 levels, in serum of 309 PsA patients treated with a therapeutic antibody targeting IL-17, ixekizumab, is performed. The study includes three treatment groups: (i.) anti-IL-17 treatment group, administered ixekizumab 160 mg at baseline followed by an 80 mg dose administered every two weeks thereafter for 12 weeks (n=103); (ii.) anti-IL-17 treatment group, administered ixekizumab 160 mg at baseline followed by an 80 mg dose administered every four weeks thereafter for 12 weeks (n=107); or (iii.) placebo (n=105). Administration of all treatment doses is subcutaneous. Using an IL-19 assay as described above, with a capture antibody selected from bin 1 (specifically, exemplified IL-19 antibody M_1) and a detection antibody selected from bin 2 (specifically, exemplified IL-19 antibody M_2), serum IL-19 concentrations (pg/ml) of each patient is measured at week 0 (pre-treatment dosing), week 4 and week 12. Serum IL-19 concentration levels are presented in Table 21; week 4 and 12 PAST prognostic values showing correlations of IL-19 serum levels and PAST in patients (21 ng/L indicates the upper limit of the normal range of IL-19 in healthy subjects) are presented in Tables 22 and 23, respectively.

TABLE 21

IL-19 (geometric mean) serum levels per treatment group.

| Treatment Group | Week 0 (baseline) | Week 4 | Week 12 |
| --- | --- | --- | --- |
| Ixe Q2W (n = 103) | 23.0 | 6.0 | 6.1 |
| Ixe Q4W (n = 107) | 31.3 | 7.6 | 7.3 |
| placebo (n = 105) | 23.7 | 27.0 | 28.4 |

TABLE 22

Assessment of serum IL-19 concentration at week 4 and PASI at week 12.

| Treatment Group | % of patients with serum IL-19 concentration ≤ 21 pg/mL | % patients with serum IL-19 concentration ≤ 21 pg/mL achieving at least PASI 75 | % patients with serum IL-19 concentration ≤ 21 pg/mL not achieving at least PASI 75 |
| --- | --- | --- | --- |
| Ixe Q2W (n = 81) | 97.5% (79/81) | 72.2% (57/79) | 27.8% (22/79) |
| Ixe Q4W (n = 87) | 90.8% (79/87) | 73.4% (58/79) | 26.6% (21/79) |
| Placebo (n = 84) | 46.4% (39/84) | 20.5% (8/39) | 79.5% (31/39) |

TABLE 23

Assessment of serum IL-19 concentration at week 12 and PASI at week 12.

| Treatment Group | % of patients with serum IL-19 concentration ≤ 21 pg/mL | % patients with serum IL-19 concentration ≤ 21 pg/mL achieving at least PASI 75 | % patients with serum IL-19 concentration ≤ 21 pg/mL not achieving at least PASI 75 |
| --- | --- | --- | --- |
| Ixe Q2W (n = 90) | 96.7% (87/90) | 73.1% (57/78) | 26.9% (21/78) |
| Ixe Q4W (n = 93) | 93.5% (87/93) | 74.1% (60/81) | 25.9% (21/81) |
| Placebo (n = 86) | 43.0% (37/86) | 24.3% (9/37) | 75.7% (28/37) |

Table 21 shows baseline IL-19 levels in psoriatic arthritis patients are increased compared to the reference value of healthy volunteers (represented by the shaded grey region). Placebo treatment does not result in significant change in IL-19 over the 12-week time study. However, both ixekizumab treatment groups show lowering of IL-19 to near normal levels after 4 weeks; lowering which is sustained over the 12 week treatment. Tables 22 and 23 show the relationship between IL-19 levels in PsA patients after either 4 or 12 weeks of placebo or ixekizumab treatment groups and the PASI score at 12 weeks. PASI 100 improvements at 12 weeks were correlated with a reduction of circulating IL-19 concentrations to near normal levels, with the majority of the poor PASI responders being in the placebo group. The data provided in Tables 21-23 demonstrate that the IL-19 assay of the present invention provides a valuable tool for diagnosis and therapeutic prognostication of PsA patients treated with IL-17 antibodies.

We claim:

1. A method of detecting IL-19 in a patient sample comprising the steps of:
   contacting the patient sample with a first antibody; and
   detecting a binding of the first antibody to IL-19 in the patient sample,
   wherein, the first antibody comprises a light chain variable region (LCVR) and a heavy chain variable region (HCVR), wherein the LCVR comprises complementarity determining regions (CDRs) LCDR1 set forth in SEQ ID NO. 3, LCDR2 set forth in SEQ ID NO. 4, and LCDR3 set forth in SEQ ID NO. 5 and the HCVR comprises CDRs HCDR1 set forth in SEQ ID NO. 7, HCDR2 set forth in SEQ ID NO. 8 and HCDR3 set forth in SEQ ID NO. 9.

2. The method of claim 1 further comprising the step of:
   contacting the patient sample with a second antibody,
   wherein the second antibody comprises a light chain variable region (LCVR) and a heavy chain variable region (HCVR), wherein the LCVR comprises complementarity determining regions (CDRs) LCDR1 set forth in SEQ ID NO. 11, LCDR2 set forth in SEQ ID NO. 12, and LCDR3 set forth in SEQ ID NO. 13 and the HCVR comprises CDRs HCDR1 set forth in SEQ ID NO. 15, HCDR2 set forth in SEQ ID NO. 16 and HCDR3 set forth in SEQ ID NO. 17.

3. The method of claim 1, wherein the patient sample is plasma.

4. The method of claim 1, wherein the first antibody comprises an IgG1 heavy chain.

5. The method of claim 4, wherein the first antibody further comprises a kappa light chain.

6. The method of claim 2, wherein the second antibody comprises an IgG1 heavy chain.

7. The method of claim 6, wherein the second antibody further comprises a kappa light chain.

8. The method of claim 2, wherein one of the first antibody and the second antibody comprises a detectable label.

9. The method of claim 1, wherein the patient sample is blood.

10. The method of claim 1, wherein the patient sample is serum.

* * * * *

SEQUENCE LISTING

```
<160> NUMBER OF SEQ ID NOS: 313

<210> SEQ ID NO 1
<211> LENGTH: 177
<212> TYPE: PRT
<213> ORGANISM: Homo sapiens

<400> SEQUENCE: 1

Met Lys Leu Gln Cys Val Ser Leu Trp Leu Leu Gly Thr Ile Leu Ile
1               5                   10                  15

Leu Cys Ser Val Asp Asn His Gly Leu Arg Arg Cys Leu Ile Ser Thr
                20                  25                  30

Asp Met His His Ile Glu Glu Ser Phe Gln Glu Ile Lys Arg Ala Ile
            35                  40                  45

Gln Ala Lys Asp Thr Phe Pro Asn Val Thr Ile Leu Ser Thr Leu Glu
        50                  55                  60
```

```
Thr Leu Gln Ile Ile Lys Pro Leu Asp Val Cys Cys Val Thr Lys Asn
 65                  70                  75                  80

Leu Leu Ala Phe Tyr Val Asp Arg Val Phe Lys Asp His Gln Glu Pro
                 85                  90                  95

Asn Pro Lys Ile Leu Arg Lys Ile Ser Ser Ile Ala Asn Ser Phe Leu
            100                 105                 110

Tyr Met Gln Lys Thr Leu Arg Gln Cys Gln Glu Gln Arg Gln Cys His
            115                 120                 125

Cys Arg Gln Glu Ala Thr Asn Ala Thr Arg Val Ile His Asp Asn Tyr
130                 135                 140

Asp Gln Leu Glu Val His Ala Ala Ala Ile Lys Ser Leu Gly Glu Leu
145                 150                 155                 160

Asp Val Phe Leu Ala Trp Ile Asn Lys Asn His Glu Val Met Phe Ser
                165                 170                 175

Ala
```

<210> SEQ ID NO 2
<211> LENGTH: 220
<212> TYPE: PRT
<213> ORGANISM: Artificial Sequence
<220> FEATURE:
<223> OTHER INFORMATION: synthetic construct

<400> SEQUENCE: 2

```
Asp Ile Val Met Thr Gln Ser Pro Ser Ser Leu Ala Met Ser Val Gly
  1               5                  10                  15

Gln Lys Val Thr Met Ser Cys Lys Ser Ser Gln Ser Leu Leu Ser Ser
             20                  25                  30

Tyr Asn Gln Lys Asn Tyr Leu Ala Trp Tyr Gln Gln Lys Pro Gly Gln
         35                  40                  45

Ser Pro Lys Leu Leu Val Tyr Phe Ala Ser Thr Arg Pro Pro Gly Val
 50                  55                  60

Pro Asp Arg Phe Ile Gly Ser Gly Ser Gly Ser Asp Phe Thr Leu Thr
 65                  70                  75                  80

Ile Ser Ser Val Gln Ala Glu Asp Leu Ala Asp Tyr Phe Cys Gln Gln
                 85                  90                  95

His Glu Arg Leu Pro Ile Thr Phe Gly Ala Gly Thr Lys Leu Glu Leu
            100                 105                 110

Lys Arg Ala Asp Ala Ala Pro Thr Val Ser Ile Phe Pro Pro Ser Ser
            115                 120                 125

Glu Gln Leu Thr Ser Gly Gly Ala Ser Val Val Cys Phe Leu Asn Asn
130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
            195                 200                 205

Ser Pro Ile Val Lys Ser Phe Asn Arg Asn Glu Cys
210                 215                 220
```

<210> SEQ ID NO 3
<211> LENGTH: 17
<212> TYPE: PRT

```
<213> ORGANISM: Artificial Sequence
<220> FEATURE:
<223> OTHER INFORMATION: synthetic construct

<400> SEQUENCE: 3

Lys Ser Ser Gln Ser Leu Leu Ser Ser Tyr Asn Gln Lys Asn Tyr Leu
1               5                   10                  15
Ala

<210> SEQ ID NO 4
<211> LENGTH: 7
<212> TYPE: PRT
<213> ORGANISM: Artificial Sequence
<220> FEATURE:
<223> OTHER INFORMATION: synthetic construct

<400> SEQUENCE: 4

Phe Ala Ser Thr Arg Pro Pro
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic construct

<400> SEQUENCE: 5

Gln Gln His Glu Arg Leu Pro Ile Thr
1               5

<210> SEQ ID NO 6
<211> LENGTH: 443
<212> TYPE: PRT
<213> ORGANISM: Artificial Sequence
<220> FEATURE:
<223> OTHER INFORMATION: synthetic construct

<400> SEQUENCE: 6

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Lys Phe Thr Asp Tyr
            20                  25                  30

Phe Val Gly Trp Val Lys Gln Ser His Gly Lys Ser Leu Glu Trp Ile
        35                  40                  45

Gly Tyr Val Asp Pro Glu Asn Gly Tyr Thr Arg Cys Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Asp Tyr Asp Trp Ala Trp Phe Thr Asn Trp Gly Gln Gly
            100                 105                 110

Thr Leu Val Thr Val Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175
```

```
Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 7
<211> LENGTH: 10
<212> TYPE: PRT
<213> ORGANISM: Artificial Sequence
<220> FEATURE:
<223> OTHER INFORMATION: synthetic construct

<400> SEQUENCE: 7

Gly Tyr Lys Phe Thr Asp Tyr Phe Val Gly
1               5                   10

<210> SEQ ID NO 8
<211> LENGTH: 17
<212> TYPE: PRT
<213> ORGANISM: Artificial Sequence
<220> FEATURE:
<223> OTHER INFORMATION: synthetic construct

<400> SEQUENCE: 8

Tyr Val Asp Pro Glu Asn Gly Tyr Thr Arg Cys Asn Gln Lys Phe Lys
1               5                   10                  15

Gly
```

<210> SEQ ID NO 9
<211> LENGTH: 10
<212> TYPE: PRT
<213> ORGANISM: Artificial Sequence
<220> FEATURE:
<223> OTHER INFORMATION: synthetic construct

<400> SEQUENCE: 9

Tyr Asp Tyr Asp Trp Ala Trp Phe Thr Asn
1               5                   10

<210> SEQ ID NO 10
<211> LENGTH: 218
<212> TYPE: PRT
<213> ORGANISM: Artificial Sequence
<220> FEATURE:
<223> OTHER INFORMATION: synthetic construct

<400> SEQUENCE: 10

Asp Ile Val Leu Thr Gln Ser Pro Glu Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Ile His Trp Tyr Gln Gln Lys Pro Gly Gln Pro Pro
        35                  40                  45

Lys Leu Leu Ile Tyr Arg Ala Ser Asn Leu Lys Ser Gly Ile Pro Ala
    50                  55                  60

Arg Phe Ser Gly Arg Gly Ser Arg Thr Asp Phe Thr Leu Thr Ile Asn
65                  70                  75                  80

Pro Val Glu Thr Asp Asp Val Ala Thr Tyr Tyr Cys Gln Gln Ile Asn
                85                  90                  95

Lys Asp Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 11
<211> LENGTH: 15
<212> TYPE: PRT
<213> ORGANISM: Artificial Sequence
<220> FEATURE:
<223> OTHER INFORMATION: synthetic construct

<400> SEQUENCE: 11

Arg Ala Ser Glu Ser Val Asp Asn Tyr Gly Ile Ser Phe Ile His
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: synthetic construct

<400> SEQUENCE: 12

```
Arg Ala Ser Asn Leu Lys Ser
1               5
```

<210> SEQ ID NO 13
<211> LENGTH: 9
<212> TYPE: PRT
<213> ORGANISM: Artificial Sequence
<220> FEATURE:
<223> OTHER INFORMATION: synthetic construct

<400> SEQUENCE: 13

```
Gln Gln Ile Asn Lys Asp Pro Leu Thr
1               5
```

<210> SEQ ID NO 14
<211> LENGTH: 441
<212> TYPE: PRT
<213> ORGANISM: Artificial Sequence
<220> FEATURE:
<223> OTHER INFORMATION: synthetic construct

<400> SEQUENCE: 14

```
Leu Val Gln Leu Gln Gln Ser Asp Ala Glu Leu Val Lys Pro Gly Ala
1               5                   10                  15

Ser Leu Lys Ile Ser Cys Lys Val Ser Gly Tyr Thr Phe Thr Asp His
            20                  25                  30

Ala Leu His Trp Met Lys Gln Arg Pro Glu Gln Gly Leu Glu Trp Ile
        35                  40                  45

Gly Tyr Ile Tyr Pro Arg Asp Gly Ser Thr Lys Tyr Asn Glu Lys Phe
    50                  55                  60

Lys Gly Lys Ala Thr Leu Thr Ala Asp Arg Ser Ser Ser Thr Ala Tyr
65                  70                  75                  80

Met Glu Leu Asn Ser Leu Thr Ser Glu Asp Ser Ala Val Tyr Phe Cys
                85                  90                  95

Ala Arg Gly Trp Asp Phe Ala Met Asp Tyr Trp Gly Gln Gly Thr Ser
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
```

```
                  225                 230                 235                 240

Pro Lys Asp Val Leu Thr Ile Thr Leu Thr Pro Lys Val Thr Cys Val
                245                 250                 255

Val Val Asp Ile Ser Lys Asp Pro Glu Val Gln Phe Ser Trp Phe
            260                 265                 270

Val Asp Asp Val Glu Val His Thr Ala Gln Thr Gln Pro Arg Glu Glu
            275                 280                 285

Gln Phe Asn Ser Thr Phe Arg Ser Val Ser Glu Leu Pro Ile Met His
        290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440

<210> SEQ ID NO 15
<211> LENGTH: 10
<212> TYPE: PRT
<213> ORGANISM: Artificial Sequence
<220> FEATURE:
<223> OTHER INFORMATION: synthetic construct

<400> SEQUENCE: 15

Gly Tyr Thr Phe Thr Asp His Ala Leu His
1               5                   10

<210> SEQ ID NO 16
<211> LENGTH: 17
<212> TYPE: PRT
<213> ORGANISM: Artificial Sequence
<220> FEATURE:
<223> OTHER INFORMATION: synthetic construct

<400> SEQUENCE: 16

Tyr Ile Tyr Pro Arg Asp Gly Ser Thr Lys Tyr Asn Glu Lys Phe Lys
1               5                   10                  15

Gly

<210> SEQ ID NO 17
<211> LENGTH: 8
<212> TYPE: PRT
<213> ORGANISM: Artificial Sequence
<220> FEATURE:
<223> OTHER INFORMATION: synthetic construct

<400> SEQUENCE: 17
```

Gly Trp Asp Phe Ala Met Asp Tyr
1               5

<210> SEQ ID NO 18
<211> LENGTH: 214
<212> TYPE: PRT
<213> ORGANISM: Artificial Sequence
<220> FEATURE:
<223> OTHER INFORMATION: synthetic construct

<400> SEQUENCE: 18

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Phe Cys Leu Gln Tyr Asp Asp Phe Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 19
<211> LENGTH: 11
<212> TYPE: PRT
<213> ORGANISM: Artificial Sequence
<220> FEATURE:
<223> OTHER INFORMATION: synthetic construct

<400> SEQUENCE: 19

Lys Ala Ser Gln Asp Ile Asn Ser Tyr Leu Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: synthetic construct

<400> SEQUENCE: 20

Arg Ala Asn Arg Leu Val Asp

```
1               5
```

<210> SEQ ID NO 21
<211> LENGTH: 9
<212> TYPE: PRT
<213> ORGANISM: Artificial Sequence
<220> FEATURE:
<223> OTHER INFORMATION: synthetic construct

<400> SEQUENCE: 21

```
Leu Gln Tyr Asp Asp Phe Pro Tyr Thr
1               5
```

<210> SEQ ID NO 22
<211> LENGTH: 440
<212> TYPE: PRT
<213> ORGANISM: Artificial Sequence
<220> FEATURE:
<223> OTHER INFORMATION: synthetic construct

<400> SEQUENCE: 22

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Val Trp Ile Asn Thr Tyr Ser Gly Val Pro Thr Tyr Val Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Asp Glu Gly Phe Ala Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285
```

```
Phe Asn Ser Thr Phe Arg Ser Val Ser Glu Leu Pro Ile Met His Gln
        290                 295                 300
Asp Trp Leu Asn Gly Lys Glu Phe Lys Cys Arg Val Asn Ser Ala Ala
305                 310                 315                 320
Phe Pro Ala Pro Ile Glu Lys Thr Ile Ser Lys Thr Lys Gly Arg Pro
                325                 330                 335
Lys Ala Pro Gln Val Tyr Thr Ile Pro Pro Lys Glu Gln Met Ala
                340                 345                 350
Lys Asp Lys Val Ser Leu Thr Cys Met Ile Thr Asp Phe Phe Pro Glu
                355                 360                 365
Asp Ile Thr Val Glu Trp Gln Trp Asn Gly Gln Pro Ala Glu Asn Tyr
        370                 375                 380
Lys Asn Thr Gln Pro Ile Met Asp Thr Asp Gly Ser Tyr Phe Val Tyr
385                 390                 395                 400
Ser Lys Leu Asn Val Gln Lys Ser Asn Trp Glu Ala Gly Asn Thr Phe
                405                 410                 415
Thr Cys Ser Val Leu His Glu Gly Leu His Asn His Thr Glu Lys
                420                 425                 430
Ser Leu Ser His Ser Pro Gly Lys
        435                 440

<210> SEQ ID NO 23
<211> LENGTH: 10
<212> TYPE: PRT
<213> ORGANISM: Artificial Sequence
<220> FEATURE:
<223> OTHER INFORMATION: synthetic construct

<400> SEQUENCE: 23

Gly Tyr Thr Phe Thr Thr Tyr Gly Met Ser
1               5                   10

<210> SEQ ID NO 24
<211> LENGTH: 17
<212> TYPE: PRT
<213> ORGANISM: Artificial Sequence
<220> FEATURE:
<223> OTHER INFORMATION: synthetic construct

<400> SEQUENCE: 24

Trp Ile Asn Thr Tyr Ser Gly Val Pro Thr Tyr Val Asp Asp Phe Lys
1               5                   10                  15
Gly

<210> SEQ ID NO 25
<211> LENGTH: 7
<212> TYPE: PRT
<213> ORGANISM: Artificial Sequence
<220> FEATURE:
<223> OTHER INFORMATION: synthetic construct

<400> SEQUENCE: 25

Arg Asp Glu Gly Phe Ala Tyr
1               5

<210> SEQ ID NO 26
<211> LENGTH: 220
<212> TYPE: PRT
<213> ORGANISM: Artificial Sequence
<220> FEATURE:
<223> OTHER INFORMATION: synthetic construct
```

-continued

```
<400> SEQUENCE: 26

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Ser Ser
            20                  25                  30

Tyr Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Ser Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 27
<211> LENGTH: 17
<212> TYPE: PRT
<213> ORGANISM: Artificial Sequence
<220> FEATURE:
<223> OTHER INFORMATION: synthetic construct

<400> SEQUENCE: 27

Lys Ser Ser Gln Ser Leu Leu Ser Ser Tyr Asn Gln Lys Asn Tyr Leu
1               5                   10                  15

Ala

<210> SEQ ID NO 28
<211> LENGTH: 7
<212> TYPE: PRT
<213> ORGANISM: Artificial Sequence
<220> FEATURE:
<223> OTHER INFORMATION: synthetic construct

<400> SEQUENCE: 28

Phe Ala Ser Thr Arg Glu Ser
1               5

<210> SEQ ID NO 29
<211> LENGTH: 9
<212> TYPE: PRT
<213> ORGANISM: Artificial Sequence
<220> FEATURE:
<223> OTHER INFORMATION: synthetic construct
```

<400> SEQUENCE: 29

Gln Gln His Tyr Ser Thr Pro Leu Thr
1               5

<210> SEQ ID NO 30
<211> LENGTH: 443
<212> TYPE: PRT
<213> ORGANISM: Artificial Sequence
<220> FEATURE:
<223> OTHER INFORMATION: synthetic construct

<400> SEQUENCE: 30

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Phe Ile Asn Pro Tyr Asn Asp Asp Thr Arg Cys Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Asp Gly Tyr Trp Ala Trp Phe Ala Tyr Trp Gly Gln Gly
            100                 105                 110

Thr Leu Val Thr Val Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

```
Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 31
<211> LENGTH: 10
<212> TYPE: PRT
<213> ORGANISM: Artificial Sequence
<220> FEATURE:
<223> OTHER INFORMATION: synthetic construct

<400> SEQUENCE: 31

Gly Tyr Thr Phe Thr Asp Tyr Tyr Met Asn
1               5                   10

<210> SEQ ID NO 32
<211> LENGTH: 17
<212> TYPE: PRT
<213> ORGANISM: Artificial Sequence
<220> FEATURE:
<223> OTHER INFORMATION: synthetic construct

<400> SEQUENCE: 32

Phe Ile Asn Pro Tyr Asn Asp Asp Thr Arg Cys Asn Gln Lys Phe Lys
1               5                   10                  15

Gly

<210> SEQ ID NO 33
<211> LENGTH: 10
<212> TYPE: PRT
<213> ORGANISM: Artificial Sequence
<220> FEATURE:
<223> OTHER INFORMATION: synthetic construct

<400> SEQUENCE: 33

Tyr Asp Gly Tyr Trp Ala Trp Phe Ala Tyr
1               5                   10

<210> SEQ ID NO 34
<211> LENGTH: 111
<212> TYPE: PRT
<213> ORGANISM: Artificial Sequence
<220> FEATURE:
<223> OTHER INFORMATION: synthetic construct

<400> SEQUENCE: 34

Ala Ile Asp Met Thr Gln Thr Pro Ala Ser Val Ser Glu Pro Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
```

```
                    35                  40                  45
Tyr Ser Ala Ser Thr Leu Ala Ser Gly Val Pro Ser Arg Phe Arg Gly
         50                  55                  60

Ser Gly Ser Gly Arg Glu Phe Thr Leu Thr Ile Ser Asp Leu Glu Cys
 65                  70                  75                  80

Ala Asp Ala Ala Thr Tyr Tyr Cys Gln Cys His Tyr His Gly Ser Ser
                 85                  90                  95

Tyr Trp Asp Asn Ser Phe Gly Gly Gly Thr Glu Val Val Val Lys
            100                 105                 110
```

<210> SEQ ID NO 35
<211> LENGTH: 11
<212> TYPE: PRT
<213> ORGANISM: Artificial Sequence
<220> FEATURE:
<223> OTHER INFORMATION: synthetic construct

<400> SEQUENCE: 35

```
Gln Ala Ser Gln Ser Ile Ser Ser Tyr Leu Ala
 1               5                  10
```

<210> SEQ ID NO 36
<211> LENGTH: 7
<212> TYPE: PRT
<213> ORGANISM: Artificial Sequence
<220> FEATURE:
<223> OTHER INFORMATION: synthetic construct

<400> SEQUENCE: 36

```
Ser Ala Ser Thr Leu Ala Ser
 1               5
```

<210> SEQ ID NO 37
<211> LENGTH: 13
<212> TYPE: PRT
<213> ORGANISM: Artificial Sequence
<220> FEATURE:
<223> OTHER INFORMATION: synthetic construct

<400> SEQUENCE: 37

```
Gln Cys His Tyr His Gly Ser Ser Tyr Trp Asp Asn Ser
 1               5                  10
```

<210> SEQ ID NO 38
<211> LENGTH: 120
<212> TYPE: PRT
<213> ORGANISM: Artificial Sequence
<220> FEATURE:
<223> OTHER INFORMATION: synthetic construct

<400> SEQUENCE: 38

```
Gln Gln Leu Glu Glu Ser Gly Gly Gly Leu Val Gln Pro Glu Gly Ser
 1               5                  10                  15

Leu Thr Leu Thr Cys Thr Ala Ser Gly Phe Ser Phe Ser Ser Ser Tyr
                 20                  25                  30

Trp Ile Cys Trp Val Arg Gln Ala Pro Gly Lys Gly Leu Glu Trp Leu
            35                  40                  45

Ala Cys Ile Asp Thr Gly Val Ser Gly Asp Thr Tyr Tyr Ala Asn Trp
         50                  55                  60

Ala Glu Gly Arg Phe Thr Ile Ser Lys Thr Ser Ser Thr Thr Val Thr
 65                  70                  75                  80

Leu Gln Met Thr Ser Leu Thr Ala Ala Asp Thr Ala Thr Tyr Phe Cys
```

```
                    85                  90                  95
Ala Arg Asp Ile Phe Gly Ser Ala Ile Asp Asn Ser Leu Trp Gly Pro
            100                 105                 110

Gly Thr Leu Val Thr Val Ser Ser
        115                 120

<210> SEQ ID NO 39
<211> LENGTH: 11
<212> TYPE: PRT
<213> ORGANISM: Artificial Sequence
<220> FEATURE:
<223> OTHER INFORMATION: synthetic construct

<400> SEQUENCE: 39

Gly Phe Ser Phe Ser Ser Ser Tyr Trp Ile Cys
1               5                   10

<210> SEQ ID NO 40
<211> LENGTH: 18
<212> TYPE: PRT
<213> ORGANISM: Artificial Sequence
<220> FEATURE:
<223> OTHER INFORMATION: synthetic construct

<400> SEQUENCE: 40

Cys Ile Asp Thr Gly Val Ser Gly Asp Thr Tyr Tyr Ala Asn Trp Ala
1               5                   10                  15

Glu Gly

<210> SEQ ID NO 41
<211> LENGTH: 11
<212> TYPE: PRT
<213> ORGANISM: Artificial Sequence
<220> FEATURE:
<223> OTHER INFORMATION: synthetic construct

<400> SEQUENCE: 41

Asp Ile Phe Gly Ser Ala Ile Asp Asn Ser Leu
1               5                   10

<210> SEQ ID NO 42
<211> LENGTH: 112
<212> TYPE: PRT
<213> ORGANISM: Artificial Sequence
<220> FEATURE:
<223> OTHER INFORMATION: synthetic construct

<400> SEQUENCE: 42

Ala Asp Val Val Met Thr Gln Thr Pro Ala Ser Val Glu Ala Ala Val
1               5                   10                  15

Gly Gly Thr Val Thr Ile Lys Cys Gln Ala Ser Glu Ser Ile Gly Asn
            20                  25                  30

Ala Leu Ala Trp Tyr Gln Gln Lys Pro Gly Gln Pro Pro Lys Leu Leu
        35                  40                  45

Ile Tyr Asp Ala Ser Lys Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Gln Cys His Tyr His Gly Ser
                85                  90                  95

Ser Tyr Trp Asp Asn Ser Phe Gly Gly Gly Thr Glu Val Val Val Lys
            100                 105                 110
```

<210> SEQ ID NO 43
<211> LENGTH: 11
<212> TYPE: PRT
<213> ORGANISM: Artificial Sequence
<220> FEATURE:
<223> OTHER INFORMATION: synthetic construct

<400> SEQUENCE: 43

Gln Ala Ser Glu Ser Ile Gly Asn Ala Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: synthetic construct

<400> SEQUENCE: 44

Asp Ala Ser Lys Leu Ala Ser
1               5

<210> SEQ ID NO 45
<211> LENGTH: 13
<212> TYPE: PRT
<213> ORGANISM: Artificial Sequence
<220> FEATURE:
<223> OTHER INFORMATION: synthetic construct

<400> SEQUENCE: 45

Gln Cys His Tyr His Gly Ser Ser Tyr Trp Asp Asn Ser
1               5                   10

<210> SEQ ID NO 46
<211> LENGTH: 120
<212> TYPE: PRT
<213> ORGANISM: Artificial Sequence
<220> FEATURE:
<223> OTHER INFORMATION: synthetic construct

<400> SEQUENCE: 46

Gln Gln Leu Glu Glu Ser Gly Gly Gly Leu Val Gln Pro Glu Gly Ser
1               5                   10                  15

Leu Thr Leu Thr Cys Thr Ala Ser Gly Phe Ser Phe Ser Ser Ser Tyr
            20                  25                  30

Trp Ile Cys Trp Val Arg Gln Ala Pro Gly Lys Gly Leu Glu Trp Leu
        35                  40                  45

Ala Cys Ile Asp Thr Gly Val Ser Gly Asp Thr Tyr Tyr Ala Asn Trp
    50                  55                  60

Ala Lys Gly Arg Phe Thr Ile Ser Lys Thr Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Ile Phe Gly Ser Ala Ile Asp Asn Ser Leu Trp Gly Pro
            100                 105                 110

Gly Thr Leu Val Thr Val Ser Ser
        115                 120

<210> SEQ ID NO 47
<211> LENGTH: 11
<212> TYPE: PRT
<213> ORGANISM: Artificial Sequence

```
<220> FEATURE:
<223> OTHER INFORMATION: synthetic construct

<400> SEQUENCE: 47

Gly Phe Ser Phe Ser Ser Ser Tyr Trp Ile Cys
1               5                   10

<210> SEQ ID NO 48
<211> LENGTH: 18
<212> TYPE: PRT
<213> ORGANISM: Artificial Sequence
<220> FEATURE:
<223> OTHER INFORMATION: synthetic construct

<400> SEQUENCE: 48

Cys Ile Asp Thr Gly Val Ser Gly Asp Thr Tyr Tyr Ala Asn Trp Ala
1               5                   10                  15

Lys Gly

<210> SEQ ID NO 49
<211> LENGTH: 11
<212> TYPE: PRT
<213> ORGANISM: Artificial Sequence
<220> FEATURE:
<223> OTHER INFORMATION: synthetic construct

<400> SEQUENCE: 49

Asp Ile Phe Gly Ser Ala Ile Asp Asn Ser Leu
1               5                   10

<210> SEQ ID NO 50
<211> LENGTH: 112
<212> TYPE: PRT
<213> ORGANISM: Artificial Sequence
<220> FEATURE:
<223> OTHER INFORMATION: synthetic construct

<400> SEQUENCE: 50

Ala Asp Val Val Met Thr Gln Thr Pro Ser Ser Val Glu Ala Ala Val
1               5                   10                  15

Gly Gly Thr Val Thr Ile Lys Cys Gln Ala Ser Gln Ser Ile Gly Ser
                20                  25                  30

Ser Leu Ala Trp Tyr Gln Gln Lys Pro Gly Gln Arg Pro Lys Leu Leu
            35                  40                  45

Ile Tyr Gly Ala Ser Thr Leu Ala Ser Gly Val Pro Ser Arg Phe Lys
        50                  55                  60

Gly Ser Gly Ser Gly Thr Glu Phe Thr Leu Thr Ile Ser Asp Leu Glu
65                  70                  75                  80

Cys Ala Asp Ala Ala Thr Tyr Tyr Cys Gln Cys His Tyr His Gly Ser
                85                  90                  95

Ser Tyr Trp Asp Asn Ser Phe Gly Gly Gly Thr Glu Val Val Val Lys
            100                 105                 110

<210> SEQ ID NO 51
<211> LENGTH: 11
<212> TYPE: PRT
<213> ORGANISM: Artificial Sequence
<220> FEATURE:
<223> OTHER INFORMATION: synthetic construct

<400> SEQUENCE: 51

Gln Ala Ser Gln Ser Ile Gly Ser Ser Leu Ala
1               5                   10
```

<210> SEQ ID NO 52
<211> LENGTH: 7
<212> TYPE: PRT
<213> ORGANISM: Artificial Sequence
<220> FEATURE:
<223> OTHER INFORMATION: synthetic construct

<400> SEQUENCE: 52

Gly Ala Ser Thr Leu Ala Ser
1               5

<210> SEQ ID NO 53
<211> LENGTH: 13
<212> TYPE: PRT
<213> ORGANISM: Artificial Sequence
<220> FEATURE:
<223> OTHER INFORMATION: synthetic construct

<400> SEQUENCE: 53

Gln Cys His Tyr His Gly Ser Ser Tyr Trp Asp Asn Ser
1               5                   10

<210> SEQ ID NO 54
<211> LENGTH: 121
<212> TYPE: PRT
<213> ORGANISM: Artificial Sequence
<220> FEATURE:
<223> OTHER INFORMATION: synthetic construct

<400> SEQUENCE: 54

Gln Cys Gln Ser Leu Glu Glu Ser Gly Gly Leu Val Glu Pro Glu
1               5                   10                  15

Gly Ser Leu Thr Leu Thr Cys Lys Ala Ser Gly Phe Ser Phe Ser Ser
            20                  25                  30

Ser Tyr Trp Ile Cys Trp Val Arg Gln Ala Pro Gly Lys Gly Leu Glu
        35                  40                  45

Trp Ile Ala Cys Thr Asp Thr Phe Ser Gly Asp Thr Tyr Tyr Ala Ser
        50                  55                  60

Trp Ala Lys Gly Arg Phe Thr Ile Ser Lys Thr Ser Thr Thr Val
65                  70                  75                  80

Thr Leu Arg Met Thr Ser Leu Thr Asp Ala Asp Thr Ala Thr Tyr Phe
                85                  90                  95

Cys Ala Arg Asp Ile Phe Gly Thr Ala Val His Ile Ser Leu Trp Gly
                100                 105                 110

Pro Gly Thr Leu Val Thr Val Ser Ser
            115                 120

<210> SEQ ID NO 55
<211> LENGTH: 11
<212> TYPE: PRT
<213> ORGANISM: Artificial Sequence
<220> FEATURE:
<223> OTHER INFORMATION: synthetic construct

<400> SEQUENCE: 55

Gly Phe Ser Phe Ser Ser Ser Tyr Trp Ile Cys
1               5                   10

<210> SEQ ID NO 56
<211> LENGTH: 17
<212> TYPE: PRT
<213> ORGANISM: Artificial Sequence
<220> FEATURE:
<223> OTHER INFORMATION: synthetic construct

<400> SEQUENCE: 56

```
Cys Thr Asp Thr Phe Ser Gly Asp Thr Tyr Tyr Ala Ser Trp Ala Lys
1               5                   10                  15
Gly
```

<210> SEQ ID NO 57
<211> LENGTH: 11
<212> TYPE: PRT
<213> ORGANISM: Artificial Sequence
<220> FEATURE:
<223> OTHER INFORMATION: synthetic construct

<400> SEQUENCE: 57

```
Asp Ile Phe Gly Thr Ala Val His Ile Ser Leu
1               5                   10
```

<210> SEQ ID NO 58
<211> LENGTH: 111
<212> TYPE: PRT
<213> ORGANISM: Artificial Sequence
<220> FEATURE:
<223> OTHER INFORMATION: synthetic construct

<400> SEQUENCE: 58

```
Ala Asp Val Val Met Thr Gln Thr Pro Ser Ser Val Ser Glu Pro Val
1               5                   10                  15

Gly Gly Thr Val Thr Ile Lys Cys Gln Ala Ser Gln Ser Ile Tyr Ser
            20                  25                  30

Tyr Leu Ser Trp Tyr Gln Gln Lys Pro Gly Gln Pro Pro Lys Leu Leu
        35                  40                  45

Ile Tyr Glu Ala Ser Lys Leu Ala Ser Gly Val Pro Ser Arg Phe Lys
    50                  55                  60

Gly Ser Gly Ser Gly Thr Gln Phe Thr Leu Thr Ile Ser Gly Val Glu
65                  70                  75                  80

Cys Ala Asp Ala Ala Thr Tyr Tyr Cys Gln Gln Gly Tyr Ser Ser Ser
                85                  90                  95

Asn Val Asp Asn Thr Phe Gly Gly Gly Thr Glu Val Val Val Thr
            100                 105                 110
```

<210> SEQ ID NO 59
<211> LENGTH: 11
<212> TYPE: PRT
<213> ORGANISM: Artificial Sequence
<220> FEATURE:
<223> OTHER INFORMATION: synthetic construct

<400> SEQUENCE: 59

```
Gln Ala Ser Gln Ser Ile Tyr Ser Tyr Leu Ser
1               5                   10
```

<210> SEQ ID NO 60
<211> LENGTH: 7
<212> TYPE: PRT
<213> ORGANISM: Artificial Sequence
<220> FEATURE:
<223> OTHER INFORMATION: synthetic construct

<400> SEQUENCE: 60

```
Glu Ala Ser Lys Leu Ala Ser
1               5
```

-continued

```
<210> SEQ ID NO 61
<211> LENGTH: 12
<212> TYPE: PRT
<213> ORGANISM: Artificial Sequence
<220> FEATURE:
<223> OTHER INFORMATION: synthetic construct

<400> SEQUENCE: 61

Gln Gln Gly Tyr Ser Ser Ser Asn Val Asp Asn Thr
1               5                   10

<210> SEQ ID NO 62
<211> LENGTH: 119
<212> TYPE: PRT
<213> ORGANISM: Artificial Sequence
<220> FEATURE:
<223> OTHER INFORMATION: synthetic construct

<400> SEQUENCE: 62

Gln Cys Gln Ser Val Glu Glu Ser Gly Gly Arg Leu Val Thr Pro Gly
1               5                   10                  15

Thr Pro Leu Thr Leu Thr Cys Thr Val Ser Gly Ile Asp Leu Ser Ile
            20                  25                  30

Tyr Ala Met Gly Trp Val Arg Gln Ala Pro Gly Lys Gly Leu Glu Tyr
        35                  40                  45

Ile Gly Ile Ile Asp Thr Thr Gly Thr Ala Tyr Tyr Ala Arg Trp Ala
    50                  55                  60

Lys Gly Arg Phe Thr Ile Ser Lys Thr Ser Ala Thr Val Ala Leu Lys
65                  70                  75                  80

Ile Thr Ser Pro Thr Thr Glu Asp Thr Ala Thr Tyr Phe Cys Ala Arg
                85                  90                  95

Asp Ser Gly Ser Leu Tyr Tyr Gly Ser Tyr Ala Leu Trp Gly Pro Gly
            100                 105                 110

Thr Leu Val Thr Val Ser Ser
        115

<210> SEQ ID NO 63
<211> LENGTH: 10
<212> TYPE: PRT
<213> ORGANISM: Artificial Sequence
<220> FEATURE:
<223> OTHER INFORMATION: synthetic construct

<400> SEQUENCE: 63

Gly Ile Asp Leu Ser Ile Tyr Ala Met Gly
1               5                   10

<210> SEQ ID NO 64
<211> LENGTH: 16
<212> TYPE: PRT
<213> ORGANISM: Artificial Sequence
<220> FEATURE:
<223> OTHER INFORMATION: synthetic construct

<400> SEQUENCE: 64

Ile Ile Asp Thr Thr Gly Thr Ala Tyr Tyr Ala Arg Trp Ala Lys Gly
1               5                   10                  15

<210> SEQ ID NO 65
<211> LENGTH: 12
<212> TYPE: PRT
<213> ORGANISM: Artificial Sequence
```

```
<220> FEATURE:
<223> OTHER INFORMATION: synthetic construct

<400> SEQUENCE: 65

Asp Ser Gly Ser Leu Tyr Tyr Gly Ser Tyr Ala Leu
1               5                   10

<210> SEQ ID NO 66
<211> LENGTH: 109
<212> TYPE: PRT
<213> ORGANISM: Artificial Sequence
<220> FEATURE:
<223> OTHER INFORMATION: synthetic construct

<400> SEQUENCE: 66

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Gly
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys Leu Gln Phe Lys Ser Phe Pro
                85                  90                  95

Leu Thr Phe Gly Gln Gly Thr Lys Leu Glu Ile Lys Arg
            100                 105

<210> SEQ ID NO 67
<211> LENGTH: 12
<212> TYPE: PRT
<213> ORGANISM: Artificial Sequence
<220> FEATURE:
<223> OTHER INFORMATION: synthetic construct

<400> SEQUENCE: 67

Arg Ala Ser Gln Ser Ile Ser Ser Gly Tyr Leu Ala
1               5                   10

<210> SEQ ID NO 68
<211> LENGTH: 7
<212> TYPE: PRT
<213> ORGANISM: Artificial Sequence
<220> FEATURE:
<223> OTHER INFORMATION: synthetic construct

<400> SEQUENCE: 68

Gly Ala Ser Ser Arg Ala Thr
1               5

<210> SEQ ID NO 69
<211> LENGTH: 9
<212> TYPE: PRT
<213> ORGANISM: Artificial Sequence
<220> FEATURE:
<223> OTHER INFORMATION: synthetic construct

<400> SEQUENCE: 69

Leu Gln Phe Lys Ser Phe Pro Leu Thr
1               5
```

```
<210> SEQ ID NO 70
<211> LENGTH: 119
<212> TYPE: PRT
<213> ORGANISM: Artificial Sequence
<220> FEATURE:
<223> OTHER INFORMATION: synthetic construct

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Asp Tyr Gly Asp Met Gly Tyr Trp Gly Gln Gly
            100                 105                 110

Thr Leu Val Thr Val Ser Ser
        115

<210> SEQ ID NO 71
<211> LENGTH: 10
<212> TYPE: PRT
<213> ORGANISM: Artificial Sequence
<220> FEATURE:
<223> OTHER INFORMATION: synthetic construct

<400> SEQUENCE: 71

Gly Gly Thr Phe Ser Ser Tyr Ala Ile Ser
1               5                   10

<210> SEQ ID NO 72
<211> LENGTH: 17
<212> TYPE: PRT
<213> ORGANISM: Artificial Sequence
<220> FEATURE:
<223> OTHER INFORMATION: synthetic construct

<400> SEQUENCE: 72

Gly Ile Ile Pro Ile Phe Gly Thr Ala Asn Tyr Ala Gln Lys Phe Gln
1               5                   10                  15

Gly

<210> SEQ ID NO 73
<211> LENGTH: 10
<212> TYPE: PRT
<213> ORGANISM: Artificial Sequence
<220> FEATURE:
<223> OTHER INFORMATION: synthetic construct

<400> SEQUENCE: 73

Asp Gly Gly Asp Tyr Gly Asp Met Gly Tyr
1               5                   10

<210> SEQ ID NO 74
<211> LENGTH: 114
<212> TYPE: PRT
<213> ORGANISM: Artificial Sequence
```

-continued

```
<220> FEATURE:
<223> OTHER INFORMATION: synthetic construct

<400> SEQUENCE: 74

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Arg
            20                  25                  30

Ser Asn Ser Lys Ser Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Gly Ser Phe Gly Pro Gly Thr Lys Val Glu Ile
            100                 105                 110

Lys Arg

<210> SEQ ID NO 75
<211> LENGTH: 17
<212> TYPE: PRT
<213> ORGANISM: Artificial Sequence
<220> FEATURE:
<223> OTHER INFORMATION: synthetic construct

<400> SEQUENCE: 75

Lys Ser Ser Gln Ser Val Leu Tyr Arg Ser Asn Ser Lys Ser Tyr Leu
1               5                   10                  15

Ala

<210> SEQ ID NO 76
<211> LENGTH: 7
<212> TYPE: PRT
<213> ORGANISM: Artificial Sequence
<220> FEATURE:
<223> OTHER INFORMATION: synthetic construct

<400> SEQUENCE: 76

Trp Ala Ser Thr Arg Glu Ser
1               5

<210> SEQ ID NO 77
<211> LENGTH: 9
<212> TYPE: PRT
<213> ORGANISM: Artificial Sequence
<220> FEATURE:
<223> OTHER INFORMATION: synthetic construct

<400> SEQUENCE: 77

Gln Gln Tyr Tyr Ser Thr Pro Gly Ser
1               5

<210> SEQ ID NO 78
<211> LENGTH: 126
<212> TYPE: PRT
<213> ORGANISM: Artificial Sequence
<220> FEATURE:
<223> OTHER INFORMATION: synthetic construct

<400> SEQUENCE: 78
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gln Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Glu Arg Gly Ser Arg Arg Gly Pro Tyr Tyr Tyr Tyr
            100                 105                 110

Met Asp Val Trp Gly Lys Gly Thr Thr Val Thr Val Ser Ser
        115                 120                 125
```

<210> SEQ ID NO 79
<211> LENGTH: 10
<212> TYPE: PRT
<213> ORGANISM: Artificial Sequence
<220> FEATURE:
<223> OTHER INFORMATION: synthetic construct

<400> SEQUENCE: 79

```
Gly Phe Thr Phe Ser Ser Tyr Ala Met Ser
1               5                   10
```

<210> SEQ ID NO 80
<211> LENGTH: 17
<212> TYPE: PRT
<213> ORGANISM: Artificial Sequence
<220> FEATURE:
<223> OTHER INFORMATION: synthetic construct

<400> SEQUENCE: 80

```
Ala Ile Ser Gln Ser Gly Gly Ser Thr Tyr Tyr Ala Asp Ser Val Lys
1               5                   10                  15

Gly
```

<210> SEQ ID NO 81
<211> LENGTH: 17
<212> TYPE: PRT
<213> ORGANISM: Artificial Sequence
<220> FEATURE:
<223> OTHER INFORMATION: synthetic construct

<400> SEQUENCE: 81

```
His Pro Glu Arg Gly Ser Arg Arg Gly Pro Tyr Tyr Tyr Tyr Met Asp
1               5                   10                  15

Val
```

<210> SEQ ID NO 82
<211> LENGTH: 109
<212> TYPE: PRT
<213> ORGANISM: Artificial Sequence
<220> FEATURE:
<223> OTHER INFORMATION: synthetic construct

<400> SEQUENCE: 82

```
Asp Ile Gln Leu Thr Gln Ser Pro Ser Ser Leu Ser Ala Ser Leu Gly
1               5                   10                  15
```

```
Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Tyr Asp Tyr Ser Pro
                85                  90                  95

Trp Ala Phe Gly Gln Gly Thr Lys Leu Glu Ile Lys Arg
            100                 105

<210> SEQ ID NO 83
<211> LENGTH: 11
<212> TYPE: PRT
<213> ORGANISM: Artificial Sequence
<220> FEATURE:
<223> OTHER INFORMATION: synthetic construct

<400> SEQUENCE: 83

Arg Ala Ser Gln Gly Ile Ser Ser Trp Leu Ala
1               5                   10

<210> SEQ ID NO 84
<211> LENGTH: 7
<212> TYPE: PRT
<213> ORGANISM: Artificial Sequence
<220> FEATURE:
<223> OTHER INFORMATION: synthetic construct

<400> SEQUENCE: 84

Ala Ala Ser Thr Leu Gln Ser
1               5

<210> SEQ ID NO 85
<211> LENGTH: 10
<212> TYPE: PRT
<213> ORGANISM: Artificial Sequence
<220> FEATURE:
<223> OTHER INFORMATION: synthetic construct

<400> SEQUENCE: 85

Gln Gln Tyr Tyr Asp Tyr Ser Pro Trp Ala
1               5                   10

<210> SEQ ID NO 86
<211> LENGTH: 125
<212> TYPE: PRT
<213> ORGANISM: Artificial Sequence
<220> FEATURE:
<223> OTHER INFORMATION: synthetic construct

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Leu Ser Leu Leu Tyr Tyr Asp Leu Ser Glu Asn Tyr Phe
        100                 105                 110

Asp Tyr Trp Gly Gln Gly Thr Thr Val Thr Val Ser Ser
        115                 120                 125

<210> SEQ ID NO 87
<211> LENGTH: 10
<212> TYPE: PRT
<213> ORGANISM: Artificial Sequence
<220> FEATURE:
<223> OTHER INFORMATION: synthetic construct

<400> SEQUENCE: 87

Gly Phe Thr Phe Ser Ser Tyr Ala Met Ser
1               5                   10

<210> SEQ ID NO 88
<211> LENGTH: 17
<212> TYPE: PRT
<213> ORGANISM: Artificial Sequence
<220> FEATURE:
<223> OTHER INFORMATION: synthetic construct

<400> SEQUENCE: 88

Ala Ile Ser Gly Ser Gly Gly Ser Thr Tyr Tyr Ala Asp Ser Val Lys
1               5                   10                  15

Gly

<210> SEQ ID NO 89
<211> LENGTH: 16
<212> TYPE: PRT
<213> ORGANISM: Artificial Sequence
<220> FEATURE:
<223> OTHER INFORMATION: synthetic construct

<400> SEQUENCE: 89

Gly Leu Ser Leu Leu Tyr Tyr Asp Leu Ser Glu Asn Tyr Phe Asp Tyr
1               5                   10                  15

<210> SEQ ID NO 90
<211> LENGTH: 11
<212> TYPE: PRT
<213> ORGANISM: Artificial Sequence
<220> FEATURE:
<223> OTHER INFORMATION: synthetic construct

<400> SEQUENCE: 90

Gln Ala Ser Gln Ser Ile Tyr Ser Tyr Leu Ser
1               5                   10

<210> SEQ ID NO 91
<211> LENGTH: 7
<212> TYPE: PRT
<213> ORGANISM: Artificial Sequence
<220> FEATURE:
<223> OTHER INFORMATION: synthetic construct

<400> SEQUENCE: 91

Glu Ala Ser Lys Leu Ala Ser
1               5

<210> SEQ ID NO 92
<211> LENGTH: 12
<212> TYPE: PRT
<213> ORGANISM: Artificial Sequence
<220> FEATURE:
<223> OTHER INFORMATION: synthetic construct

<400> SEQUENCE: 92

Gln Gln Gly Tyr Ser Ser Ser Asn Val Asp Asn Thr
1               5                   10

<210> SEQ ID NO 93
<211> LENGTH: 10
<212> TYPE: PRT
<213> ORGANISM: Artificial Sequence
<220> FEATURE:
<223> OTHER INFORMATION: synthetic construct

<400> SEQUENCE: 93

Gly Ile Asp Leu Ser Ile Tyr Ala Met Gly
1               5                   10

<210> SEQ ID NO 94
<211> LENGTH: 16
<212> TYPE: PRT
<213> ORGANISM: Artificial Sequence
<220> FEATURE:
<223> OTHER INFORMATION: synthetic construct

<400> SEQUENCE: 94

Ile Ile Asp Thr Thr Gly Thr Ala Tyr Tyr Ala Arg Trp Ala Lys Gly
1               5                   10                  15

<210> SEQ ID NO 95
<211> LENGTH: 12
<212> TYPE: PRT
<213> ORGANISM: Artificial Sequence
<220> FEATURE:
<223> OTHER INFORMATION: synthetic construct

<400> SEQUENCE: 95

Asp Ser Gly Ser Leu Tyr Tyr Gly Ser Tyr Ala Leu
1               5                   10

<210> SEQ ID NO 96
<211> LENGTH: 11
<212> TYPE: PRT
<213> ORGANISM: Artificial Sequence
<220> FEATURE:
<223> OTHER INFORMATION: synthetic construct

<400> SEQUENCE: 96

Gln Ala Ser Glu Ser Ile Tyr Ser Ser Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: synthetic construct

<400> SEQUENCE: 97

Gly Ala Ser Thr Leu Ala Ser
1               5

```
<210> SEQ ID NO 98
<211> LENGTH: 13
<212> TYPE: PRT
<213> ORGANISM: Artificial Sequence
<220> FEATURE:
<223> OTHER INFORMATION: synthetic construct

<400> SEQUENCE: 98

Gln Cys His Tyr His Gly Ser Ser Tyr Trp Asp Asn Ser
1               5                   10

<210> SEQ ID NO 99
<211> LENGTH: 11
<212> TYPE: PRT
<213> ORGANISM: Artificial Sequence
<220> FEATURE:
<223> OTHER INFORMATION: synthetic construct

<400> SEQUENCE: 99

Gly Phe Ser Phe Ser Ser Ser Tyr Trp Ile Cys
1               5                   10

<210> SEQ ID NO 100
<211> LENGTH: 17
<212> TYPE: PRT
<213> ORGANISM: Artificial Sequence
<220> FEATURE:
<223> OTHER INFORMATION: synthetic construct

<400> SEQUENCE: 100

Cys Thr Asp Thr Phe Ser Gly Asp Thr Tyr Tyr Ala Ser Trp Ala Lys
1               5                   10                  15

Gly

<210> SEQ ID NO 101
<211> LENGTH: 11
<212> TYPE: PRT
<213> ORGANISM: Artificial Sequence
<220> FEATURE:
<223> OTHER INFORMATION: synthetic construct

<400> SEQUENCE: 101

Asp Ile Phe Gly Thr Ala Val His Ile Ser Leu
1               5                   10

<210> SEQ ID NO 102
<211> LENGTH: 11
<212> TYPE: PRT
<213> ORGANISM: Artificial Sequence
<220> FEATURE:
<223> OTHER INFORMATION: synthetic construct

<400> SEQUENCE: 102

Gln Ala Ser Glu Ser Ile Tyr Ser Ser Leu Ala
1               5                   10

<210> SEQ ID NO 103
<211> LENGTH: 7
<212> TYPE: PRT
<213> ORGANISM: Artificial Sequence
<220> FEATURE:
<223> OTHER INFORMATION: synthetic construct

<400> SEQUENCE: 103

Gly Ala Ser Thr Leu Ala Ser
1               5
```

```
<210> SEQ ID NO 104
<211> LENGTH: 13
<212> TYPE: PRT
<213> ORGANISM: Artificial Sequence
<220> FEATURE:
<223> OTHER INFORMATION: synthetic construct

<400> SEQUENCE: 104

Gln Cys His Tyr His Gly Ser Ser Tyr Trp Asp Asn Ser
1               5                   10

<210> SEQ ID NO 105
<211> LENGTH: 11
<212> TYPE: PRT
<213> ORGANISM: Artificial Sequence
<220> FEATURE:
<223> OTHER INFORMATION: synthetic construct

<400> SEQUENCE: 105

Gly Phe Ser Phe Ser Ser Ser Tyr Trp Ile Cys
1               5                   10

<210> SEQ ID NO 106
<211> LENGTH: 17
<212> TYPE: PRT
<213> ORGANISM: Artificial Sequence
<220> FEATURE:
<223> OTHER INFORMATION: synthetic construct

<400> SEQUENCE: 106

Cys Thr Asp Thr Phe Ser Gly Asp Thr Tyr Tyr Ala Ser Trp Ala Lys
1               5                   10                  15

Gly

<210> SEQ ID NO 107
<211> LENGTH: 11
<212> TYPE: PRT
<213> ORGANISM: Artificial Sequence
<220> FEATURE:
<223> OTHER INFORMATION: synthetic construct

<400> SEQUENCE: 107

Asp Ile Phe Gly Thr Ala Val His Ile Ser Leu
1               5                   10

<210> SEQ ID NO 108
<211> LENGTH: 11
<212> TYPE: PRT
<213> ORGANISM: Artificial Sequence
<220> FEATURE:
<223> OTHER INFORMATION: synthetic construct

<400> SEQUENCE: 108

Gln Ala Ser Gln Ser Ile Gly Ser Ser Leu Ala
1               5                   10

<210> SEQ ID NO 109
<211> LENGTH: 7
<212> TYPE: PRT
<213> ORGANISM: Artificial Sequence
<220> FEATURE:
<223> OTHER INFORMATION: synthetic construct

<400> SEQUENCE: 109

Gly Ala Ser Thr Leu Ala Ser
```

<210> SEQ ID NO 110
<211> LENGTH: 13
<212> TYPE: PRT
<213> ORGANISM: Artificial Sequence
<220> FEATURE:
<223> OTHER INFORMATION: synthetic construct

<400> SEQUENCE: 110

Gln Cys His Tyr His Gly Ser Ser Tyr Trp Asp Asn Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: synthetic construct

<400> SEQUENCE: 111

Gly Phe Ser Phe Ser Ser Ser Tyr Trp Ile Cys
1               5                   10

<210> SEQ ID NO 112
<211> LENGTH: 17
<212> TYPE: PRT
<213> ORGANISM: Artificial Sequence
<220> FEATURE:
<223> OTHER INFORMATION: synthetic construct

<400> SEQUENCE: 112

Cys Thr Asp Thr Phe Ser Gly Asp Thr Tyr Tyr Ala Ser Trp Ala Lys
1               5                   10                  15

Gly

<210> SEQ ID NO 113
<211> LENGTH: 11
<212> TYPE: PRT
<213> ORGANISM: Artificial Sequence
<220> FEATURE:
<223> OTHER INFORMATION: synthetic construct

<400> SEQUENCE: 113

Asp Ile Phe Gly Thr Ala Val His Ile Ser Leu
1               5                   10

<210> SEQ ID NO 114
<211> LENGTH: 11
<212> TYPE: PRT
<213> ORGANISM: Artificial Sequence
<220> FEATURE:
<223> OTHER INFORMATION: synthetic construct

<400> SEQUENCE: 114

Gln Ala Ser Glu Ser Ile Tyr Ser Ser Leu Ala
1               5                   10

<210> SEQ ID NO 115
<211> LENGTH: 7
<212> TYPE: PRT
<213> ORGANISM: Artificial Sequence
<220> FEATURE:
<223> OTHER INFORMATION: synthetic construct

<400> SEQUENCE: 115

Gly Ala Ser Thr Leu Ala Ser
1               5

<210> SEQ ID NO 116
<211> LENGTH: 13
<212> TYPE: PRT
<213> ORGANISM: Artificial Sequence
<220> FEATURE:
<223> OTHER INFORMATION: synthetic construct

<400> SEQUENCE: 116

Gln Cys His Tyr His Gly Ser Ser Tyr Trp Asp Asn Ser
1               5                   10

<210> SEQ ID NO 117
<211> LENGTH: 11
<212> TYPE: PRT
<213> ORGANISM: Artificial Sequence
<220> FEATURE:
<223> OTHER INFORMATION: synthetic construct

<400> SEQUENCE: 117

Gly Phe Ser Phe Ser Ser Ser Tyr Trp Ile Cys
1               5                   10

<210> SEQ ID NO 118
<211> LENGTH: 17
<212> TYPE: PRT
<213> ORGANISM: Artificial Sequence
<220> FEATURE:
<223> OTHER INFORMATION: synthetic construct

<400> SEQUENCE: 118

Cys Thr Asp Thr Phe Ser Gly Asp Thr Tyr Tyr Ala Ser Trp Ala Lys
1               5                   10                  15

Gly

<210> SEQ ID NO 119
<211> LENGTH: 11
<212> TYPE: PRT
<213> ORGANISM: Artificial Sequence
<220> FEATURE:
<223> OTHER INFORMATION: synthetic construct

<400> SEQUENCE: 119

Asp Ile Phe Gly Thr Ala Val His Ile Ser Leu
1               5                   10

<210> SEQ ID NO 120
<211> LENGTH: 11
<212> TYPE: PRT
<213> ORGANISM: Artificial Sequence
<220> FEATURE:
<223> OTHER INFORMATION: synthetic construct

<400> SEQUENCE: 120

Gln Ala Ser Gln Ser Ile Ser Ser Tyr Leu Ala
1               5                   10

<210> SEQ ID NO 121
<211> LENGTH: 7
<212> TYPE: PRT
<213> ORGANISM: Artificial Sequence
<220> FEATURE:
<223> OTHER INFORMATION: synthetic construct

<400> SEQUENCE: 121

```
Gly Ala Ser Thr Leu Ala Ser
1               5

<210> SEQ ID NO 122
<211> LENGTH: 13
<212> TYPE: PRT
<213> ORGANISM: Artificial Sequence
<220> FEATURE:
<223> OTHER INFORMATION: synthetic construct

<400> SEQUENCE: 122

Gln Cys His Tyr His Gly Ser Ser Tyr Trp Asp Asn Ser
1               5                   10

<210> SEQ ID NO 123
<211> LENGTH: 11
<212> TYPE: PRT
<213> ORGANISM: Artificial Sequence
<220> FEATURE:
<223> OTHER INFORMATION: synthetic construct

<400> SEQUENCE: 123

Gly Phe Ser Phe Ser Ser Ser Tyr Trp Ile Cys
1               5                   10

<210> SEQ ID NO 124
<211> LENGTH: 17
<212> TYPE: PRT
<213> ORGANISM: Artificial Sequence
<220> FEATURE:
<223> OTHER INFORMATION: synthetic construct

<400> SEQUENCE: 124

Cys Thr Asp Thr Phe Ser Gly Asp Thr Tyr Tyr Ala Ser Trp Ala Lys
1               5                   10                  15

Gly

<210> SEQ ID NO 125
<211> LENGTH: 11
<212> TYPE: PRT
<213> ORGANISM: Artificial Sequence
<220> FEATURE:
<223> OTHER INFORMATION: synthetic construct

<400> SEQUENCE: 125

Asp Ile Phe Gly Thr Ala Val His Ile Ser Leu
1               5                   10

<210> SEQ ID NO 126
<211> LENGTH: 11
<212> TYPE: PRT
<213> ORGANISM: Artificial Sequence
<220> FEATURE:
<223> OTHER INFORMATION: synthetic construct

<400> SEQUENCE: 126

Gln Ala Ser Gln Ser Ile Ser Ser Tyr Leu Ala
1               5                   10

<210> SEQ ID NO 127
<211> LENGTH: 7
<212> TYPE: PRT
<213> ORGANISM: Artificial Sequence
<220> FEATURE:
<223> OTHER INFORMATION: synthetic construct
```

<400> SEQUENCE: 127

Gly Ala Ser Thr Leu Ala Ser
1               5

<210> SEQ ID NO 128
<211> LENGTH: 14
<212> TYPE: PRT
<213> ORGANISM: Artificial Sequence
<220> FEATURE:
<223> OTHER INFORMATION: synthetic construct

<400> SEQUENCE: 128

Gln Ser Ala Val Tyr Ser Ser Ser Gly Tyr Gly Val Pro
1               5                   10

<210> SEQ ID NO 129
<211> LENGTH: 10
<212> TYPE: PRT
<213> ORGANISM: Artificial Sequence
<220> FEATURE:
<223> OTHER INFORMATION: synthetic construct

<400> SEQUENCE: 129

Gly Phe Ser Leu Ser Ser Tyr Asp Met Ser
1               5                   10

<210> SEQ ID NO 130
<211> LENGTH: 16
<212> TYPE: PRT
<213> ORGANISM: Artificial Sequence
<220> FEATURE:
<223> OTHER INFORMATION: synthetic construct

<400> SEQUENCE: 130

Ile Ile Asp Ser Ile Gly Ser Ile Trp Tyr Ala Asn Trp Ala Lys Gly
1               5                   10                  15

<210> SEQ ID NO 131
<211> LENGTH: 11
<212> TYPE: PRT
<213> ORGANISM: Artificial Sequence
<220> FEATURE:
<223> OTHER INFORMATION: synthetic construct

<400> SEQUENCE: 131

Glu Ser Gly Pro Ile Asn Thr Asp Tyr Asp Leu
1               5                   10

<210> SEQ ID NO 132
<211> LENGTH: 13
<212> TYPE: PRT
<213> ORGANISM: Artificial Sequence
<220> FEATURE:
<223> OTHER INFORMATION: synthetic construct

<400> SEQUENCE: 132

Gln Thr Ser Glu Ser Phe Tyr Ser Asn Asn Ile Leu Ser
1               5                   10

<210> SEQ ID NO 133
<211> LENGTH: 7
<212> TYPE: PRT
<213> ORGANISM: Artificial Sequence
<220> FEATURE:
<223> OTHER INFORMATION: synthetic construct

<400> SEQUENCE: 133

Glu Ala Ser Lys Leu Ala Ser
1               5

<210> SEQ ID NO 134
<211> LENGTH: 12
<212> TYPE: PRT
<213> ORGANISM: Artificial Sequence
<220> FEATURE:
<223> OTHER INFORMATION: synthetic construct

<400> SEQUENCE: 134

Gln Ser Ala Ile Tyr Asp Gly Ser Tyr Ile Val Thr
1               5                   10

<210> SEQ ID NO 135
<211> LENGTH: 10
<212> TYPE: PRT
<213> ORGANISM: Artificial Sequence
<220> FEATURE:
<223> OTHER INFORMATION: synthetic construct

<400> SEQUENCE: 135

Gly Phe Ser Leu Ser Ser Tyr Asp Met Ser
1               5                   10

<210> SEQ ID NO 136
<211> LENGTH: 16
<212> TYPE: PRT
<213> ORGANISM: Artificial Sequence
<220> FEATURE:
<223> OTHER INFORMATION: synthetic construct

<400> SEQUENCE: 136

Ile Ile Asp Ser Ile Gly Ser Ile Trp Tyr Ala Asn Trp Ala Lys Gly
1               5                   10                  15

<210> SEQ ID NO 137
<211> LENGTH: 11
<212> TYPE: PRT
<213> ORGANISM: Artificial Sequence
<220> FEATURE:
<223> OTHER INFORMATION: synthetic construct

<400> SEQUENCE: 137

Glu Ser Gly Pro Ile Asn Thr Asp Tyr Asp Leu
1               5                   10

<210> SEQ ID NO 138
<211> LENGTH: 11
<212> TYPE: PRT
<213> ORGANISM: Artificial Sequence
<220> FEATURE:
<223> OTHER INFORMATION: synthetic construct

<400> SEQUENCE: 138

Gln Ala Ser Gln Ser Ile Ser Ser Tyr Leu Ala
1               5                   10

<210> SEQ ID NO 139
<211> LENGTH: 7
<212> TYPE: PRT
<213> ORGANISM: Artificial Sequence
<220> FEATURE:
<223> OTHER INFORMATION: synthetic construct

<400> SEQUENCE: 139

Gly Ala Ser Thr Leu Ala Ser
1               5

<210> SEQ ID NO 140
<211> LENGTH: 14
<212> TYPE: PRT
<213> ORGANISM: Artificial Sequence
<220> FEATURE:
<223> OTHER INFORMATION: synthetic construct

<400> SEQUENCE: 140

Gln Ser Ala Val Tyr Ser Ser Ser Gly Tyr Gly Val Pro
1               5                   10

<210> SEQ ID NO 141
<211> LENGTH: 10
<212> TYPE: PRT
<213> ORGANISM: Artificial Sequence
<220> FEATURE:
<223> OTHER INFORMATION: synthetic construct

<400> SEQUENCE: 141

Gly Phe Ser Leu Ser Ser Tyr Asp Met Ser
1               5                   10

<210> SEQ ID NO 142
<211> LENGTH: 16
<212> TYPE: PRT
<213> ORGANISM: Artificial Sequence
<220> FEATURE:
<223> OTHER INFORMATION: synthetic construct

<400> SEQUENCE: 142

Ile Ile Asp Ser Ile Gly Ser Ile Trp Tyr Ala Asn Trp Ala Lys Gly
1               5                   10                  15

<210> SEQ ID NO 143
<211> LENGTH: 11
<212> TYPE: PRT
<213> ORGANISM: Artificial Sequence
<220> FEATURE:
<223> OTHER INFORMATION: synthetic construct

<400> SEQUENCE: 143

Glu Ser Gly Pro Ile Asn Thr Asp Tyr Asp Leu
1               5                   10

<210> SEQ ID NO 144
<211> LENGTH: 11
<212> TYPE: PRT
<213> ORGANISM: Artificial Sequence
<220> FEATURE:
<223> OTHER INFORMATION: synthetic construct

<400> SEQUENCE: 144

Gln Ala Ser Gln Ser Ile Ser Ser Tyr Leu Ala
1               5                   10

<210> SEQ ID NO 145
<211> LENGTH: 7
<212> TYPE: PRT
<213> ORGANISM: Artificial Sequence
<220> FEATURE:
<223> OTHER INFORMATION: synthetic construct

<400> SEQUENCE: 145

Gly Ala Ser Thr Leu Ala Ser

```
<210> SEQ ID NO 146
<211> LENGTH: 14
<212> TYPE: PRT
<213> ORGANISM: Artificial Sequence
<220> FEATURE:
<223> OTHER INFORMATION: synthetic construct

<400> SEQUENCE: 146

Gln Ser Ala Val Tyr Ser Ser Ser Ser Gly Tyr Gly Val Pro
1               5                   10

<210> SEQ ID NO 147
<211> LENGTH: 10
<212> TYPE: PRT
<213> ORGANISM: Artificial Sequence
<220> FEATURE:
<223> OTHER INFORMATION: synthetic construct

<400> SEQUENCE: 147

Gly Phe Ser Leu Ser Ser Tyr Asp Met Ser
1               5                   10

<210> SEQ ID NO 148
<211> LENGTH: 16
<212> TYPE: PRT
<213> ORGANISM: Artificial Sequence
<220> FEATURE:
<223> OTHER INFORMATION: synthetic construct

<400> SEQUENCE: 148

Ile Ile Asp Ser Ile Gly Ser Ile Trp Tyr Ala Asn Trp Ala Lys Gly
1               5                   10                  15

<210> SEQ ID NO 149
<211> LENGTH: 11
<212> TYPE: PRT
<213> ORGANISM: Artificial Sequence
<220> FEATURE:
<223> OTHER INFORMATION: synthetic construct

<400> SEQUENCE: 149

Glu Ser Gly Pro Ile Asn Thr Asp Tyr Asp Leu
1               5                   10

<210> SEQ ID NO 150
<211> LENGTH: 11
<212> TYPE: PRT
<213> ORGANISM: Artificial Sequence
<220> FEATURE:
<223> OTHER INFORMATION: synthetic construct

<400> SEQUENCE: 150

Gln Ala Ser Glu Ser Ile Ser Ser Tyr Leu Ala
1               5                   10

<210> SEQ ID NO 151
<211> LENGTH: 7
<212> TYPE: PRT
<213> ORGANISM: Artificial Sequence
<220> FEATURE:
<223> OTHER INFORMATION: synthetic construct

<400> SEQUENCE: 151

Gly Ala Ser Thr Leu Ala Ser
1               5
```

```
<210> SEQ ID NO 152
<211> LENGTH: 10
<212> TYPE: PRT
<213> ORGANISM: Artificial Sequence
<220> FEATURE:
<223> OTHER INFORMATION: synthetic construct

<400> SEQUENCE: 152

Gln Gly Tyr Phe Gly Asp Tyr Ile Tyr Gly
1               5                   10

<210> SEQ ID NO 153
<211> LENGTH: 10
<212> TYPE: PRT
<213> ORGANISM: Artificial Sequence
<220> FEATURE:
<223> OTHER INFORMATION: synthetic construct

<400> SEQUENCE: 153

Gly Phe Ser Leu Thr Ser Tyr Ala Met Ser
1               5                   10

<210> SEQ ID NO 154
<211> LENGTH: 16
<212> TYPE: PRT
<213> ORGANISM: Artificial Sequence
<220> FEATURE:
<223> OTHER INFORMATION: synthetic construct

<400> SEQUENCE: 154

Ile Ile Gly Ser Pro Gly Thr Thr Gly Tyr Ala Thr Trp Ala Lys Gly
1               5                   10                  15

<210> SEQ ID NO 155
<211> LENGTH: 9
<212> TYPE: PRT
<213> ORGANISM: Artificial Sequence
<220> FEATURE:
<223> OTHER INFORMATION: synthetic construct

<400> SEQUENCE: 155

Gly Trp Phe Tyr Tyr Gly Met Ala Leu
1               5

<210> SEQ ID NO 156
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 156

Pro Xaa Gln Glu His Leu Thr Pro
1               5

<210> SEQ ID NO 157
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
```

```
-continued

<222> LOCATION: (7)..(7)
<223> OTHER INFORMATION: Xaa can be any naturally occurring amino acid

<400> SEQUENCE: 157

Gly Ala Ser Thr Leu Ala Xaa
1               5

<210> SEQ ID NO 158
<211> LENGTH: 10
<212> TYPE: PRT
<213> ORGANISM: Artificial Sequence
<220> FEATURE:
<223> OTHER INFORMATION: synthetic construct

<400> SEQUENCE: 158

Gln Gly Tyr Phe Gly Asp Tyr Ile Tyr Gly
1               5                   10

<210> SEQ ID NO 159
<211> LENGTH: 10
<212> TYPE: PRT
<213> ORGANISM: Artificial Sequence
<220> FEATURE:
<223> OTHER INFORMATION: synthetic construct

<400> SEQUENCE: 159

Gly Phe Ser Leu Thr Ser Tyr Ala Met Ser
1               5                   10

<210> SEQ ID NO 160
<211> LENGTH: 16
<212> TYPE: PRT
<213> ORGANISM: Artificial Sequence
<220> FEATURE:
<223> OTHER INFORMATION: synthetic construct

<400> SEQUENCE: 160

Ile Ile Gly Ser Pro Gly Thr Thr Gly Tyr Ala Thr Trp Ala Lys Gly
1               5                   10                  15

<210> SEQ ID NO 161
<211> LENGTH: 9
<212> TYPE: PRT
<213> ORGANISM: Artificial Sequence
<220> FEATURE:
<223> OTHER INFORMATION: synthetic construct

<400> SEQUENCE: 161

Gly Trp Phe Tyr Tyr Gly Met Ala Leu
1               5

<210> SEQ ID NO 162
<211> LENGTH: 11
<212> TYPE: PRT
<213> ORGANISM: Artificial Sequence
<220> FEATURE:
<223> OTHER INFORMATION: synthetic construct

<400> SEQUENCE: 162

Gln Ala Ser Glu Ser Ile Ser Ser Tyr Leu Ala
1               5                   10

<210> SEQ ID NO 163
<211> LENGTH: 7
<212> TYPE: PRT
<213> ORGANISM: Artificial Sequence
<220> FEATURE:
```

```
<223> OTHER INFORMATION: synthetic construct

<400> SEQUENCE: 163

Gly Ala Ser Thr Leu Ala Ser
1               5

<210> SEQ ID NO 164
<211> LENGTH: 10
<212> TYPE: PRT
<213> ORGANISM: Artificial Sequence
<220> FEATURE:
<223> OTHER INFORMATION: synthetic construct

<400> SEQUENCE: 164

Gln Gly Tyr Phe Gly Asp Tyr Ile Tyr Gly
1               5                   10

<210> SEQ ID NO 165
<211> LENGTH: 10
<212> TYPE: PRT
<213> ORGANISM: Artificial Sequence
<220> FEATURE:
<223> OTHER INFORMATION: synthetic construct

<400> SEQUENCE: 165

Gly Phe Ser Leu Thr Ser Tyr Ala Met Ser
1               5                   10

<210> SEQ ID NO 166
<211> LENGTH: 16
<212> TYPE: PRT
<213> ORGANISM: Artificial Sequence
<220> FEATURE:
<223> OTHER INFORMATION: synthetic construct

<400> SEQUENCE: 166

Ile Ile Gly Ser Pro Gly Thr Thr Gly Tyr Ala Thr Trp Ala Lys Gly
1               5                   10                  15

<210> SEQ ID NO 167
<211> LENGTH: 9
<212> TYPE: PRT
<213> ORGANISM: Artificial Sequence
<220> FEATURE:
<223> OTHER INFORMATION: synthetic construct

<400> SEQUENCE: 167

Gly Trp Phe Tyr Tyr Gly Met Ala Leu
1               5

<210> SEQ ID NO 168
<211> LENGTH: 11
<212> TYPE: PRT
<213> ORGANISM: Artificial Sequence
<220> FEATURE:
<223> OTHER INFORMATION: synthetic construct

<400> SEQUENCE: 168

Gln Ala Ser Glu Ser Ile Ser Ser Tyr Leu Ala
1               5                   10

<210> SEQ ID NO 169
<211> LENGTH: 7
<212> TYPE: PRT
<213> ORGANISM: Artificial Sequence
<220> FEATURE:
<223> OTHER INFORMATION: synthetic construct
```

<400> SEQUENCE: 169

Gly Ala Ser Thr Leu Ala Ser
1               5

<210> SEQ ID NO 170
<211> LENGTH: 10
<212> TYPE: PRT
<213> ORGANISM: Artificial Sequence
<220> FEATURE:
<223> OTHER INFORMATION: synthetic construct

<400> SEQUENCE: 170

Gln Gly Tyr Phe Gly Asp Tyr Ile Tyr Gly
1               5                   10

<210> SEQ ID NO 171
<211> LENGTH: 10
<212> TYPE: PRT
<213> ORGANISM: Artificial Sequence
<220> FEATURE:
<223> OTHER INFORMATION: synthetic construct

<400> SEQUENCE: 171

Gly Phe Ser Leu Thr Ser Tyr Ala Met Ser
1               5                   10

<210> SEQ ID NO 172
<211> LENGTH: 16
<212> TYPE: PRT
<213> ORGANISM: Artificial Sequence
<220> FEATURE:
<223> OTHER INFORMATION: synthetic construct

<400> SEQUENCE: 172

Ile Ile Gly Ser Pro Gly Thr Thr Gly Tyr Ala Thr Trp Ala Lys Gly
1               5                   10                  15

<210> SEQ ID NO 173
<211> LENGTH: 9
<212> TYPE: PRT
<213> ORGANISM: Artificial Sequence
<220> FEATURE:
<223> OTHER INFORMATION: synthetic construct

<400> SEQUENCE: 173

Gly Trp Phe Tyr Tyr Gly Met Ala Leu
1               5

<210> SEQ ID NO 174
<211> LENGTH: 11
<212> TYPE: PRT
<213> ORGANISM: Artificial Sequence
<220> FEATURE:
<223> OTHER INFORMATION: synthetic construct

<400> SEQUENCE: 174

Gln Ala Ser Glu Ser Ile Ser Ser Tyr Leu Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: synthetic construct

```
<400> SEQUENCE: 175

Gly Ala Ser Thr Leu Ala Ser
1               5

<210> SEQ ID NO 176
<211> LENGTH: 10
<212> TYPE: PRT
<213> ORGANISM: Artificial Sequence
<220> FEATURE:
<223> OTHER INFORMATION: synthetic construct

<400> SEQUENCE: 176

Gln Gly Tyr Phe Gly Asp Tyr Ile Tyr Gly
1               5                   10

<210> SEQ ID NO 177
<211> LENGTH: 10
<212> TYPE: PRT
<213> ORGANISM: Artificial Sequence
<220> FEATURE:
<223> OTHER INFORMATION: synthetic construct

<400> SEQUENCE: 177

Gly Phe Ser Leu Thr Ser Tyr Ala Met Ser
1               5                   10

<210> SEQ ID NO 178
<211> LENGTH: 16
<212> TYPE: PRT
<213> ORGANISM: Artificial Sequence
<220> FEATURE:
<223> OTHER INFORMATION: synthetic construct

<400> SEQUENCE: 178

Ile Ile Gly Ser Pro Gly Thr Thr Gly Tyr Ala Thr Trp Ala Lys Gly
1               5                   10                  15

<210> SEQ ID NO 179
<211> LENGTH: 9
<212> TYPE: PRT
<213> ORGANISM: Artificial Sequence
<220> FEATURE:
<223> OTHER INFORMATION: synthetic construct

<400> SEQUENCE: 179

Gly Trp Phe Tyr Tyr Gly Met Ala Leu
1               5

<210> SEQ ID NO 180
<211> LENGTH: 11
<212> TYPE: PRT
<213> ORGANISM: Artificial Sequence
<220> FEATURE:
<223> OTHER INFORMATION: synthetic construct

<400> SEQUENCE: 180

Gln Ala Ser Glu Ser Ile Ser Ser Tyr Leu Ala
1               5                   10

<210> SEQ ID NO 181
<211> LENGTH: 7
<212> TYPE: PRT
<213> ORGANISM: Artificial Sequence
<220> FEATURE:
<223> OTHER INFORMATION: synthetic construct

<400> SEQUENCE: 181
```

```
Gly Ala Ser Thr Leu Ala Ser
1               5

<210> SEQ ID NO 182
<211> LENGTH: 10
<212> TYPE: PRT
<213> ORGANISM: Artificial Sequence
<220> FEATURE:
<223> OTHER INFORMATION: synthetic construct

<400> SEQUENCE: 182

Gln Gly Tyr Phe Gly Asp Tyr Ile Tyr Gly
1               5                   10

<210> SEQ ID NO 183
<211> LENGTH: 10
<212> TYPE: PRT
<213> ORGANISM: Artificial Sequence
<220> FEATURE:
<223> OTHER INFORMATION: synthetic construct

<400> SEQUENCE: 183

Gly Phe Ser Leu Thr Ser Tyr Ala Met Ser
1               5                   10

<210> SEQ ID NO 184
<211> LENGTH: 16
<212> TYPE: PRT
<213> ORGANISM: Artificial Sequence
<220> FEATURE:
<223> OTHER INFORMATION: synthetic construct

<400> SEQUENCE: 184

Ile Ile Gly Ser Pro Gly Thr Thr Gly Tyr Ala Thr Trp Ala Lys Gly
1               5                   10                  15

<210> SEQ ID NO 185
<211> LENGTH: 9
<212> TYPE: PRT
<213> ORGANISM: Artificial Sequence
<220> FEATURE:
<223> OTHER INFORMATION: synthetic construct

<400> SEQUENCE: 185

Gly Trp Phe Tyr Tyr Gly Met Ala Leu
1               5

<210> SEQ ID NO 186
<211> LENGTH: 11
<212> TYPE: PRT
<213> ORGANISM: Artificial Sequence
<220> FEATURE:
<223> OTHER INFORMATION: synthetic construct

<400> SEQUENCE: 186

Gln Ala Ser Gln Ser Ile Ser Asn Tyr Leu Ser
1               5                   10

<210> SEQ ID NO 187
<211> LENGTH: 7
<212> TYPE: PRT
<213> ORGANISM: Artificial Sequence
<220> FEATURE:
<223> OTHER INFORMATION: synthetic construct

<400> SEQUENCE: 187
```

```
Trp Ala Ser Asn Leu Ala Ser
1               5
```

<210> SEQ ID NO 188
<211> LENGTH: 13
<212> TYPE: PRT
<213> ORGANISM: Artificial Sequence
<220> FEATURE:
<223> OTHER INFORMATION: synthetic construct

<400> SEQUENCE: 188

```
Leu Gly Glu Phe Ser Cys Ser Ser Ala Asp Cys Phe Ala
1               5                   10
```

<210> SEQ ID NO 189
<211> LENGTH: 10
<212> TYPE: PRT
<213> ORGANISM: Artificial Sequence
<220> FEATURE:
<223> OTHER INFORMATION: synthetic construct

<400> SEQUENCE: 189

```
Gly Phe Asp Leu Ser Asn Tyr Ala Met Thr
1               5                   10
```

<210> SEQ ID NO 190
<211> LENGTH: 16
<212> TYPE: PRT
<213> ORGANISM: Artificial Sequence
<220> FEATURE:
<223> OTHER INFORMATION: synthetic construct

<400> SEQUENCE: 190

```
Ala Ile His Gly Ser Gly Val Thr Asp Cys Ala Ser Trp Thr Arg Gly
1               5                   10                  15
```

<210> SEQ ID NO 191
<211> LENGTH: 11
<212> TYPE: PRT
<213> ORGANISM: Artificial Sequence
<220> FEATURE:
<223> OTHER INFORMATION: synthetic construct

<400> SEQUENCE: 191

```
Glu Ser Ala Gly Ile Asn Thr Asp Tyr Asp Leu
1               5                   10
```

<210> SEQ ID NO 192
<211> LENGTH: 11
<212> TYPE: PRT
<213> ORGANISM: Artificial Sequence
<220> FEATURE:
<223> OTHER INFORMATION: synthetic construct

<400> SEQUENCE: 192

```
Gln Ala Ser Gln Ser Ile Ser Asn Tyr Leu Ser
1               5                   10
```

<210> SEQ ID NO 193
<211> LENGTH: 7
<212> TYPE: PRT
<213> ORGANISM: Artificial Sequence
<220> FEATURE:
<223> OTHER INFORMATION: synthetic construct

<400> SEQUENCE: 193

```
Trp Ala Ser Asn Leu Ala Ser
```

```
1               5

<210> SEQ ID NO 194
<211> LENGTH: 13
<212> TYPE: PRT
<213> ORGANISM: Artificial Sequence
<220> FEATURE:
<223> OTHER INFORMATION: synthetic construct

<400> SEQUENCE: 194

Leu Gly Glu Phe Ser Cys Ser Ser Ala Asp Cys Phe Ala
1               5                   10

<210> SEQ ID NO 195
<211> LENGTH: 10
<212> TYPE: PRT
<213> ORGANISM: Artificial Sequence
<220> FEATURE:
<223> OTHER INFORMATION: synthetic construct

<400> SEQUENCE: 195

Gly Phe Asp Leu Ser Asn Tyr Ala Met Thr
1               5                   10

<210> SEQ ID NO 196
<211> LENGTH: 16
<212> TYPE: PRT
<213> ORGANISM: Artificial Sequence
<220> FEATURE:
<223> OTHER INFORMATION: synthetic construct

<400> SEQUENCE: 196

Ala Ile His Gly Ser Gly Val Thr Asp Cys Ala Ser Trp Thr Arg Gly
1               5                   10                  15

<210> SEQ ID NO 197
<211> LENGTH: 11
<212> TYPE: PRT
<213> ORGANISM: Artificial Sequence
<220> FEATURE:
<223> OTHER INFORMATION: synthetic construct

<400> SEQUENCE: 197

Glu Ser Ala Gly Ile Asn Thr Asp Tyr Asp Leu
1               5                   10

<210> SEQ ID NO 198
<211> LENGTH: 11
<212> TYPE: PRT
<213> ORGANISM: Artificial Sequence
<220> FEATURE:
<223> OTHER INFORMATION: synthetic construct

<400> SEQUENCE: 198

Gln Ala Ser Lys Ser Ile Gly Ser Tyr Leu Ser
1               5                   10

<210> SEQ ID NO 199
<211> LENGTH: 7
<212> TYPE: PRT
<213> ORGANISM: Artificial Sequence
<220> FEATURE:
<223> OTHER INFORMATION: synthetic construct

<400> SEQUENCE: 199

Arg Ala Ser Thr Leu Ala Ser
1               5
```

<210> SEQ ID NO 200
<211> LENGTH: 10
<212> TYPE: PRT
<213> ORGANISM: Artificial Sequence
<220> FEATURE:
<223> OTHER INFORMATION: synthetic construct

<400> SEQUENCE: 200

Gln Ala Tyr Tyr Gly Asp Tyr Ile Tyr Asp
1               5                   10

<210> SEQ ID NO 201
<211> LENGTH: 10
<212> TYPE: PRT
<213> ORGANISM: Artificial Sequence
<220> FEATURE:
<223> OTHER INFORMATION: synthetic construct

<400> SEQUENCE: 201

Gly Phe Ser Leu Ser Ser Tyr Pro Met Ser
1               5                   10

<210> SEQ ID NO 202
<211> LENGTH: 16
<212> TYPE: PRT
<213> ORGANISM: Artificial Sequence
<220> FEATURE:
<223> OTHER INFORMATION: synthetic construct

<400> SEQUENCE: 202

Ile Ile Gly Ser Thr Gly Ser Thr Gly Tyr Ala Asn Trp Ala Lys Gly
1               5                   10                  15

<210> SEQ ID NO 203
<211> LENGTH: 9
<212> TYPE: PRT
<213> ORGANISM: Artificial Sequence
<220> FEATURE:
<223> OTHER INFORMATION: synthetic construct

<400> SEQUENCE: 203

Gly Trp Phe Tyr Tyr Gly Leu Asp Leu
1               5

<210> SEQ ID NO 204
<211> LENGTH: 11
<212> TYPE: PRT
<213> ORGANISM: Artificial Sequence
<220> FEATURE:
<223> OTHER INFORMATION: synthetic construct

<400> SEQUENCE: 204

Gln Ala Ser Gln Ser Ile Gly Ser Tyr Leu Ser
1               5                   10

<210> SEQ ID NO 205
<211> LENGTH: 7
<212> TYPE: PRT
<213> ORGANISM: Artificial Sequence
<220> FEATURE:
<223> OTHER INFORMATION: synthetic construct

<400> SEQUENCE: 205

Arg Ala Ser Thr Leu Ala Ser
1               5

<210> SEQ ID NO 206
<211> LENGTH: 10
<212> TYPE: PRT
<213> ORGANISM: Artificial Sequence
<220> FEATURE:
<223> OTHER INFORMATION: synthetic construct

<400> SEQUENCE: 206

Gln Ala Tyr Tyr Gly Asp Tyr Ile Tyr Asp
1               5                   10

<210> SEQ ID NO 207
<211> LENGTH: 10
<212> TYPE: PRT
<213> ORGANISM: Artificial Sequence
<220> FEATURE:
<223> OTHER INFORMATION: synthetic construct

<400> SEQUENCE: 207

Gly Phe Ser Leu Ser Ser Tyr Pro Met Ser
1               5                   10

<210> SEQ ID NO 208
<211> LENGTH: 16
<212> TYPE: PRT
<213> ORGANISM: Artificial Sequence
<220> FEATURE:
<223> OTHER INFORMATION: synthetic construct

<400> SEQUENCE: 208

Ile Ile Gly Ser Thr Gly Ser Thr Gly Tyr Ala Asn Trp Ala Lys Gly
1               5                   10                  15

<210> SEQ ID NO 209
<211> LENGTH: 9
<212> TYPE: PRT
<213> ORGANISM: Artificial Sequence
<220> FEATURE:
<223> OTHER INFORMATION: synthetic construct

<400> SEQUENCE: 209

Gly Trp Phe Tyr Tyr Gly Leu Asp Leu
1               5

<210> SEQ ID NO 210
<211> LENGTH: 11
<212> TYPE: PRT
<213> ORGANISM: Artificial Sequence
<220> FEATURE:
<223> OTHER INFORMATION: synthetic construct

<400> SEQUENCE: 210

Gln Ala Ser Gln Ser Ile Gly Ser Tyr Leu Ala
1               5                   10

<210> SEQ ID NO 211
<211> LENGTH: 7
<212> TYPE: PRT
<213> ORGANISM: Artificial Sequence
<220> FEATURE:
<223> OTHER INFORMATION: synthetic construct

<400> SEQUENCE: 211

Asp Ala Ser Asp Leu Ala Ser
1               5

```
<210> SEQ ID NO 212
<211> LENGTH: 12
<212> TYPE: PRT
<213> ORGANISM: Artificial Sequence
<220> FEATURE:
<223> OTHER INFORMATION: synthetic construct

<400> SEQUENCE: 212

Gln Ser Ala Val Tyr Asp Ser Ser Tyr Val Val Thr
1               5                   10

<210> SEQ ID NO 213
<211> LENGTH: 10
<212> TYPE: PRT
<213> ORGANISM: Artificial Sequence
<220> FEATURE:
<223> OTHER INFORMATION: synthetic construct

<400> SEQUENCE: 213

Gly Phe Ser Leu Ser Ser Tyr Asp Met Ser
1               5                   10

<210> SEQ ID NO 214
<211> LENGTH: 16
<212> TYPE: PRT
<213> ORGANISM: Artificial Sequence
<220> FEATURE:
<223> OTHER INFORMATION: synthetic construct

<400> SEQUENCE: 214

Ile Ser Asp Ser Leu Gly Thr Thr Trp Tyr Ala Asn Trp Ala Lys Gly
1               5                   10                  15

<210> SEQ ID NO 215
<211> LENGTH: 11
<212> TYPE: PRT
<213> ORGANISM: Artificial Sequence
<220> FEATURE:
<223> OTHER INFORMATION: synthetic construct

<400> SEQUENCE: 215

Glu Ser Gly Asp Ile Arg Ile Asp Tyr Asp Leu
1               5                   10

<210> SEQ ID NO 216
<211> LENGTH: 11
<212> TYPE: PRT
<213> ORGANISM: Artificial Sequence
<220> FEATURE:
<223> OTHER INFORMATION: synthetic construct

<400> SEQUENCE: 216

Gln Ala Ser Gln Ser Ile Gly Ser Tyr Leu Ala
1               5                   10

<210> SEQ ID NO 217
<211> LENGTH: 7
<212> TYPE: PRT
<213> ORGANISM: Artificial Sequence
<220> FEATURE:
<223> OTHER INFORMATION: synthetic construct

<400> SEQUENCE: 217

Asp Ala Ser Asp Leu Ala Ser
1               5

<210> SEQ ID NO 218
```

```
<211> LENGTH: 12
<212> TYPE: PRT
<213> ORGANISM: Artificial Sequence
<220> FEATURE:
<223> OTHER INFORMATION: synthetic construct

<400> SEQUENCE: 218

Gln Ser Ala Val Tyr Asp Ser Ser Tyr Val Val Thr
1               5                   10

<210> SEQ ID NO 219
<211> LENGTH: 10
<212> TYPE: PRT
<213> ORGANISM: Artificial Sequence
<220> FEATURE:
<223> OTHER INFORMATION: synthetic construct

<400> SEQUENCE: 219

Gly Phe Ser Leu Ser Ser Tyr Asp Met Ser
1               5                   10

<210> SEQ ID NO 220
<211> LENGTH: 16
<212> TYPE: PRT
<213> ORGANISM: Artificial Sequence
<220> FEATURE:
<223> OTHER INFORMATION: synthetic construct

<400> SEQUENCE: 220

Ile Ser Asp Ser Leu Gly Thr Thr Trp Tyr Ala Asn Trp Ala Lys Gly
1               5                   10                  15

<210> SEQ ID NO 221
<211> LENGTH: 11
<212> TYPE: PRT
<213> ORGANISM: Artificial Sequence
<220> FEATURE:
<223> OTHER INFORMATION: synthetic construct

<400> SEQUENCE: 221

Glu Ser Gly Asp Ile Arg Ile Asp Tyr Asp Leu
1               5                   10

<210> SEQ ID NO 222
<211> LENGTH: 11
<212> TYPE: PRT
<213> ORGANISM: Artificial Sequence
<220> FEATURE:
<223> OTHER INFORMATION: synthetic construct

<400> SEQUENCE: 222

Gln Ala Ser Gln Ser Ile Gly Ser Tyr Leu Ala
1               5                   10

<210> SEQ ID NO 223
<211> LENGTH: 7
<212> TYPE: PRT
<213> ORGANISM: Artificial Sequence
<220> FEATURE:
<223> OTHER INFORMATION: synthetic construct

<400> SEQUENCE: 223

Asp Ala Ser Asp Leu Ala Ser
1               5

<210> SEQ ID NO 224
<211> LENGTH: 12
```

```
<212> TYPE: PRT
<213> ORGANISM: Artificial Sequence
<220> FEATURE:
<223> OTHER INFORMATION: synthetic construct

<400> SEQUENCE: 224

Gln Ser Ala Val Tyr Asp Ser Ser Tyr Val Val Thr
1               5                   10

<210> SEQ ID NO 225
<211> LENGTH: 10
<212> TYPE: PRT
<213> ORGANISM: Artificial Sequence
<220> FEATURE:
<223> OTHER INFORMATION: synthetic construct

<400> SEQUENCE: 225

Gly Phe Ser Leu Ser Ser Tyr Asp Met Ser
1               5                   10

<210> SEQ ID NO 226
<211> LENGTH: 16
<212> TYPE: PRT
<213> ORGANISM: Artificial Sequence
<220> FEATURE:
<223> OTHER INFORMATION: synthetic construct

<400> SEQUENCE: 226

Ile Ser Asp Ser Leu Gly Thr Thr Trp Tyr Ala Asn Trp Ala Lys Gly
1               5                   10                  15

<210> SEQ ID NO 227
<211> LENGTH: 11
<212> TYPE: PRT
<213> ORGANISM: Artificial Sequence
<220> FEATURE:
<223> OTHER INFORMATION: synthetic construct

<400> SEQUENCE: 227

Glu Ser Gly Asp Ile Arg Ile Asp Tyr Asp Leu
1               5                   10

<210> SEQ ID NO 228
<211> LENGTH: 11
<212> TYPE: PRT
<213> ORGANISM: Artificial Sequence
<220> FEATURE:
<223> OTHER INFORMATION: synthetic construct

<400> SEQUENCE: 228

Gln Ala Ser Gln Ser Ile Gly Ser Tyr Leu Ala
1               5                   10

<210> SEQ ID NO 229
<211> LENGTH: 7
<212> TYPE: PRT
<213> ORGANISM: Artificial Sequence
<220> FEATURE:
<223> OTHER INFORMATION: synthetic construct

<400> SEQUENCE: 229

Asp Ala Ser Asp Leu Ala Ser
1               5

<210> SEQ ID NO 230
<211> LENGTH: 12
<212> TYPE: PRT
```

```
<213> ORGANISM: Artificial Sequence
<220> FEATURE:
<223> OTHER INFORMATION: synthetic construct

<400> SEQUENCE: 230

Gln Ser Ala Val Tyr Asp Ser Ser Tyr Val Val Thr
1               5                   10

<210> SEQ ID NO 231
<211> LENGTH: 10
<212> TYPE: PRT
<213> ORGANISM: Artificial Sequence
<220> FEATURE:
<223> OTHER INFORMATION: synthetic construct

<400> SEQUENCE: 231

Gly Phe Ser Leu Ser Ser Tyr Asp Met Ser
1               5                   10

<210> SEQ ID NO 232
<211> LENGTH: 16
<212> TYPE: PRT
<213> ORGANISM: Artificial Sequence
<220> FEATURE:
<223> OTHER INFORMATION: synthetic construct

<400> SEQUENCE: 232

Ile Ser Asp Ser Leu Gly Thr Thr Trp Tyr Ala Asn Trp Ala Lys Gly
1               5                   10                  15

<210> SEQ ID NO 233
<211> LENGTH: 11
<212> TYPE: PRT
<213> ORGANISM: Artificial Sequence
<220> FEATURE:
<223> OTHER INFORMATION: synthetic construct

<400> SEQUENCE: 233

Glu Ser Gly Asp Ile Arg Ile Asp Tyr Asp Leu
1               5                   10

<210> SEQ ID NO 234
<211> LENGTH: 12
<212> TYPE: PRT
<213> ORGANISM: Artificial Sequence
<220> FEATURE:
<223> OTHER INFORMATION: synthetic construct

<400> SEQUENCE: 234

Gln Ala Ser Gln Ser Leu Asn Ile Asn Tyr Leu Ser
1               5                   10

<210> SEQ ID NO 235
<211> LENGTH: 7
<212> TYPE: PRT
<213> ORGANISM: Artificial Sequence
<220> FEATURE:
<223> OTHER INFORMATION: synthetic construct

<400> SEQUENCE: 235

Ser Ala Ser Thr Leu Ala Ser
1               5

<210> SEQ ID NO 236
<211> LENGTH: 12
<212> TYPE: PRT
<213> ORGANISM: Artificial Sequence
```

```
<220> FEATURE:
<223> OTHER INFORMATION: synthetic construct

<400> SEQUENCE: 236

Gln Gln Ser Val Asn Tyr Gly Arg Val Asp Asn Ile
1               5                   10

<210> SEQ ID NO 237
<211> LENGTH: 10
<212> TYPE: PRT
<213> ORGANISM: Artificial Sequence
<220> FEATURE:
<223> OTHER INFORMATION: synthetic construct

<400> SEQUENCE: 237

Gly Phe Thr Ile Ser Asn Tyr His Met Ser
1               5                   10

<210> SEQ ID NO 238
<211> LENGTH: 16
<212> TYPE: PRT
<213> ORGANISM: Artificial Sequence
<220> FEATURE:
<223> OTHER INFORMATION: synthetic construct

<400> SEQUENCE: 238

Arg Ile Val Ser Tyr Gly Gly Thr Tyr Tyr Ala Asn Trp Ala Lys Gly
1               5                   10                  15

<210> SEQ ID NO 239
<211> LENGTH: 11
<212> TYPE: PRT
<213> ORGANISM: Artificial Sequence
<220> FEATURE:
<223> OTHER INFORMATION: synthetic construct

<400> SEQUENCE: 239

Asp Ser Ser Gly Ser Gly Phe Ser Phe Ala Leu
1               5                   10

<210> SEQ ID NO 240
<211> LENGTH: 12
<212> TYPE: PRT
<213> ORGANISM: Artificial Sequence
<220> FEATURE:
<223> OTHER INFORMATION: synthetic construct

<400> SEQUENCE: 240

Gln Ala Ser Gln Ser Ile Thr Thr Ser Tyr Leu Ser
1               5                   10

<210> SEQ ID NO 241
<211> LENGTH: 7
<212> TYPE: PRT
<213> ORGANISM: Artificial Sequence
<220> FEATURE:
<223> OTHER INFORMATION: synthetic construct

<400> SEQUENCE: 241

Lys Ala Ser Thr Leu Ala Ser
1               5

<210> SEQ ID NO 242
<211> LENGTH: 12
<212> TYPE: PRT
<213> ORGANISM: Artificial Sequence
<220> FEATURE:
```

```
<223> OTHER INFORMATION: synthetic construct

<400> SEQUENCE: 242

Gln Gln Ser His Asn Tyr Gly Arg Val Asp Asn Ile
1               5                   10

<210> SEQ ID NO 243
<211> LENGTH: 10
<212> TYPE: PRT
<213> ORGANISM: Artificial Sequence
<220> FEATURE:
<223> OTHER INFORMATION: synthetic construct

<400> SEQUENCE: 243

Gly Phe Thr Ile Ser Asn Tyr His Met Ser
1               5                   10

<210> SEQ ID NO 244
<211> LENGTH: 16
<212> TYPE: PRT
<213> ORGANISM: Artificial Sequence
<220> FEATURE:
<223> OTHER INFORMATION: synthetic construct

<400> SEQUENCE: 244

Arg Ile Val Ser Tyr Gly Gly Thr Tyr Tyr Ala Asn Trp Ala Lys Gly
1               5                   10                  15

<210> SEQ ID NO 245
<211> LENGTH: 11
<212> TYPE: PRT
<213> ORGANISM: Artificial Sequence
<220> FEATURE:
<223> OTHER INFORMATION: synthetic construct

<400> SEQUENCE: 245

Asp Ser Ser Gly Ser Gly Phe Ser Phe Ala Leu
1               5                   10

<210> SEQ ID NO 246
<211> LENGTH: 12
<212> TYPE: PRT
<213> ORGANISM: Artificial Sequence
<220> FEATURE:
<223> OTHER INFORMATION: synthetic construct

<400> SEQUENCE: 246

Gln Ala Ser Gln Ser Ile Thr Thr Ser Tyr Leu Ser
1               5                   10

<210> SEQ ID NO 247
<211> LENGTH: 7
<212> TYPE: PRT
<213> ORGANISM: Artificial Sequence
<220> FEATURE:
<223> OTHER INFORMATION: synthetic construct

<400> SEQUENCE: 247

Lys Ala Ser Thr Leu Ala Ser
1               5

<210> SEQ ID NO 248
<211> LENGTH: 12
<212> TYPE: PRT
<213> ORGANISM: Artificial Sequence
<220> FEATURE:
<223> OTHER INFORMATION: synthetic construct
```

<400> SEQUENCE: 248

Gln Gln Ser His Asn Tyr Gly Arg Val Asp Asn Ile
1               5                   10

<210> SEQ ID NO 249
<211> LENGTH: 10
<212> TYPE: PRT
<213> ORGANISM: Artificial Sequence
<220> FEATURE:
<223> OTHER INFORMATION: synthetic construct

<400> SEQUENCE: 249

Gly Phe Thr Ile Ser Asn Tyr His Met Ser
1               5                   10

<210> SEQ ID NO 250
<211> LENGTH: 16
<212> TYPE: PRT
<213> ORGANISM: Artificial Sequence
<220> FEATURE:
<223> OTHER INFORMATION: synthetic construct

<400> SEQUENCE: 250

Arg Ile Val Ser Tyr Gly Gly Thr Tyr Tyr Ala Asn Trp Ala Lys Gly
1               5                   10                  15

<210> SEQ ID NO 251
<211> LENGTH: 11
<212> TYPE: PRT
<213> ORGANISM: Artificial Sequence
<220> FEATURE:
<223> OTHER INFORMATION: synthetic construct

<400> SEQUENCE: 251

Asp Ser Ser Gly Ser Gly Phe Ser Phe Ala Leu
1               5                   10

<210> SEQ ID NO 252
<211> LENGTH: 12
<212> TYPE: PRT
<213> ORGANISM: Artificial Sequence
<220> FEATURE:
<223> OTHER INFORMATION: synthetic construct

<400> SEQUENCE: 252

Gln Ala Ser Gln Ser Ile Thr Thr Ser Tyr Leu Ser
1               5                   10

<210> SEQ ID NO 253
<211> LENGTH: 7
<212> TYPE: PRT
<213> ORGANISM: Artificial Sequence
<220> FEATURE:
<223> OTHER INFORMATION: synthetic construct

<400> SEQUENCE: 253

Lys Ala Ser Thr Leu Ala Ser
1               5

<210> SEQ ID NO 254
<211> LENGTH: 12
<212> TYPE: PRT
<213> ORGANISM: Artificial Sequence
<220> FEATURE:
<223> OTHER INFORMATION: synthetic construct

<400> SEQUENCE: 254

Gln Gln Ser His Asn Tyr Gly Arg Val Asp Asn Ile
1               5                   10

<210> SEQ ID NO 255
<211> LENGTH: 10
<212> TYPE: PRT
<213> ORGANISM: Artificial Sequence
<220> FEATURE:
<223> OTHER INFORMATION: synthetic construct

<400> SEQUENCE: 255

Gly Phe Thr Ile Ser Asn Tyr His Met Ser
1               5                   10

<210> SEQ ID NO 256
<211> LENGTH: 16
<212> TYPE: PRT
<213> ORGANISM: Artificial Sequence
<220> FEATURE:
<223> OTHER INFORMATION: synthetic construct

<400> SEQUENCE: 256

Arg Ile Val Ser Tyr Gly Gly Thr Tyr Tyr Ala Asn Trp Ala Lys Gly
1               5                   10                  15

<210> SEQ ID NO 257
<211> LENGTH: 11
<212> TYPE: PRT
<213> ORGANISM: Artificial Sequence
<220> FEATURE:
<223> OTHER INFORMATION: synthetic construct

<400> SEQUENCE: 257

Asp Ser Ser Gly Ser Gly Phe Ser Phe Ala Leu
1               5                   10

<210> SEQ ID NO 258
<211> LENGTH: 12
<212> TYPE: PRT
<213> ORGANISM: Artificial Sequence
<220> FEATURE:
<223> OTHER INFORMATION: synthetic construct

<400> SEQUENCE: 258

Gln Ala Ser Gln Ser Ile Thr Thr Ser Tyr Leu Ser
1               5                   10

<210> SEQ ID NO 259
<211> LENGTH: 7
<212> TYPE: PRT
<213> ORGANISM: Artificial Sequence
<220> FEATURE:
<223> OTHER INFORMATION: synthetic construct

<400> SEQUENCE: 259

Lys Ala Ser Thr Leu Ala Ser
1               5

<210> SEQ ID NO 260
<211> LENGTH: 12
<212> TYPE: PRT
<213> ORGANISM: Artificial Sequence
<220> FEATURE:
<223> OTHER INFORMATION: synthetic construct

<400> SEQUENCE: 260

Gln Gln Ser His Asn Tyr Gly Arg Val Asp Asn Ile
1               5                   10

<210> SEQ ID NO 261
<211> LENGTH: 10
<212> TYPE: PRT
<213> ORGANISM: Artificial Sequence
<220> FEATURE:
<223> OTHER INFORMATION: synthetic construct

<400> SEQUENCE: 261

Gly Phe Thr Ile Ser Asn Tyr His Met Ser
1               5                   10

<210> SEQ ID NO 262
<211> LENGTH: 16
<212> TYPE: PRT
<213> ORGANISM: Artificial Sequence
<220> FEATURE:
<223> OTHER INFORMATION: synthetic construct

<400> SEQUENCE: 262

Arg Ile Val Ser Tyr Gly Gly Thr Tyr Tyr Ala Asn Trp Ala Lys Gly
1               5                   10                  15

<210> SEQ ID NO 263
<211> LENGTH: 11
<212> TYPE: PRT
<213> ORGANISM: Artificial Sequence
<220> FEATURE:
<223> OTHER INFORMATION: synthetic construct

<400> SEQUENCE: 263

Asp Ser Ser Gly Ser Gly Phe Ser Phe Ala Leu
1               5                   10

<210> SEQ ID NO 264
<211> LENGTH: 11
<212> TYPE: PRT
<213> ORGANISM: Artificial Sequence
<220> FEATURE:
<223> OTHER INFORMATION: synthetic construct

<400> SEQUENCE: 264

Gln Ala Ser Gln Asn Ile Tyr Ser Asn Leu Ala
1               5                   10

<210> SEQ ID NO 265
<211> LENGTH: 7
<212> TYPE: PRT
<213> ORGANISM: Artificial Sequence
<220> FEATURE:
<223> OTHER INFORMATION: synthetic construct

<400> SEQUENCE: 265

Lys Ala Ser Thr Leu Ala Ser
1               5

<210> SEQ ID NO 266
<211> LENGTH: 10
<212> TYPE: PRT
<213> ORGANISM: Artificial Sequence
<220> FEATURE:
<223> OTHER INFORMATION: synthetic construct

<400> SEQUENCE: 266

```
Gln Ala Tyr Val Gly Asn Tyr Ile Tyr Thr
1               5                   10
```

<210> SEQ ID NO 267
<211> LENGTH: 10
<212> TYPE: PRT
<213> ORGANISM: Artificial Sequence
<220> FEATURE:
<223> OTHER INFORMATION: synthetic construct

<400> SEQUENCE: 267

```
Gly Phe Ser Leu Ser Ser Tyr Pro Met Ser
1               5                   10
```

<210> SEQ ID NO 268
<211> LENGTH: 16
<212> TYPE: PRT
<213> ORGANISM: Artificial Sequence
<220> FEATURE:
<223> OTHER INFORMATION: synthetic construct

<400> SEQUENCE: 268

```
Ile Ile Gly Ser Ser Gly Ser Ile Gly Tyr Ala Ser Trp Ala Lys Gly
1               5                   10                  15
```

<210> SEQ ID NO 269
<211> LENGTH: 9
<212> TYPE: PRT
<213> ORGANISM: Artificial Sequence
<220> FEATURE:
<223> OTHER INFORMATION: synthetic construct

<400> SEQUENCE: 269

```
Gly Trp Phe Tyr Tyr Gly Met Asp Leu
1               5
```

<210> SEQ ID NO 270
<211> LENGTH: 11
<212> TYPE: PRT
<213> ORGANISM: Artificial Sequence
<220> FEATURE:
<223> OTHER INFORMATION: synthetic construct

<400> SEQUENCE: 270

```
Gln Ala Ser Gln Ser Ile Gly Ser Asn Leu Ala
1               5                   10
```

<210> SEQ ID NO 271
<211> LENGTH: 7
<212> TYPE: PRT
<213> ORGANISM: Artificial Sequence
<220> FEATURE:
<223> OTHER INFORMATION: synthetic construct

<400> SEQUENCE: 271

```
Arg Ala Ser Thr Leu Ala Ser
1               5
```

<210> SEQ ID NO 272
<211> LENGTH: 10
<212> TYPE: PRT
<213> ORGANISM: Artificial Sequence
<220> FEATURE:
<223> OTHER INFORMATION: synthetic construct

<400> SEQUENCE: 272

```
Gln Gly Tyr Tyr Gly Asp Gly Ile Tyr Gly
```

```
1               5                   10
```

<210> SEQ ID NO 273
<211> LENGTH: 10
<212> TYPE: PRT
<213> ORGANISM: Artificial Sequence
<220> FEATURE:
<223> OTHER INFORMATION: synthetic construct

<400> SEQUENCE: 273

```
Gly Phe Ser Leu Ser Ser Tyr Pro Met Ser
1               5                   10
```

<210> SEQ ID NO 274
<211> LENGTH: 16
<212> TYPE: PRT
<213> ORGANISM: Artificial Sequence
<220> FEATURE:
<223> OTHER INFORMATION: synthetic construct

<400> SEQUENCE: 274

```
Leu Ile Gly Ser Ser Gly Thr Ile Tyr Phe Ala Thr Trp Ala Lys Gly
1               5                   10                  15
```

<210> SEQ ID NO 275
<211> LENGTH: 9
<212> TYPE: PRT
<213> ORGANISM: Artificial Sequence
<220> FEATURE:
<223> OTHER INFORMATION: synthetic construct

<400> SEQUENCE: 275

```
Gly Trp Phe Tyr Tyr Gly Met Asp Leu
1               5
```

<210> SEQ ID NO 276
<211> LENGTH: 11
<212> TYPE: PRT
<213> ORGANISM: Artificial Sequence
<220> FEATURE:
<223> OTHER INFORMATION: synthetic construct

<400> SEQUENCE: 276

```
Gln Ala Ser Gln Ser Ile Ser Ser Trp Leu Ser
1               5                   10
```

<210> SEQ ID NO 277
<211> LENGTH: 7
<212> TYPE: PRT
<213> ORGANISM: Artificial Sequence
<220> FEATURE:
<223> OTHER INFORMATION: synthetic construct

<400> SEQUENCE: 277

```
Gly Ala Ser Thr Leu Ala Ser
1               5
```

<210> SEQ ID NO 278
<211> LENGTH: 12
<212> TYPE: PRT
<213> ORGANISM: Artificial Sequence
<220> FEATURE:
<223> OTHER INFORMATION: synthetic construct

<400> SEQUENCE: 278

```
Gln Ser Tyr Tyr Tyr Ile Ser Ser Ser Ser Tyr Thr
1               5                   10
```

<210> SEQ ID NO 279
<211> LENGTH: 10
<212> TYPE: PRT
<213> ORGANISM: Artificial Sequence
<220> FEATURE:
<223> OTHER INFORMATION: synthetic construct

<400> SEQUENCE: 279

Gly Phe Ser Leu Ser Ser Tyr Pro Met Ser
1               5                   10

<210> SEQ ID NO 280
<211> LENGTH: 16
<212> TYPE: PRT
<213> ORGANISM: Artificial Sequence
<220> FEATURE:
<223> OTHER INFORMATION: synthetic construct

<400> SEQUENCE: 280

Leu Ile Gly Ser Ser Gly Thr Ile Tyr Phe Ala Thr Trp Ala Lys Gly
1               5                   10                  15

<210> SEQ ID NO 281
<211> LENGTH: 9
<212> TYPE: PRT
<213> ORGANISM: Artificial Sequence
<220> FEATURE:
<223> OTHER INFORMATION: synthetic construct

<400> SEQUENCE: 281

Gly Trp Phe Tyr Tyr Gly Met Asp Leu
1               5

<210> SEQ ID NO 282
<211> LENGTH: 11
<212> TYPE: PRT
<213> ORGANISM: Artificial Sequence
<220> FEATURE:
<223> OTHER INFORMATION: synthetic construct

<400> SEQUENCE: 282

Gln Ala Ser Gln Ser Ile Ser Ser Tyr Leu Ala
1               5                   10

<210> SEQ ID NO 283
<211> LENGTH: 7
<212> TYPE: PRT
<213> ORGANISM: Artificial Sequence
<220> FEATURE:
<223> OTHER INFORMATION: synthetic construct

<400> SEQUENCE: 283

Ser Ala Ser Thr Leu Ala Ser
1               5

<210> SEQ ID NO 284
<211> LENGTH: 13
<212> TYPE: PRT
<213> ORGANISM: Artificial Sequence
<220> FEATURE:
<223> OTHER INFORMATION: synthetic construct

<400> SEQUENCE: 284

Gln Cys His Tyr His Gly Ser Ser Tyr Trp Asp Asn Ser
1               5                   10

<210> SEQ ID NO 285
<211> LENGTH: 11
<212> TYPE: PRT
<213> ORGANISM: Artificial Sequence
<220> FEATURE:
<223> OTHER INFORMATION: synthetic construct

<400> SEQUENCE: 285

Gly Phe Ser Phe Ser Ser Ser Tyr Trp Ile Cys
1               5                   10

<210> SEQ ID NO 286
<211> LENGTH: 18
<212> TYPE: PRT
<213> ORGANISM: Artificial Sequence
<220> FEATURE:
<223> OTHER INFORMATION: synthetic construct

<400> SEQUENCE: 286

Cys Ile Asp Thr Gly Val Ser Gly Asp Thr Tyr Tyr Ala Asn Trp Ala
1               5                   10                  15

Glu Gly

<210> SEQ ID NO 287
<211> LENGTH: 11
<212> TYPE: PRT
<213> ORGANISM: Artificial Sequence
<220> FEATURE:
<223> OTHER INFORMATION: synthetic construct

<400> SEQUENCE: 287

Asp Ile Phe Gly Ser Ala Ile Asp Asn Ser Leu
1               5                   10

<210> SEQ ID NO 288
<211> LENGTH: 11
<212> TYPE: PRT
<213> ORGANISM: Artificial Sequence
<220> FEATURE:
<223> OTHER INFORMATION: synthetic construct

<400> SEQUENCE: 288

Gln Ala Ser Gln Asn Ile Tyr Ser Asn Leu Ala
1               5                   10

<210> SEQ ID NO 289
<211> LENGTH: 7
<212> TYPE: PRT
<213> ORGANISM: Artificial Sequence
<220> FEATURE:
<223> OTHER INFORMATION: synthetic construct

<400> SEQUENCE: 289

Gly Ala Ser Asn Leu Glu Ser
1               5

<210> SEQ ID NO 290
<211> LENGTH: 10
<212> TYPE: PRT
<213> ORGANISM: Artificial Sequence
<220> FEATURE:
<223> OTHER INFORMATION: synthetic construct

<400> SEQUENCE: 290

Gln Gly Gly Tyr Ser Gly Gly Ile Tyr Ala
1               5                   10

<210> SEQ ID NO 291
<211> LENGTH: 10
<212> TYPE: PRT
<213> ORGANISM: Artificial Sequence
<220> FEATURE:
<223> OTHER INFORMATION: synthetic construct

<400> SEQUENCE: 291

Gly Phe Ser Leu Thr Arg His Ala Met Ser
1               5                   10

<210> SEQ ID NO 292
<211> LENGTH: 16
<212> TYPE: PRT
<213> ORGANISM: Artificial Sequence
<220> FEATURE:
<223> OTHER INFORMATION: synthetic construct

<400> SEQUENCE: 292

Ala Ile His Gly Ser Gly Val Thr Asp Tyr Ala Ser Trp Ala Lys Gly
1               5                   10                  15

<210> SEQ ID NO 293
<211> LENGTH: 4
<212> TYPE: PRT
<213> ORGANISM: Artificial Sequence
<220> FEATURE:
<223> OTHER INFORMATION: synthetic construct

<400> SEQUENCE: 293

Gly Ser Gly Leu
1

<210> SEQ ID NO 294
<211> LENGTH: 112
<212> TYPE: PRT
<213> ORGANISM: Artificial Sequence
<220> FEATURE:
<223> OTHER INFORMATION: synthetic construct

<400> SEQUENCE: 294

Asp Ile Val Met Thr Gln Thr Pro Ala Ser Val Glu Ala Ala Val Gly
1               5                   10                  15

Gly Thr Val Thr Ile Lys Cys Gln Ala Ser Gln Ser Ile Tyr Arg Tyr
            20                  25                  30

Leu Ser Trp Tyr Gln Gln Lys Pro Gly Gln Arg Pro Lys Leu Leu Ile
        35                  40                  45

Tyr Gly Ala Ser Asn Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Tyr Ser Ser Ser
                85                  90                  95

Ser Gly Tyr Gly Asn Val Phe Gly Gly Gly Thr Glu Val Val Val Lys
            100                 105                 110

<210> SEQ ID NO 295
<211> LENGTH: 11
<212> TYPE: PRT
<213> ORGANISM: Artificial Sequence
<220> FEATURE:
<223> OTHER INFORMATION: synthetic construct

<400> SEQUENCE: 295

Gln Ala Ser Gln Ser Ile Tyr Arg Tyr Leu Ser
1               5                   10

<210> SEQ ID NO 296
<211> LENGTH: 7
<212> TYPE: PRT
<213> ORGANISM: Artificial Sequence
<220> FEATURE:
<223> OTHER INFORMATION: synthetic construct

<400> SEQUENCE: 296

Gly Ala Ser Asn Leu Ala Ser
1               5

<210> SEQ ID NO 297
<211> LENGTH: 14
<212> TYPE: PRT
<213> ORGANISM: Artificial Sequence
<220> FEATURE:
<223> OTHER INFORMATION: synthetic construct

<400> SEQUENCE: 297

Gln Ser Tyr Tyr Tyr Ser Ser Ser Ser Gly Tyr Gly Asn Val
1               5                   10

<210> SEQ ID NO 298
<211> LENGTH: 122
<212> TYPE: PRT
<213> ORGANISM: Artificial Sequence
<220> FEATURE:
<223> OTHER INFORMATION: synthetic construct

<400> SEQUENCE: 298

Gln Glu Gln Leu Lys Glu Ser Gly Gly Gly Leu Val Gln Pro Gly Gly
1               5                   10                  15

Ser Leu Lys Leu Ser Cys Lys Ala Ser Gly Phe Asp Leu Ser Ser Tyr
            20                  25                  30

Gly Val Ser Trp Val Arg Gln Ala Pro Gly Lys Gly Leu Glu Trp Ile
        35                  40                  45

Gly Tyr Ile Asp Pro Val Phe Gly Ser Thr Tyr Tyr Ala Asn Trp Val
    50                  55                  60

Asn Gly Arg Phe Thr Ile Ser Ser Asp Asn Ala Gln Asn Thr Leu Tyr
65                  70                  75                  80

Leu Gln Leu Asn Ser Leu Thr Ala Ala Asp Thr Ala Thr Tyr Phe Cys
                85                  90                  95

Ala Arg Gly Ser Gly Tyr Val Tyr Tyr Gly Tyr Thr Tyr Asp Leu Trp
            100                 105                 110

Gly Pro Gly Thr Leu Val Thr Val Ser Ser
        115                 120

<210> SEQ ID NO 299
<211> LENGTH: 10
<212> TYPE: PRT
<213> ORGANISM: Artificial Sequence
<220> FEATURE:
<223> OTHER INFORMATION: synthetic construct

<400> SEQUENCE: 299

Gly Phe Asp Leu Ser Ser Tyr Gly Val Ser
1               5                   10

<210> SEQ ID NO 300
<211> LENGTH: 17
<212> TYPE: PRT
<213> ORGANISM: Artificial Sequence
<220> FEATURE:
<223> OTHER INFORMATION: synthetic construct

<400> SEQUENCE: 300

Tyr Ile Asp Pro Val Phe Gly Ser Thr Tyr Tyr Ala Asn Trp Val Asn
1               5                   10                  15
Gly

<210> SEQ ID NO 301
<211> LENGTH: 13
<212> TYPE: PRT
<213> ORGANISM: Artificial Sequence
<220> FEATURE:
<223> OTHER INFORMATION: synthetic construct

<400> SEQUENCE: 301

Gly Ser Gly Tyr Val Tyr Tyr Gly Tyr Thr Tyr Asp Leu
1               5                   10

<210> SEQ ID NO 302
<211> LENGTH: 113
<212> TYPE: PRT
<213> ORGANISM: Artificial Sequence
<220> FEATURE:
<223> OTHER INFORMATION: synthetic construct

<400> SEQUENCE: 302

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Ser Ser
            20                  25                  30

Tyr Asn Gln Lys Asn Tyr Leu Ala Trp Tyr Gln Arg Lys Pro Gly Gln
        35                  40                  45

Ser Pro Lys Leu Leu Val Tyr Phe Ala Ser Gln Arg Ala Thr Gly Val
    50                  55                  60

Pro Asp Arg Phe Ile Gly Ser Gly Ser Gly Ser Asp Phe Thr Leu Thr
65                  70                  75                  80

Ile Ser Ser Val Gln Ala Glu Asp Leu Ala Asp Tyr Phe Cys Gln Gln
                85                  90                  95

His Thr Arg Leu Pro Ile Thr Phe Gly Ala Gly Thr Lys Leu Glu Leu
            100                 105                 110
Lys

<210> SEQ ID NO 303
<211> LENGTH: 17
<212> TYPE: PRT
<213> ORGANISM: Artificial Sequence
<220> FEATURE:
<223> OTHER INFORMATION: synthetic construct

<400> SEQUENCE: 303

Lys Ser Ser Gln Ser Leu Leu Ser Ser Tyr Asn Gln Lys Asn Tyr Leu
1               5                   10                  15
Ala

<210> SEQ ID NO 304
<211> LENGTH: 7
<212> TYPE: PRT

<210> SEQ ID NO 305
<211> LENGTH: 9
<212> TYPE: PRT
<213> ORGANISM: Artificial Sequence
<220> FEATURE:
<223> OTHER INFORMATION: synthetic construct

<400> SEQUENCE: 304

Phe Ala Ser Gln Arg Ala Thr
1               5

<210> SEQ ID NO 305
<211> LENGTH: 9
<212> TYPE: PRT
<213> ORGANISM: Artificial Sequence
<220> FEATURE:
<223> OTHER INFORMATION: synthetic construct

<400> SEQUENCE: 305

Gln Gln His Thr Arg Leu Pro Ile Thr
1               5

<210> SEQ ID NO 306
<211> LENGTH: 119
<212> TYPE: PRT
<213> ORGANISM: Artificial Sequence
<220> FEATURE:
<223> OTHER INFORMATION: synthetic construct

<400> SEQUENCE: 306

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Pro Phe Asn Asp Tyr
            20                  25                  30

Phe Leu Gly Trp Val Lys Gln Ser His Gly Lys Ser Leu Glu Trp Ile
        35                  40                  45

Gly Ser Ile Asn Pro Asp Asn Asp Tyr Thr Met Ser Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Asp Tyr Asp Trp Ala Trp Phe Ala His Trp Gly Gln Gly
                100                 105                 110

Thr Leu Val Thr Val Ser Ala
        115

<210> SEQ ID NO 307
<211> LENGTH: 10
<212> TYPE: PRT
<213> ORGANISM: Artificial Sequence
<220> FEATURE:
<223> OTHER INFORMATION: synthetic construct

<400> SEQUENCE: 307

Gly Tyr Pro Phe Asn Asp Tyr Phe Leu Gly
1               5                   10

<210> SEQ ID NO 308
<211> LENGTH: 17
<212> TYPE: PRT
<213> ORGANISM: Artificial Sequence
<220> FEATURE:
<223> OTHER INFORMATION: synthetic construct

<400> SEQUENCE: 308

```
Ser Ile Asn Pro Asp Asn Asp Tyr Thr Met Ser Asn Gln Lys Phe Lys
1               5                   10                  15

Gly
```

<210> SEQ ID NO 309
<211> LENGTH: 10
<212> TYPE: PRT
<213> ORGANISM: Artificial Sequence
<220> FEATURE:
<223> OTHER INFORMATION: synthetic construct

<400> SEQUENCE: 309

```
Tyr Asp Tyr Asp Trp Ala Trp Phe Ala His
1               5                   10
```

<210> SEQ ID NO 310
<211> LENGTH: 216
<212> TYPE: PRT
<213> ORGANISM: Artificial Sequence
<220> FEATURE:
<223> OTHER INFORMATION: synthetic construct

<400> SEQUENCE: 310

```
Asp Ile Val Met Thr Gln Thr Pro Ala Ser Val Glu Ala Ala Val Gly
1               5                   10                  15

Gly Thr Val Thr Ile Lys Cys Gln Ala Ser Gln Ser Ile Tyr Arg Tyr
            20                  25                  30

Leu Ser Trp Tyr Gln Gln Lys Pro Gly Gln Arg Pro Lys Leu Leu Ile
        35                  40                  45

Tyr Gly Ala Ser Asn Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Tyr Ser Ser Ser
                85                  90                  95

Ser Gly Tyr Gly Asn Val Phe Gly Gly Gly Thr Glu Val Val Val Lys
            100                 105                 110

Gly Asp Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215
```

<210> SEQ ID NO 311
<211> LENGTH: 445
<212> TYPE: PRT
<213> ORGANISM: Artificial Sequence
<220> FEATURE:
<223> OTHER INFORMATION: synthetic construct

<400> SEQUENCE: 311

```
Gln Glu Gln Leu Lys Glu Ser Gly Gly Leu Val Gln Pro Gly Gly
1               5                   10                  15

Ser Leu Lys Leu Ser Cys Lys Ala Ser Gly Phe Asp Leu Ser Ser Tyr
            20                  25                  30

Gly Val Ser Trp Val Arg Gln Ala Pro Gly Lys Gly Leu Glu Trp Ile
        35                  40                  45

Gly Tyr Ile Asp Pro Val Phe Gly Ser Thr Tyr Tyr Ala Asn Trp Val
    50                  55                  60

Asn Gly Arg Phe Thr Ile Ser Ser Asp Asn Ala Gln Asn Thr Leu Tyr
65                  70                  75                  80

Leu Gln Leu Asn Ser Leu Thr Ala Ala Asp Thr Ala Thr Tyr Phe Cys
                85                  90                  95

Ala Arg Gly Ser Gly Tyr Val Tyr Tyr Gly Tyr Thr Tyr Asp Leu Trp
            100                 105                 110

Gly Pro Gly Thr Leu Val Thr Val Ser Ser Gly Gln Pro Lys Ala Pro
        115                 120                 125

Ser Val Phe Pro Leu Ala Pro Cys Cys Gly Asp Thr Pro Ser Ser Thr
    130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
                165                 170                 175

Ser Val Arg Gln Ser Ser Gly Leu Tyr Ser Leu Ser Ser Val Val Ser
            180                 185                 190

Val Thr Ser Ser Ser Gln Pro Val Thr Cys Asn Val Ala His Pro Ala
        195                 200                 205

Thr Asn Thr Lys Val Asp Lys Thr Val Ala Pro Ser Thr Cys Ser Lys
210                 215                 220

Pro Thr Cys Pro Pro Pro Glu Leu Leu Gly Gly Pro Ser Val Phe Ile
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Asp Asp Pro Glu Val Gln
            260                 265                 270

Phe Thr Trp Tyr Ile Asn Asn Glu Gln Val Arg Thr Ala Arg Pro Pro
        275                 280                 285

Leu Arg Glu Gln Gln Phe Asn Ser Thr Ile Arg Val Val Ser Thr Leu
    290                 295                 300

Pro Ile Ala His Gln Asp Trp Leu Arg Gly Lys Glu Phe Lys Cys Lys
305                 310                 315                 320

Val His Asn Lys Ala Leu Pro Ala Pro Ile Glu Lys Thr Ile Ser Lys
                325                 330                 335

Ala Arg Gly Gln Pro Leu Glu Pro Lys Val Tyr Thr Met Gly Pro Pro
            340                 345                 350

Arg Glu Glu Leu Ser Ser Arg Ser Val Ser Leu Thr Cys Met Ile Asn
        355                 360                 365

Gly Phe Tyr Pro Ser Asp Ile Ser Val Glu Trp Glu Lys Asn Gly Lys
    370                 375                 380

Ala Glu Asp Asn Tyr Lys Thr Thr Pro Ala Val Leu Asp Ser Asp Gly
385                 390                 395                 400

Ser Tyr Phe Leu Tyr Ser Lys Leu Ser Val Pro Thr Ser Glu Trp Gln
                405                 410                 415
```

```
Arg Gly Asp Val Phe Thr Cys Ser Val Met His Glu Ala Leu His Asn
            420                 425                 430

His Tyr Thr Gln Lys Ser Ile Ser Arg Ser Pro Gly Lys
        435                 440                 445

<210> SEQ ID NO 312
<211> LENGTH: 220
<212> TYPE: PRT
<213> ORGANISM: Artificial Sequence
<220> FEATURE:
<223> OTHER INFORMATION: synthetic construct

<400> SEQUENCE: 312

Asp Ile Val Met Thr Gln Ser Pro Ser Ser Leu Ala Met Ser Val Gly
1               5                   10                  15

Gln Lys Val Thr Met Ser Cys Lys Ser Gln Ser Leu Leu Ser Ser
            20                  25                  30

Tyr Asn Gln Lys Asn Tyr Leu Ala Trp Tyr Gln Arg Lys Pro Gly Gln
        35                  40                  45

Ser Pro Lys Leu Leu Val Tyr Phe Ala Ser Gln Arg Ala Thr Gly Val
    50                  55                  60

Pro Asp Arg Phe Ile Gly Ser Gly Ser Gly Ser Asp Phe Thr Leu Thr
65                  70                  75                  80

Ile Ser Ser Val Gln Ala Glu Asp Leu Ala Asp Tyr Phe Cys Gln Gln
                85                  90                  95

His Thr Arg Leu Pro Ile Thr Phe Gly Ala Gly Thr Lys Leu Glu Leu
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 313
<211> LENGTH: 443
<212> TYPE: PRT
<213> ORGANISM: Artificial Sequence
<220> FEATURE:
<223> OTHER INFORMATION: synthetic construct

<400> SEQUENCE: 313

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Pro Phe Asn Asp Tyr
            20                  25                  30

Phe Leu Gly Trp Val Lys Gln Ser His Gly Lys Ser Leu Glu Trp Ile
        35                  40                  45

Gly Ser Ile Asn Pro Asp Asn Asp Tyr Thr Met Ser Asn Gln Lys Phe
    50                  55                  60
```

```
Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Asp Tyr Asp Trp Ala Trp Phe Ala His Trp Gly Gln Gly
            100                 105                 110

Thr Leu Val Thr Val Ser Ala Ala Lys Thr Thr Pro Pro Ser Val Tyr
            115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440
```